US010501516B2

(12) United States Patent
Asami et al.

(10) Patent No.: US 10,501,516 B2
(45) Date of Patent: Dec. 10, 2019

(54) PEPTIDE COMPOUND

(71) Applicant: TAKEDA PHARMACEUTICAL COMPANY LIMITED, Osaka (JP)

(72) Inventors: Taiji Asami, Kanagawa (JP); Ayumu Niida, Kanagawa (JP)

(73) Assignee: TAKEDA PHARMACEUTICAL COMPANY LIMITED, Osaka (JP)

(*) Notice: Subject to any disclaimer, the term of this patent is extended or adjusted under 35 U.S.C. 154(b) by 0 days.

(21) Appl. No.: 16/303,975

(22) PCT Filed: May 23, 2017

(86) PCT No.: PCT/JP2017/019220
§ 371 (c)(1),
(2) Date: Nov. 21, 2018

(87) PCT Pub. No.: WO2017/204219
PCT Pub. Date: Nov. 30, 2017

(65) Prior Publication Data
US 2019/0202883 A1 Jul. 4, 2019

(30) Foreign Application Priority Data
May 24, 2016 (JP) .............................. 2016-103011

(51) Int. Cl.
A61K 38/00 (2006.01)
C07K 14/575 (2006.01)
A61K 38/16 (2006.01)
C12N 15/09 (2006.01)
A61P 3/04 (2006.01)
A61P 3/10 (2006.01)

(52) U.S. Cl.
CPC ............ C07K 14/575 (2013.01); A61K 38/16 (2013.01); A61P 3/04 (2018.01); A61P 3/10 (2018.01); C12N 15/09 (2013.01); A61K 38/00 (2013.01)

(58) Field of Classification Search
None
See application file for complete search history.

(56) References Cited

U.S. PATENT DOCUMENTS

| 9,200,051 | B2 | 12/2015 | Asami et al. | |
|---|---|---|---|---|
| 10,131,702 | B2* | 11/2018 | Just | C07K 14/605 |
| 2003/0157107 | A1 | 8/2003 | Miyawaki et al. | |
| 2007/0042952 | A1 | 2/2007 | Dong | |
| 2009/0149378 | A1 | 6/2009 | Dong et al. | |
| 2010/0160556 | A1 | 6/2010 | Wallrapp et al. | |
| 2011/0136725 | A1 | 6/2011 | Dong | |
| 2011/0166062 | A1 | 7/2011 | Dimarchi et al. | |
| 2012/0172293 | A1 | 7/2012 | Asami et al. | |
| 2012/0172295 | A1 | 7/2012 | Dimarchi et al. | |
| 2013/0005646 | A1 | 1/2013 | Schaeffer et al. | |
| 2014/0018291 | A1 | 1/2014 | Vignati et al. | |
| 2014/0162945 | A1 | 6/2014 | Ma et al. | |
| 2014/0303083 | A1 | 10/2014 | Lau et al. | |
| 2015/0299281 | A1 | 10/2015 | Just et al. | |
| 2016/0017016 | A1 | 1/2016 | Bednarek | |

FOREIGN PATENT DOCUMENTS

| CN | 102105159 | 6/2011 |
|---|---|---|
| JP | 2002-538081 | 11/2002 |
| JP | 2007-536214 | 12/2007 |
| JP | 2010-521186 | 6/2010 |
| JP | 2011-524420 | 9/2011 |
| JP | 2011-530509 | 12/2011 |
| JP | 2012/530145 | 11/2012 |
| JP | 2014-501762 | 1/2014 |
| JP | 2014-519511 | 8/2014 |
| JP | 2014-529629 | 11/2014 |
| JP | 2015-517459 | 6/2015 |
| JP | 2016-503772 | 2/2016 |
| JP | 2016-506401 | 3/2016 |
| JP | 2016-512213 | 4/2016 |
| WO | 98/19698 | 5/1998 |
| WO | 98/20895 | 5/1998 |
| WO | 99/47161 | 9/1999 |
| WO | 00/07617 | 2/2000 |
| WO | 01/87341 | 11/2001 |
| WO | 2004/005342 | 1/2004 |
| WO | 2006/049681 | 5/2006 |
| WO | 2006/086769 | 8/2006 |
| WO | 2006/136374 | 12/2006 |
| WO | 2008/008357 | 1/2008 |
| WO | 2008/021560 | 2/2008 |
| WO | 2008/033888 | 3/2008 |

(Continued)

OTHER PUBLICATIONS

International Search Report dated Aug. 15, 2017 in International (PCT) Application No. PCT/JP2017/019220.

Gault et al., "Administration of an acylated GLP-1 and GIP preparation provides added beneficial glucose-lowering and insulinotropic actions over single incretins in mice with Type 2 diabetes and obesity", Clinical Science, vol. 121, 2011, pp. 107-117.

Runge et al., "Differential Structural Properties of GLP-1 and Exendin-4 Determine Their Relative Affinity for the GLP-1 Receptor N-Terminal Extracellular Domain", Biochemistry, vol. 46, 2007, pp. 5830-5840.

(Continued)

Primary Examiner — Jeanette M Lieb

(74) Attorney, Agent, or Firm — Wenderoth, Lind & Ponack, L.L.P.

(57) ABSTRACT

The present invention relates to a peptide compound that may be useful in the treatment or prophylaxis of obesity, diabetes and the like. More specifically, the present invention relates to a peptide compound represented by the formula (I): $P^1$-Tyr-Aib-Glu-Gly-Thr-α-MePhe-Thr-Ser-Asp-Lys(-Gly-Gly-Gly-Gly-$R^{410}$)-A11-A12-Aib-Leu-A15-Lys-Gln-A18-Gln-Iva-Glu-Phe-Val-Arg-His-Leu-Leu-Asn-Lys-Aib-Thr-Arg-Gln-Arg-A35-$NH_2$
wherein each symbol is as defined in the specification, and the treatment or prophylaxis of obesity, diabetes and the like using the peptide compound.

15 Claims, 5 Drawing Sheets
Specification includes a Sequence Listing.

(56) References Cited

FOREIGN PATENT DOCUMENTS

| | | |
|---|---|---|
| WO | 2009/067268 | 5/2009 |
| WO | 2010/011439 | 1/2010 |
| WO | 2010/068735 | 6/2010 |
| WO | 2010/148089 | 12/2010 |
| WO | 2011/002066 | 1/2011 |
| WO | 2011/119657 | 9/2011 |
| WO | 2012/088379 | 6/2012 |
| WO | 2012/138941 | 10/2012 |
| WO | 2012/167744 | 12/2012 |
| WO | 2013/003449 | 1/2013 |
| WO | 2013/037690 | 3/2013 |
| WO | 2013/148117 | 10/2013 |
| WO | 2013/164483 | 11/2013 |
| WO | 2013/167454 | 11/2013 |
| WO | 2013/192129 | 12/2013 |
| WO | 2013/192130 | 12/2013 |
| WO | 2014/096145 | 6/2014 |
| WO | 2014/096150 | 6/2014 |
| WO | 2014/096179 | 6/2014 |
| WO | 2014/192284 | 12/2014 |
| WO | 2015/067716 | 5/2015 |
| WO | 2015/155139 | 10/2015 |
| WO | 2016/084826 | 6/2016 |

OTHER PUBLICATIONS

Al-Sabah et al., "A model for receptor-peptide binding at the glucagon-like peptide-1 (GLP-1) receptor through the analysis of truncated ligands and receptors", British Journal of Pharmacology, vol. 140, 2003, pp. 339-346.

Prophylaxis Definition, Dictionary.com, http://dictionary.reference.com/browse/prophylaxis, 2015.

Huang et al., "Resolving the Conundrum of Islet Transplantation by Linking Metabolic Dysregulation, Inflammation, and Immune Regulation", Endocrine Reviews, vol. 29, No. 5, 2008, pp. 603-630.

Hancock, Director, "Preventing and managing diabetes: an exemplar for NCDs", Collaborating for Health, 2012, pp. 1-8.

Gestational Diabetes—Prevention: Health wise Medical Information on eMedicineHealth, 2015, pp. 1-2.

Choquet et al., "Genetics of Obesity: What have we Learned?", Current Genomics, vol. 12, 2011, pp. 169-179.

He et al., "Reversal of Obesity and Insulin Resistance by a NonPeptidic Glucagon-Like Peptide-1 Receptor Agonist in Diet-Induced Obese Mice", PLoS ONE, Dec. 2010, vol. 5, Issue 12, e14205, pp. 1-15.

Finan et al., "A rationally designed monomeric peptide triagonist corrects obesity and diabetes in rodents", Nature Medicine, Jan. 2015, vol. 21, No. 1, pp. 27-39.

\* cited by examiner

```
                         SEQUENCE LISTING

<160> NUMBER OF SEQ ID NOS: 51

<210> SEQ ID NO 1
<211> LENGTH: 35
<212> TYPE: PRT
<213> ORGANISM: Artificial Sequence
<220> FEATURE:
<223> OTHER INFORMATION: Synthetic Peptide (Formula (I)/(II)/(III))
<220> FEATURE:
<221> NAME/KEY: MISC_FEATURE
<222> LOCATION: (1)..(1)
<223> OTHER INFORMATION: N terminal is modified with P1
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (6)..(6)
<223> OTHER INFORMATION: alpha-METHYLATION
<220> FEATURE:
<221> NAME/KEY: MISC_FEATURE
<222> LOCATION: (10)..(10)
<223> OTHER INFORMATION: In case of formula (I) and (III), linker alkyl
      chain as shown in (Gly-Gly-Gly-Gly-X) is linked to epsilon amino
      group of lysine residue; X = Oda or Pal in formula (I), X=H in
      formula (III)
<220> FEATURE:
<221> NAME/KEY: MISC_FEATURE
<222> LOCATION: (11)..(11)
<223> OTHER INFORMATION: Xaa stands for Aib, Ala or Ser
<220> FEATURE:
<221> NAME/KEY: MISC_FEATURE
<222> LOCATION: (12)..(12)
<223> OTHER INFORMATION: Xaa stands for Ile or Lys
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (15)..(15)
<223> OTHER INFORMATION: Xaa stands for Asp or Glu
<220> FEATURE:
<221> NAME/KEY: MISC_FEATURE
<222> LOCATION: (18)..(18)
<223> OTHER INFORMATION: Xaa stands for Ala or Arg
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib
<220> FEATURE:
<221> NAME/KEY: MISC_FEATURE
<222> LOCATION: (35)..(35)
<223> OTHER INFORMATION: Xaa stands for Tyr or Phe(2-F)
<220> FEATURE:
<221> NAME/KEY: MISC_FEATURE
<222> LOCATION: (35)..(35)
<223> OTHER INFORMATION: AMIDATION

<400> SEQUENCE: 1

Tyr Xaa Glu Gly Thr Phe Thr Ser Asp Lys Xaa Xaa Xaa Leu Xaa Lys
1               5                  10                  15

Gln Xaa Gln Xaa Glu Phe Val Arg His Leu Leu Asn Lys Xaa Thr Arg
            20                  25                  30
```

```
Gln Arg Xaa
        35

<210> SEQ ID NO 2
<211> LENGTH: 16
<212> TYPE: PRT
<213> ORGANISM: Artificial Sequence
<220> FEATURE:
<223> OTHER INFORMATION: Synthetic Peptide (Reference Example 1)
<220> FEATURE:
<221> NAME/KEY: MISC_FEATURE
<222> LOCATION: (1)..(1)
<223> OTHER INFORMATION: Xaa stands for Iva
<220> FEATURE:
<221> NAME/KEY: MISC_FEATURE
<222> LOCATION: (2)..(15)
<223> OTHER INFORMATION: amino group is protedted at positions 2, 5, 6,
      9, 10, 12, 13, 14 and 15
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (16)..(16)
<223> OTHER INFORMATION: 2-fluoro-l-phenylalanine

<400> SEQUENCE: 2

Xaa Glu Phe Val Arg His Leu Leu Asn Lys Xaa Thr Arg Gln Arg Phe
1               5                   10                  15

<210> SEQ ID NO 3
<211> LENGTH: 34
<212> TYPE: PRT
<213> ORGANISM: Artificial Sequence
<220> FEATURE:
<223> OTHER INFORMATION: Synthetic Peptide (Reference Example 2)
<220> FEATURE:
<221> NAME/KEY: MISC_FEATURE
<222> LOCATION: (1)..(1)
<223> OTHER INFORMATION: Xaa stands for Aib
<220> FEATURE:
<221> NAME/KEY: MISC_FEATURE
<222> LOCATION: (2)..(33)
<223> OTHER INFORMATION: amino group is protedted at positions 2, 4, 6,
      7, 8 ,9, 14, 15, 16, 18, 20, 23, 24, 27, 28, 30, 31, 32 and 33
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Xaa stands for Aib
<220> FEATURE:
<221> NAME/KEY: MISC_FEATURE
<222> LOCATION: (12)..(12)
<223> OTHER INFORMATION: Xaa stands for Aib
<220> FEATURE:
<221> NAME/KEY: MISC_FEATURE
<222> LOCATION: (19)..(19)
<223> OTHER INFORMATION: Xaa stands for iva
<220> FEATURE:
<221> NAME/KEY: MISC_FEATURE
<222> LOCATION: (29)..(29)
<223> OTHER INFORMATION: Xaa stands for Aib
<220> FEATURE:
<221> NAME/KEY: MISC_FEATURE
<222> LOCATION: (34)..(34)
<223> OTHER INFORMATION: 2-fluoro-l-phenylalanine

<400> SEQUENCE: 3

Xaa Glu Gly Thr Phe Thr Ser Asp Lys Xaa Ile Xaa Leu Asp Lys Gln
1               5                   10                  15
```

```
Ala Gln Xaa Glu Phe Val Arg His Leu Leu Asn Lys Xaa Thr Arg Gln
            20                  25                  30

Arg Phe

<210> SEQ ID NO 4
<211> LENGTH: 16
<212> TYPE: PRT
<213> ORGANISM: Artificial Sequence
<220> FEATURE:
<223> OTHER INFORMATION: Synthetic Peptide (Reference Example 3)
<220> FEATURE:
<221> NAME/KEY: MISC_FEATURE
<222> LOCATION: (1)..(1)
<223> OTHER INFORMATION: Xaa stands for Iva
<220> FEATURE:
<221> NAME/KEY: MISC_FEATURE
<222> LOCATION: (2)..(15)
<223> OTHER INFORMATION: amino group is protected at positions 2, 5, 6,
      9, 10, 12, 13, 14 and 15
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (16)..(16)
<223> OTHER INFORMATION: 2-fluoro-l-phenylalanine

<400> SEQUENCE: 4

Xaa Glu Phe Val Arg His Leu Leu Asn Lys Xaa Thr Arg Gln Arg Phe
1               5                   10                  15

<210> SEQ ID NO 5
<211> LENGTH: 34
<212> TYPE: PRT
<213> ORGANISM: Artificial Sequence
<220> FEATURE:
<223> OTHER INFORMATION: Synthetic Peptide (Reference Example 4)
<220> FEATURE:
<221> NAME/KEY: MISC_FEATURE
<222> LOCATION: (1)..(1)
<223> OTHER INFORMATION: Xaa stands for Aib
<220> FEATURE:
<221> NAME/KEY: MISC_FEATURE
<222> LOCATION: (2)..(33)
<223> OTHER INFORMATION: amino group is protected at positions 2, 4, 6,
      7, 8, 9, 14, 15, 16, 17, 18, 20, 23, 24, 27, 28, 30, 31, 32 and 33
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Xaa stands for Aib
<220> FEATURE:
<221> NAME/KEY: MISC_FEATURE
<222> LOCATION: (12)..(12)
<223> OTHER INFORMATION: Xaa stands for Aib
<220> FEATURE:
<221> NAME/KEY: MISC_FEATURE
<222> LOCATION: (19)..(19)
<223> OTHER INFORMATION: Xaa stands for Iva
<220> FEATURE:
<221> NAME/KEY: MISC_FEATURE
<222> LOCATION: (29)..(29)
<223> OTHER INFORMATION: Xaa stands for Aib
<220> FEATURE:
<221> NAME/KEY: MISC_FEATURE
<222> LOCATION: (34)..(34)
<223> OTHER INFORMATION: 2-fluoro-l-phenylalanine

<400> SEQUENCE: 5

Xaa Glu Gly Thr Phe Thr Ser Asp Lys Xaa Ile Xaa Leu Asp Lys Gln
```

```
                1               5                  10                  15
Arg Gln Xaa Glu Phe Val Arg His Leu Leu Asn Lys Xaa Thr Arg Gln
            20                  25                  30

Arg Phe

<210> SEQ ID NO 6
<211> LENGTH: 16
<212> TYPE: PRT
<213> ORGANISM: Artificial Sequence
<220> FEATURE:
<223> OTHER INFORMATION: Synthetic Peptide (Reference Example 5)
<220> FEATURE:
<221> NAME/KEY: MISC_FEATURE
<222> LOCATION: (1)..(1)
<223> OTHER INFORMATION: Xaa stands for Iva
<220> FEATURE:
<221> NAME/KEY: MISC_FEATURE
<222> LOCATION: (2)..(16)
<223> OTHER INFORMATION: amino group is protected at positions 2, 5, 6,
      9, 10, 12, 13, 14, 15 and 16
<220> FEATURE:
<221> NAME/KEY: MISC_FEATURE
<222> LOCATION: (11)..(11)
<223> OTHER INFORMATION: Xaa stands for Aib

<400> SEQUENCE: 6

Xaa Glu Phe Val Arg His Leu Leu Asn Lys Xaa Thr Arg Gln Arg Tyr
1               5                   10                  15

<210> SEQ ID NO 7
<211> LENGTH: 34
<212> TYPE: PRT
<213> ORGANISM: Artificial Sequence
<220> FEATURE:
<223> OTHER INFORMATION: Synthetic Peptide (Reference Example 6)
<220> FEATURE:
<221> NAME/KEY: MISC_FEATURE
<222> LOCATION: (1)..(1)
<223> OTHER INFORMATION: Xaa stands for Aib
<220> FEATURE:
<221> NAME/KEY: MISC_FEATURE
<222> LOCATION: (2)..(34)
<223> OTHER INFORMATION: amino group is protected at positions 2, 4, 6,
      7, 8, 9, 14, 15, 16, 17, 18, 20, 23, 24, 27, 28, 30, 31, 32, 33
      and 34
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Xaa stands for Aib
<220> FEATURE:
<221> NAME/KEY: MISC_FEATURE
<222> LOCATION: (12)..(12)
<223> OTHER INFORMATION: Xaa stands for Aib
<220> FEATURE:
<221> NAME/KEY: MISC_FEATURE
<222> LOCATION: (19)..(19)
<223> OTHER INFORMATION: Xaa stands for Iva
<220> FEATURE:
<221> NAME/KEY: MISC_FEATURE
<222> LOCATION: (29)..(29)
<223> OTHER INFORMATION: Xaa stands for Aib

<400> SEQUENCE: 7

Xaa Glu Gly Thr Phe Thr Ser Asp Lys Xaa Ile Xaa Leu Asp Lys Gln
1               5                   10                  15

Arg Gln Xaa Glu Phe Val Arg His Leu Leu Asn Lys Xaa Thr Arg Gln
            20                  25                  30
```

Arg Tyr

<210> SEQ ID NO 8
<211> LENGTH: 16
<212> TYPE: PRT
<213> ORGANISM: Artificial Sequence
<220> FEATURE:
<223> OTHER INFORMATION: Synthetic Peptide (Reference Example7)
<220> FEATURE:
<221> NAME/KEY: MISC_FEATURE
<222> LOCATION: (1)..(1)
<223> OTHER INFORMATION: Xaa stands for Iva
<220> FEATURE:
<221> NAME/KEY: MISC_FEATURE
<222> LOCATION: (2)..(16)
<223> OTHER INFORMATION: amino group is protected at positions 2, 5, 6,
      9, 10, 12, 13, 14, 15 and 16
<220> FEATURE:
<221> NAME/KEY: MISC_FEATURE
<222> LOCATION: (11)..(11)
<223> OTHER INFORMATION: Xaa stands for Aib

<400> SEQUENCE: 8

Xaa Glu Phe Val Arg His Leu Leu Asn Lys Xaa Thr Arg Gln Arg Tyr
1               5                   10                  15

<210> SEQ ID NO 9
<211> LENGTH: 34
<212> TYPE: PRT
<213> ORGANISM: Artificial Sequence
<220> FEATURE:
<223> OTHER INFORMATION: Synthetic Peptide (Reference Example 8)
<220> FEATURE:
<221> NAME/KEY: MISC_FEATURE
<222> LOCATION: (1)..(1)
<223> OTHER INFORMATION: Xaa stands for Aib
<220> FEATURE:
<221> NAME/KEY: MISC_FEATURE
<222> LOCATION: (2)..(34)
<223> OTHER INFORMATION: amino group is protected at positions 2, 4, 6,
      7, 8, 9, 14, 15, 16, 18, 20, 23, 24, 27, 28, 30, 31, 32, 33 and 34
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Xaa stands for Aib
<220> FEATURE:
<221> NAME/KEY: MISC_FEATURE
<222> LOCATION: (12)..(12)
<223> OTHER INFORMATION: Xaa stands for Aib
<220> FEATURE:
<221> NAME/KEY: MISC_FEATURE
<222> LOCATION: (19)..(19)
<223> OTHER INFORMATION: Xaa stands for Iva
<220> FEATURE:
<221> NAME/KEY: MISC_FEATURE
<222> LOCATION: (29)..(29)
<223> OTHER INFORMATION: Xaa stands for Aib

<400> SEQUENCE: 9

Xaa Glu Gly Thr Phe Thr Ser Asp Lys Xaa Ile Xaa Leu Asp Lys Gln
1               5                   10                  15

Ala Gln Xaa Glu Phe Val Arg His Leu Leu Asn Lys Xaa Thr Arg Gln
            20                  25                  30

Arg Tyr

<210> SEQ ID NO 10
<211> LENGTH: 35
<212> TYPE: PRT

<213> ORGANISM: Artificial Sequence
<220> FEATURE:
<223> OTHER INFORMATION: Synthetic Peptide (Example 1)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
    (Gly-Gly-Gly-Gly-Pal) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib
<220> FEATURE:
<221> NAME/KEY: MISC_FEATURE
<222> LOCATION: (35)..(35)
<223> OTHER INFORMATION: 2-fluoro-l-phenylalanine

<400> SEQUENCE: 10

Tyr Xaa Glu Gly Thr Phe Thr Ser Asp Lys Xaa Ile Xaa Leu Asp Lys
1               5                   10                  15

Gln Ala Gln Xaa Glu Phe Val Arg His Leu Leu Asn Lys Xaa Thr Arg
            20                  25                  30

Gln Arg Phe
        35

<210> SEQ ID NO 11
<211> LENGTH: 35
<212> TYPE: PRT
<213> ORGANISM: Artificial Sequence
<220> FEATURE:
<223> OTHER INFORMATION: Synthetic Peptide (Example 2)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
    (Gly-Gly-Gly-Gly-Oda) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)

```
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib
<220> FEATURE:
<221> NAME/KEY: MISC_FEATURE
<222> LOCATION: (35)..(35)
<223> OTHER INFORMATION: 2-fluoro-l-phenylalanine

<400> SEQUENCE: 11

Tyr Xaa Glu Gly Thr Phe Thr Ser Asp Lys Xaa Ile Xaa Leu Asp Lys
1               5                   10                  15

Gln Ala Gln Xaa Glu Phe Val Arg His Leu Leu Asn Lys Xaa Thr Arg
            20                  25                  30

Gln Arg Phe
        35

<210> SEQ ID NO 12
<211> LENGTH: 35
<212> TYPE: PRT
<213> ORGANISM: Artificial Sequence
<220> FEATURE:
<223> OTHER INFORMATION: Synthetic Peptide (Example 3)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib
<220> FEATURE:
<221> NAME/KEY: MISC_FEATURE
<222> LOCATION: (35)..(35)
<223> OTHER INFORMATION: 2-fluoro-l-phenylalanine

<400> SEQUENCE: 12

Tyr Xaa Glu Gly Thr Phe Thr Ser Asp Lys Xaa Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Phe
        35

<210> SEQ ID NO 13
<211> LENGTH: 35
<212> TYPE: PRT
<213> ORGANISM: Artificial Sequence
<220> FEATURE:
```

-continued

```
<223> OTHER INFORMATION: Synthetic Peptide (Example 4)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib
<220> FEATURE:
<221> NAME/KEY: MISC_FEATURE
<222> LOCATION: (35)..(35)
<223> OTHER INFORMATION: 2-fluoro-l-phenylalanine

<400> SEQUENCE: 13

Tyr Xaa Glu Gly Thr Phe Thr Ser Asp Lys Xaa Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Phe
        35

<210> SEQ ID NO 14
<211> LENGTH: 35
<212> TYPE: PRT
<213> ORGANISM: Artificial Sequence
<220> FEATURE:
<223> OTHER INFORMATION: Synthetic Peptide (Example 5)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
```

```
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib
<220> FEATURE:
<221> NAME/KEY: MISC_FEATURE
<222> LOCATION: (35)..(35)
<223> OTHER INFORMATION: 2-fluoro-l-phenylalanine

<400> SEQUENCE: 14

Tyr Xaa Glu Gly Thr Phe Thr Ser Asp Lys Xaa Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Phe
        35

<210> SEQ ID NO 15
<211> LENGTH: 35
<212> TYPE: PRT
<213> ORGANISM: Artificial Sequence
<220> FEATURE:
<223> OTHER INFORMATION: Synthetic Peptide (Example 6)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib
<220> FEATURE:
<221> NAME/KEY: MISC_FEATURE
<222> LOCATION: (35)..(35)
<223> OTHER INFORMATION: 2-fluoro-l-phenylalanine

<400> SEQUENCE: 15

Tyr Xaa Glu Gly Thr Phe Thr Ser Asp Lys Xaa Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Phe
        35
```

```
<210> SEQ ID NO 16
<211> LENGTH: 35
<212> TYPE: PRT
<213> ORGANISM: Artificial Sequence
<220> FEATURE:
<223> OTHER INFORMATION: Synthetic Peptide (Example 7)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 16

Tyr Xaa Glu Gly Thr Phe Thr Ser Asp Lys Xaa Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 17
<211> LENGTH: 35
<212> TYPE: PRT
<213> ORGANISM: Artificial Sequence
<220> FEATURE:
<223> OTHER INFORMATION: Synthetic Peptide (Example 8)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
```

```
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 17

Tyr Xaa Glu Gly Thr Phe Thr Ser Asp Lys Xaa Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 18
<211> LENGTH: 35
<212> TYPE: PRT
<213> ORGANISM: Artificial Sequence
<220> FEATURE:
<223> OTHER INFORMATION: Synthetic Peptide (Example 9)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 18

Tyr Xaa Glu Gly Thr Phe Thr Ser Asp Lys Xaa Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 19
<211> LENGTH: 35
<212> TYPE: PRT
<213> ORGANISM: Artificial Sequence
<220> FEATURE:
```

```
<223> OTHER INFORMATION: Synthetic Peptide (Example 10)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 19

Tyr Xaa Glu Gly Thr Phe Thr Ser Asp Lys Xaa Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 20
<211> LENGTH: 35
<212> TYPE: PRT
<213> ORGANISM: Artificial Sequence
<220> FEATURE:
<223> OTHER INFORMATION: Synthetic Peptide (Example 11)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib
```

<400> SEQUENCE: 20

Tyr Xaa Glu Gly Thr Phe Thr Ser Asp Lys Ala Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 21
<211> LENGTH: 35
<212> TYPE: PRT
<213> ORGANISM: Artificial Sequence
<220> FEATURE:
<223> OTHER INFORMATION: Synthetic Peptide (Example 12)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 21

Tyr Xaa Glu Gly Thr Phe Thr Ser Asp Lys Ala Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 22
<211> LENGTH: 35
<212> TYPE: PRT
<213> ORGANISM: Artificial Sequence
<220> FEATURE:
<223> OTHER INFORMATION: Synthetic Peptide (Example 13)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine

```
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 22

Tyr Xaa Glu Gly Thr Phe Thr Ser Asp Lys Ala Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 23
<211> LENGTH: 35
<212> TYPE: PRT
<213> ORGANISM: Artificial Sequence
<220> FEATURE:
<223> OTHER INFORMATION: Synthetic Peptide (Example 14)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 23

Tyr Xaa Glu Gly Thr Phe Thr Ser Asp Lys Ala Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 24
<211> LENGTH: 35
<212> TYPE: PRT
<213> ORGANISM: Artificial Sequence
<220> FEATURE:
<223> OTHER INFORMATION: Synthetic Peptide (Example 15)
```

```
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 24

Tyr Xaa Glu Gly Thr Phe Thr Ser Asp Lys Ser Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 25
<211> LENGTH: 35
<212> TYPE: PRT
<213> ORGANISM: Artificial Sequence
<220> FEATURE:
<223> OTHER INFORMATION: Synthetic Peptide (Example 16)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 25

Tyr Xaa Glu Gly Thr Phe Thr Ser Asp Lys Ser Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
```

<210> SEQ ID NO 26
<211> LENGTH: 35
<212> TYPE: PRT
<213> ORGANISM: Artificial Sequence
<220> FEATURE:
<223> OTHER INFORMATION: Synthetic Peptide (Example 17)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 26

Tyr Xaa Glu Gly Thr Phe Thr Ser Asp Lys Ser Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 27
<211> LENGTH: 35
<212> TYPE: PRT
<213> ORGANISM: Artificial Sequence
<220> FEATURE:
<223> OTHER INFORMATION: Synthetic Peptide (Example 18)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:

```
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 27

Tyr Xaa Glu Gly Thr Phe Thr Ser Asp Lys Ser Ile Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 28
<211> LENGTH: 35
<212> TYPE: PRT
<213> ORGANISM: Artificial Sequence
<220> FEATURE:
<223> OTHER INFORMATION: Synthetic Peptide (Example 19)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 28

Tyr Xaa Glu Gly Thr Phe Thr Ser Asp Lys Xaa Lys Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 29
<211> LENGTH: 35
<212> TYPE: PRT
<213> ORGANISM: Artificial Sequence
<220> FEATURE:
<223> OTHER INFORMATION: Synthetic Peptide (Example 20)
<220> FEATURE:
<221> NAME/KEY: MISC_FEATURE
<222> LOCATION: (2)..(2)
<223> OTHER INFORMATION: Xaa stands for Aib
<220> FEATURE:
```

```
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 29

Tyr Xaa Glu Gly Thr Phe Thr Ser Asp Lys Xaa Lys Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 30
<211> LENGTH: 35
<212> TYPE: PRT
<213> ORGANISM: Artificial Sequence
<220> FEATURE:
<223> OTHER INFORMATION: Synthetic Peptide (Example 21)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 30
```

```
Tyr Xaa Glu Gly Thr Phe Thr Ser Asp Lys Xaa Lys Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 31
<211> LENGTH: 34
<212> TYPE: PRT
<213> ORGANISM: Artificial Sequence
<220> FEATURE:
<223> OTHER INFORMATION: Synthetic Peptide (Example 22)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 31

Tyr Xaa Glu Gly Thr Phe Thr Ser Asp Lys Xaa Lys Xaa Leu Asp Lys
1               5                   10                  15

Gln Arg Gln Xaa Glu Phe Val Arg His Leu Leu Asn Lys Xaa Thr Arg
            20                  25                  30

Gln Arg

<210> SEQ ID NO 32
<211> LENGTH: 35
<212> TYPE: PRT
<213> ORGANISM: Artificial Sequence
<220> FEATURE:
<223> OTHER INFORMATION: Synthetic Peptide (Example 23)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
```

```
        (Gly-Gly-Gly-Gly-Pal) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 32

Tyr Xaa Glu Gly Thr Phe Thr Ser Asp Lys Ser Lys Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 33
<211> LENGTH: 35
<212> TYPE: PRT
<213> ORGANISM: Artificial Sequence
<220> FEATURE:
<223> OTHER INFORMATION: Synthetic Peptide (Example 24)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
        (Gly-Gly-Gly-Gly-Oda) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 33

Tyr Xaa Glu Gly Thr Phe Thr Ser Asp Lys Ser Lys Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 34
<211> LENGTH: 35
<212> TYPE: PRT
<213> ORGANISM: Artificial Sequence
<220> FEATURE:
<223> OTHER INFORMATION: Synthetic Peptide (Example 25)
<220> FEATURE:
<221> NAME/KEY: MISC_FEATURE
<222> LOCATION: (1)..(1)
```

```
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 34

Tyr Xaa Glu Gly Thr Phe Thr Ser Asp Lys Ser Lys Xaa Leu Asp Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 35
<211> LENGTH: 35
<212> TYPE: PRT
<213> ORGANISM: Artificial Sequence
<220> FEATURE:
<223> OTHER INFORMATION: Synthetic Peptide (Example 26)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
    (Gly-Gly-Gly-Gly-Oda) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 35

Tyr Xaa Glu Gly Thr Phe Thr Ser Asp Lys Ser Lys Xaa Leu Asp Lys
1               5                   10                  15
```

```
Gln Arg Gln Xaa Glu Phe Val Arg His Leu Leu Asn Lys Xaa Thr Arg
            20                  25                  30

Gln Arg Tyr
        35

<210> SEQ ID NO 36
<211> LENGTH: 35
<212> TYPE: PRT
<213> ORGANISM: Artificial Sequence
<220> FEATURE:
<223> OTHER INFORMATION: Synthetic Peptide (Example 27)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 36

Tyr Xaa Glu Gly Thr Phe Thr Ser Asp Lys Xaa Ile Xaa Leu Asp Lys
1               5                   10                  15

Gln Ala Gln Xaa Glu Phe Val Arg His Leu Leu Asn Lys Xaa Thr Arg
            20                  25                  30

Gln Arg Tyr
        35

<210> SEQ ID NO 37
<211> LENGTH: 35
<212> TYPE: PRT
<213> ORGANISM: Artificial Sequence
<220> FEATURE:
<223> OTHER INFORMATION: Synthetic Peptide (Example 28)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
```

```
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 37

Tyr Xaa Glu Gly Thr Phe Thr Ser Asp Lys Xaa Ile Xaa Leu Asp Lys
1               5                   10                  15

Gln Ala Gln Xaa Glu Phe Val Arg His Leu Leu Asn Lys Xaa Thr Arg
            20                  25                  30

Gln Arg Tyr
        35

<210> SEQ ID NO 38
<211> LENGTH: 35
<212> TYPE: PRT
<213> ORGANISM: Artificial Sequence
<220> FEATURE:
<223> OTHER INFORMATION: Synthetic Peptide (Example 29)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 38

Tyr Xaa Glu Gly Thr Phe Thr Ser Asp Lys Xaa Ile Xaa Leu Asp Lys
1               5                   10                  15

Gln Ala Gln Xaa Glu Phe Val Arg His Leu Leu Asn Lys Xaa Thr Arg
            20                  25                  30

Gln Arg Tyr
        35

<210> SEQ ID NO 39
<211> LENGTH: 35
```

-continued

```
<212> TYPE: PRT
<213> ORGANISM: Artificial Sequence
<220> FEATURE:
<223> OTHER INFORMATION: Synthetic Peptide (Example 30)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 39

Tyr Xaa Glu Gly Thr Phe Thr Ser Asp Lys Xaa Ile Xaa Leu Asp Lys
1               5                   10                  15

Gln Ala Gln Xaa Glu Phe Val Arg His Leu Leu Asn Lys Xaa Thr Arg
            20                  25                  30

Gln Arg Tyr
        35

<210> SEQ ID NO 40
<211> LENGTH: 35
<212> TYPE: PRT
<213> ORGANISM: Artificial Sequence
<220> FEATURE:
<223> OTHER INFORMATION: Synthetic Peptide (Example 31)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
```

```
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 40

Tyr Xaa Glu Gly Thr Phe Thr Ser Asp Lys Xaa Ile Xaa Leu Glu Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 41
<211> LENGTH: 35
<212> TYPE: PRT
<213> ORGANISM: Artificial Sequence
<220> FEATURE:
<223> OTHER INFORMATION: Synthetic Peptide (Example 32)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 41

Tyr Xaa Glu Gly Thr Phe Thr Ser Asp Lys Xaa Ile Xaa Leu Glu Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 42
<211> LENGTH: 35
<212> TYPE: PRT
<213> ORGANISM: Artificial Sequence
<220> FEATURE:
<223> OTHER INFORMATION: Synthetic Peptide (Example 33)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
```

```
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 42

Tyr Xaa Glu Gly Thr Phe Thr Ser Asp Lys Xaa Ile Xaa Leu Glu Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 43
<211> LENGTH: 35
<212> TYPE: PRT
<213> ORGANISM: Artificial Sequence
<220> FEATURE:
<223> OTHER INFORMATION: Synthetic Peptide (Example 34)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib
```

<400> SEQUENCE: 43

Tyr Xaa Glu Gly Thr Phe Thr Ser Asp Lys Xaa Ile Xaa Leu Glu Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 44
<211> LENGTH: 35
<212> TYPE: PRT
<213> ORGANISM: Artificial Sequence
<220> FEATURE:
<223> OTHER INFORMATION: Synthetic Peptide (Example 35)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 44

Tyr Xaa Glu Gly Thr Phe Thr Ser Asp Lys Ala Ile Xaa Leu Glu Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 45
<211> LENGTH: 35
<212> TYPE: PRT
<213> ORGANISM: Artificial Sequence
<220> FEATURE:
<223> OTHER INFORMATION: Synthetic Peptide (Example 36)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (13)..(13)

```
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 45

Tyr Xaa Glu Gly Thr Phe Thr Ser Asp Lys Ala Ile Xaa Leu Glu Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 46
<211> LENGTH: 35
<212> TYPE: PRT
<213> ORGANISM: Artificial Sequence
<220> FEATURE:
<223> OTHER INFORMATION: Synthetic Peptide (Example 37)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 46

Tyr Xaa Glu Gly Thr Phe Thr Ser Asp Lys Ala Ile Xaa Leu Glu Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 47
<211> LENGTH: 35
<212> TYPE: PRT
<213> ORGANISM: Artificial Sequence
<220> FEATURE:
<223> OTHER INFORMATION: Synthetic Peptide (Example 38)
<220> FEATURE:
<221> NAME/KEY: MISC_FEATURE
<222> LOCATION: (1)..(1)
```

```
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 47

Tyr Xaa Glu Gly Thr Phe Thr Ser Asp Lys Ala Ile Xaa Leu Glu Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 48
<211> LENGTH: 35
<212> TYPE: PRT
<213> ORGANISM: Artificial Sequence
<220> FEATURE:
<223> OTHER INFORMATION: Synthetic Peptide (Example 39)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 48

Tyr Xaa Glu Gly Thr Phe Thr Ser Asp Lys Ser Ile Xaa Leu Glu Lys
1               5                   10                  15

Gln Arg Gln Xaa Glu Phe Val Arg His Leu Leu Asn Lys Xaa Thr Arg
            20                  25                  30

Gln Arg Tyr
```

```
<210> SEQ ID NO 49
<211> LENGTH: 35
<212> TYPE: PRT
<213> ORGANISM: Artificial Sequence
<220> FEATURE:
<223> OTHER INFORMATION: Synthetic Peptide (Example 40)
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 49

Tyr Xaa Glu Gly Thr Phe Thr Ser Asp Lys Ser Ile Xaa Leu Glu Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 50
<211> LENGTH: 35
<212> TYPE: PRT
<213> ORGANISM: Artificial Sequence
<220> FEATURE:
<223> OTHER INFORMATION: Synthetic Peptide (Example 41)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Pal) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
```

```
<221> NAME/KEY: MISC_FEATURE
<222> LOCATION: (30)..(30)
<223> OTHER INFORMATION: Xaa stands for Aib

<400> SEQUENCE: 50

Tyr Xaa Glu Gly Thr Phe Thr Ser Asp Lys Ser Ile Xaa Leu Glu Lys
1               5                   10                  15

Gln Arg Gln Xaa Glu Phe Val Arg His Leu Leu Asn Lys Xaa Thr Arg
            20                  25                  30

Gln Arg Tyr
        35

<210> SEQ ID NO 51
<211> LENGTH: 35
<212> TYPE: PRT
<213> ORGANISM: Artificial Sequence
<220> FEATURE:
<223> OTHER INFORMATION: Synthetic Peptide (Example 42)
<220> FEATURE:
<221> NAME/KEY: MISC_FEATURE
<222> LOCATION: (1)..(1)
<223> OTHER INFORMATION: N-terminal METHYLATION
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MISC_FEATURE
<222> LOCATION: (5)..(5)
<223> OTHER INFORMATION: alpha-METHYLATION
<220> FEATURE:
<221> NAME/KEY: MISC_FEATURE
<222> LOCATION: (10)..(10)
<223> OTHER INFORMATION: Linker alkyl chain as shown in
      (Gly-Gly-Gly-Gly-Oda) is linked to epsilon amino group of lysine
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MISC_FEATURE
<222> LOCATION: (20)..(20)
<223> OTHER INFORMATION: Xaa stands for Iva
<220> FEATURE:
<221> NAME/KEY: MISC_FEATURE
<222> LOCATION: (30)..(30)
<223> OTHER INFORMATION: Xaa stands for Aib

<400> SEQUENCE: 51

Tyr Xaa Glu Gly Thr Phe Thr Ser Asp Lys Ser Ile Xaa Leu Glu Lys
1               5                   10                  15

Gln Arg Gln Xaa Glu Phe Val Arg His Leu Leu Asn Lys Xaa Thr Arg
            20                  25                  30

Gln Arg Tyr
        35
```

PEPTIDE COMPOUND

BACKGROUND OF THE INVENTION

Field of the Invention

The present invention relates to a peptide compound that may be useful in the treatment or prophylaxis of obesity, diabetes and the like on the basis of its activating action on Y2 receptors, GLP-1 receptors and GIP receptors.

Background of the Invention

Peptide YY (PYY) is a peptide consisting of 36 amino acid residues, which is isolated from the porcine upper small intestine. PYY belongs to the pancreatic polypeptide (PP) family together with neuropeptide Y (NPY) isolated from the porcine brain (Patent Literature 1 and Patent Literature 2).

It is known that PYY is secreted from endocrine cells (L cells) of the gastrointestinal tract along with diet ingestion, and exhibits a feeding suppressive action via Y2 receptors. The intestine/hypothalamus pathway via Y2 receptors of hypothalamic arcuate nucleus NPY/AgRP-expressing nerve cells, and the vagal afferent pathway via Y2 receptors of vagal nerve ending have been reported as pathways of this action.

It has also been reported that patients with anorexia nervosa (AN) involving disordered eating patterns have high PYY concentrations in the cerebrospinal fluid, and patients with bulimia nervosa (BN) exhibit extremely slow postprandial elevation of PYY concentrations in blood as compared to that of healthy individuals. Furthermore, it is known that PYY concentrations in the blood of obesity patients are lower than those of healthy individuals.

Both glucagon-like peptide-1 (GLP-1) and glucose-dependent insulinotropic polypeptide (GIP) are peptides called incretin. GLP-1 and GIP are secreted from small intestinal L cells and K cells, respectively. GLP-1 acts via GLP-1 receptors and is known to have a sugar-dependent insulinotropic action and a feeding suppressive action. On the other hand, GIP is known to have a sugar-dependent insulinotropic action via GIP receptors, though its influence on feeding is not clear.

A GLP-1 receptor/GIP receptor coagonist peptide has been reported to show a stronger hypoglycemic action and body weight-lowering action than those of a GLP-1 receptor agonist alone (Patent Literature 3). Also, Attempts have also been made to search for peptides having GLP-1 receptor/GIP receptor coagonist activity and develop these peptides as antiobesity drugs or therapeutic drugs for diabetes, on the basis of the structure of natural glucagon, GIP, or GLP-1 (Patent Literatures 3 to 6).

CITATION LIST

Patent Literature

[PTL 1] WO2006/049681
[PTL 2] WO2011/002066
[PTL 3] WO2010/011439
[PTL 4] WO2013/164483
[PTL 5] WO2014/192284
[PTL 6] WO2016/084826

The present invention aims to provide a peptide compound that has an activating action on Y2 receptors, GLP-1 receptors and GIP receptors, and is useful as an agent for the prophylaxis or treatment of obesity and diabetes and the like.

SUMMARY OF THE INVENTION

The present inventors have conducted intensive studies about a peptide compound that may be useful as an agent for the prophylaxis or treatment of obesity and diabetes and the like on the basis of its activating action on Y2 receptors, GLP-1 receptors and GIP receptors, and consequently found that a peptide compound having a sequence represented by the formula (I) shown below may be useful in the prophylaxis or treatment of obesity or diabetes on the basis of its activating action on Y2 receptors, GLP-1 receptors and GIP receptors, which resulted in the completion of the present invention.

Accordingly, the present invention relates to the following [1] to [17]:

[1] A peptide represented by the formula (I):

(SEQ ID NO: 1)
P$^1$-Tyr-Aib-Glu-Gly-Thr-α-MePhe-Thr-Ser-Asp-

Lys(-Gly-Gly-Gly-Gly-R$^{410}$)-A11-A12-Aib-Leu-A15-

Lys-Gln-A18-Gln-Iva-Glu-Phe-Val-Arg-His-Leu-Leu-

Asn-Lys-Aib-Thr-Arg-Gln-Arg-A35-NH$_2$ wherein
P$^2$ is a group represented by the formula:
—R$^{41}$,
—CO—R$^{41}$,
—CO—OR$^{41}$,
—CO—COR$^{41}$,
—SO—R$^{41}$,
—SO$_2$—R$^{41}$,
—SO$_2$—OR$^{41}$,
—CO—NR$^{42}$R$^{43}$,
—SO$_2$—NR$^{42}$R$^{43}$,
or
—C(=NR$^{41}$)—NR$^{42}$R$^{43}$
wherein R$^{41}$, R$^{42}$ and R$^{43}$ are each independently a hydrogen atom, an optionally substituted hydrocarbon group, or an optionally substituted heterocyclic group;
R$^{410}$ is Pal or Oda;
A11 is Aib, Ala or Ser (A11 is preferably Aib, is preferably Ala in an alternative embodiment, and is preferably Ser in an alternative embodiment);
A12 is Ile or Lys;
A15 is Asp or Glu;
A18 is Ala or Arg; and
A35 is Tyr or Phe(2-F),
or a salt thereof (hereinafter sometimes to be abbreviated as compound (I))

[2] The peptide according to the above-mentioned [1] or a salt thereof, wherein P$^1$ is a hydrogen atom or a methyl group.
[3] The peptide according to the above-mentioned [1] or a salt thereof, wherein R$^{410}$ is Pal.
[4] The peptide according to the above-mentioned [1] or a salt thereof, wherein A12 is Ile.
[5] The peptide according to the above-mentioned [1] or a salt thereof, wherein A15 is Glu.
[6] The peptide according to the above-mentioned [1] or a salt thereof, wherein A18 is Arg.
[7] The peptide according to the above-mentioned [1] or a salt thereof, wherein A35 is Tyr.

[8] H-Tyr-Aib-Glu-Gly-Thr-αMePhe-Thr-Ser-Asp-Lys(-Gly-Gly-Gly-Gly-Pal)-Aib-Ile-Aib-Leu-Glu-Lys-Gln-Arg-Gln-Iva-Glu-Phe-Val-Arg-His-Leu-Leu-Asn-Lys-Aib-Thr-Arg-Gln-Arg-Tyr-NH$_2$ or a salt thereof.

[9] H-Tyr-Aib-Glu-Gly-Thr-αMePhe-Thr-Ser-Asp-Lys(-Gly-Gly-Gly-Gly-Pal)-Ala-Ile-Aib-Leu-Glu-Lys-Gln-Arg-Gln-Iva-Glu-Phe-Val-Arg-His-Leu-Leu-Asn-Lys-Aib-Thr-Arg-Gln-Arg-Tyr-NH$_2$ or a salt thereof.

[10] Me-Tyr-Aib-Glu-Gly-Thr-αMePhe-Thr-Ser-Asp-Lys(-Gly-Gly-Gly-Gly-Pal)-Ser-Ile-Aib-Leu-Glu-Lys-Gln-Arg-Gln-Iva-Glu-Phe-Val-Arg-His-Leu-Leu-Asn-Lys-Aib-Thr-Arg-Gln-Arg-Tyr-NH$_2$
or a salt thereof.

[11] A medicament comprising the peptide according to the above-mentioned [1] or a salt thereof.

[12] The medicament according to the above-mentioned [11], which is an activator of a Y2 receptor, a GLP-1 receptor and a GIP receptor.

[13] The medicament according to the above-mentioned [11], which is an agent for the prophylaxis or treatment of obesity or diabetes.

[14] A method for the prophylaxis or treatment of obesity or diabetes in a mammal, comprising administering an effective amount of the peptide according to the above-mentioned [1] or a salt thereof to the mammal.

[15] A method for activating a Y2 receptor, a GLP-1 receptor and a GIP receptor in a mammal, comprising administering an effective amount of the peptide according to the above-mentioned [1] or a salt thereof to the mammal.

[16] Use of the peptide according to the above-mentioned [1] or a salt thereof for the manufacture of an agent for the prophylaxis or treatment of obesity or diabetes.

[17] The peptide according to the above-mentioned [1] or a salt thereof for use in the prophylaxis or treatment of obesity or diabetes.

Compound (I) may have a feeding suppressive action and a body weight-lowering action in vivo on the basis of its activating action on Y2 receptors, GLP-1 receptors and GIP receptors. Therefore, compound (I) may be useful as an agent for the prophylaxis and/or treatment of obesity or diabetes.

BRIEF DESCRIPTION OF THE DRAWINGS

FIG. 1A shows daily changes in body weight. FIG. 1B shows % inhibition of cumulative food intake. FIG. 1C shows body fat mass measured in EchoMRI. FIG. 1D shows body lean mass. FIG. 1E shows fat pad weight. FIG. 1F shows liver weight. FIG. 1G shows liver TG content. FIG. 1H shows hematoxylin-eosin staining of liver slices. FIG. 1I shows the expression of each gene. * $p<0.025$,  $p<0.005$, * $p<0.0005$ vs. vehicle (Shirley-Williams test). # $p<0.025$, ## $p<0.005$, ### $p<0.0005$ vs. vehicle (Williams' test). Data represent mean±SD (N=6);

FIG. 2A shows GHb. FIG. 2B shows plasma glucose. FIG. 2C shows plasma insulin. FIG. 2D shows daily changes in body weight. FIG. 2E shows % inhibition of cumulative food intake. FIG. 2F shows tissue weight. FIG. 2G shows liver TG content. # $p<0.025$, ## $p<0.005$, ### $p<0.0005$ vs. vehicle (Shirley-Williams test). Data represent mean±SD (N=5 or 7). N=5 for the vehicle-administered group. N=7 for the P41-administered group;

FIG. 3A shows daily changes in body weight. FIG. 3B shows % inhibition of cumulative food intake. FIG. 3C shows ΔGHb. FIG. 3D shows plasma glucose. FIG. 3E shows plasma insulin. FIG. 3F shows liver weight. FIG. 3G shows liver TG content. FIG. 3H shows white fat weight. * $p<0.025$,  $p<0.005$, *$p<0.0005$ vs vehicle (Williams' test). # $p<0.025$, ## $p<0.005$, ### $p<0.0005$ vs vehicle (Shirley-Williams test). Data represent mean±SD (N=7);

DETAILED DESCRIPTION OF THE INVENTION

Figure 1:
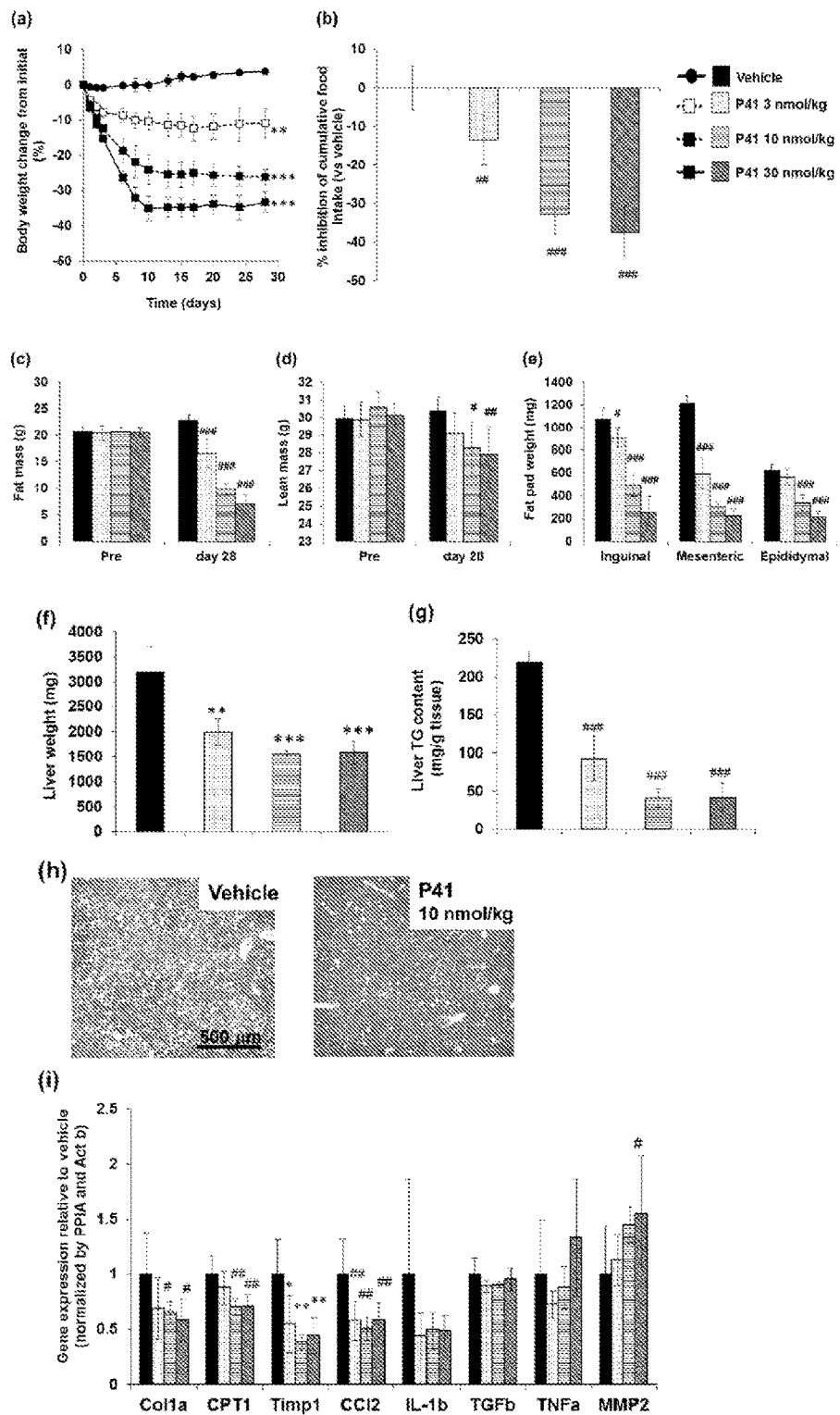
FIG. 1 shows the antiobesity action of the compound of Example 41 (P41) in DIO mice. Each compound was subcutaneously administered to each mouse once a day for 4 weeks.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),

(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, triazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

The definition of each symbol in the formula (I) is described in detail in the following.

$P^1$ is a group represented by the formula:
—$R^{41}$,
—CO—$R^{41}$,
—CO—O$R^{41}$,
—CO—CO$R^{41}$,
—SO—$R^{41}$,
—SO$_2$—$R^{41}$,
—SO$_2$—O$R^{41}$,
—CO—N$R^{42}R^{43}$,
—SO$_2$—N$R^{42}R^{43}$, or
—C(=N$R^{41}$)—N$R^{42}R^{43}$
wherein $R^{41}$, $R^{42}$ and $R^{43}$ are each independently a hydrogen atom, an optionally substituted hydrocarbon group, or optionally substituted heterocyclic group.

$P^1$ is preferably a hydrogen atom or a methyl group.

The linker-alkyl chain moiety represented by (-Gly-Gly-Gly-Gly-$R^{410}$) is bonded to the ε-amino group of 10-position Lys to assume the following structure:

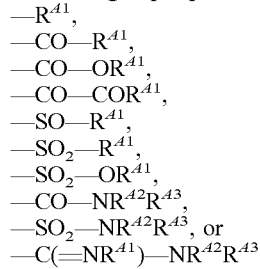

[Formula 1]

The presence of this linker-alkyl chain may achieve the durability of the action of compound (I).

$R^{410}$ is Pal or Oda.
$R^{410}$ is preferably Pal.

A11 is Aib, Ala or Ser.
A11 is preferably Aib.
In an alternative embodiment, A11 is preferably Ala.
In an alternative embodiment, A11 is preferably Ser.
A12 is Ile or Lys.
A12 is preferably Ile.
A15 is Asp or Glu.
A15 is preferably Glu.
A18 is Ala or Arg.
A18 is preferably Arg.
A35 is Tyr or Phe(2-F).
A35 is preferably Tyr.

Preferable examples of compound (I) include the following peptides or salts thereof.

[Compound A]
Compound (I) which is a peptide wherein
$P^1$ is methyl;
$R^{410}$ is Pal or Oda;
A11 is Aib, Ala or Ser (A11 is preferably Aib, is preferably Ala in an alternative embodiment, and is preferably Ser in an alternative embodiment);
A12 is Ile;
A15 is Glu;
A18 is Arg; and
A35 is Tyr,
or a salt thereof.

[Compound B]
Compound (I) which is a peptide (SEQ ID NO: 40) described in Example 31 or a salt thereof.
Compound (I) which is a peptide (SEQ ID NO: 44) described in Example 35 or a salt thereof.
Compound (I) which is a peptide (SEQ ID NO: 50) described in Example 41 or a salt thereof.

Compound (I) can be produced according to a peptide synthesis method known per se. The method of peptide synthesis may be any of, for example, a solid phase synthesis process and a liquid phase synthesis process. That is, the object peptide can be produced by repeating condensation of a partial peptide or amino acid capable of constituting compound (I) and the remaining portion (which may be constituted by two or more amino acids) according to a desired sequence. When a product having the desirable sequence has a protecting group, the object peptide can be produced by eliminating a protecting group. Examples of the condensing method and eliminating method of a protecting group to be known include methods described in the following (1)-(5).

(1) M. Bodanszky and M. A. Ondetti: Peptide Synthesis, Interscience Publishers, New York (1966)
(2) Schroeder and Luebke: The Peptide, Academic Press, New York (1965)
(3) Nobuo Izumiya, et al.: Peptide Gosei no Kiso to Jikken (Basics and experiments of peptide synthesis), published by Maruzen Co. (1975)
(4) Haruaki Yajima and Shunpei Sakakibara: Seikagaku Jikken Koza (Biochemical Experiment) 1, Tanpakushitsu no Kagaku (Chemistry of Proteins) IV, 205 (1977)
(5) Haruaki Yajima, ed.: Zoku Iyakuhin no Kaihatsu (A sequel to Development of Pharmaceuticals), Vol. 14, Peptide Synthesis, published by Hirokawa Shoten After the reaction, compound (I) can be purified and isolated using conventional methods of purification, such as solvent extraction, distillation, column chromatography, liquid chromatography, recrystallization, etc., in combination thereof. When the peptide obtained by the above-mentioned method is in a free form, it can be converted to a suitable salt by a known method; conversely, when the peptide is obtained in the form of a salt, the salt can be converted to a free form by a known method.

The starting compound may also be a salt. Examples of such salt include those exemplified as salts of compound (I) mentioned bellow.

For condensation of protected amino acid or peptide, various activation reagents usable for peptide synthesis can be used, which are particularly preferably trisphosphonium salts, tetramethyluronium salts, carbodiimides and the like. Examples of the trisphosphonium salt include benzotriazol-1-yloxytris(pyrrolizino)phosphoniumhexafluorophosphate (PyBOP), bromotris(pyrrolizino)phosphoniumhexafluorophosphate (PyBroP), 7-azabenzotriazol-1-yloxytris(pyrrolizino)phosphoniumhexafluorophosphate (PyAOP), examples of the tetramethyluronium salt include 2-(1H-benzotriazol-1-yl)-1,1,3,3-tetramethyluroniumhexafluorophosphate (HBTU), 2-(7-azabenzotriazol-1-yl)-1,1,3,3-tetramethyluroniumhexafluorophosphate (HATU), 2-(1H-benzotriazol-1-yl)-1,1,3,3-tetramethyluroniumtetrafluoroborate (TBTU), 2-(5-norbornane-2,3-dicarboxyimide)-1,1,3,3-tetramethyluroniumtetrafluoroborate (TNTU), 0-(N-succimidyl)-1,1,3,3-tetramethyluroniumtetrafluoroborate (TSTU), and examples of the carbodiimide include DCC, N,N'-diisopropylcarbodiimide (DIPCDI), N-ethyl-N'-(3-dimethylaminopropyl)carbodiimide hydrochloride (EDCI-.HCl) and the like. For condensation using these, addition of a racemization inhibitor (e.g., HONB, HOBt, HOAt, HOOBt etc.) is preferable. A solvent to be used for the condensation can be appropriately selected from those known to be usable for peptide condensation reaction. For example, acid amides such as anhydrous or water-containing N,N-dimethylformamide, N,N-dimethylacetamide, N-methylpyrrolidone and the like, halogenated hydrocarbons such as methylene chloride, chloroform and the like, alcohols such as trifluoroethanol, phenol and the like, sulfoxides such as dimethylsulfoxide and the like, tertiary amines such as pyridine and the like, ethers such as dioxane, tetrahydrofuran and the like, nitriles such as acetonitrile, propionitrile and the like, esters such as methyl acetate, ethyl acetate and the like, an appropriate mixture of these and the like can be used. Reaction temperature is appropriately selected from the range known to be usable for peptide binding reactions, and is normally selected from the range of about −20° C. to 50° C. An activated amino acid derivative is normally used from 1.5 to 6 times in excess. In phase synthesis, when a test using the ninhydrin reaction reveals that the condensation is insufficient, sufficient condensation can be conducted by repeating the condensation reaction without elimination of protecting groups. If the condensation is yet insufficient even after repeating the reaction, unreacted amino acids can be acylated with acetic anhydride, acetylimidazole or the like so that an influence on the subsequent reactions can be avoided.

Examples of the protecting groups for the amino groups of the starting amino acid include Z, Boc, tert-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, trityl and the like.

Examples of the carboxyl-protecting group for the starting amino acid include allyl, 2-adamantyl, 4-nitrobenzyl, 4-methoxybenzyl, 4-chlorobenzyl, phenacyl and benzyloxycarbonylhydrazide, tert-butoxycarbonylhydrazide, tritylhydrazide and the like, in addition to the above-mentioned $C_{1-6}$ alkyl group, $C_{3-10}$ cycloalkyl group, $C_{7-14}$ aralkyl group.

The hydroxyl group of serine or threonine can be protected, for example, by esterification or etherification. Examples of the group suitable for the esterification include lower ($C_{2-4}$) alkanoyl groups such as an acetyl group and the like, aroyl groups such as a benzoyl group and the like, and a group derived from an organic acid and the like. In addition, examples of the group suitable for etherification include benzyl, tetrahydropyranyl, tert-butyl(But), trityl (Trt) and the like.

Examples of the protecting group for the phenolic hydroxyl group of tyrosine include Bzl, 2,6-dichlorobenzyl, 2-nitrobenzyl, Br—Z, tert-butyl and the like.

Examples of the protecting group for the imidazole of histidine include Tos, 4-methoxy-2,3,6-trimethylbenzenesulfonyl (Mtr), DNP, Bom, Bum, Boc, Trt, Fmoc and the like.

Examples of the protecting group for the guanidino group of arginine include Tos, Z, 4-methoxy-2,3,6-trimethylbenzenesulfonyl (Mtr), p-methoxybenzenesulfonyl (MBS), 2,2,5,7,8-pentamethylchromane-6-sulfonyl (Pmc), mesitylene-2-sulfonyl (Mts), 2,2,4,6,7-pentamethyldihydrobenzofuran-5-sulfonyl (Pbf), Boc, Z, $NO_2$ and the like.

Examples of the protecting group for a side chain amino group of lysine include Z, Cl—Z, trifluoroacetyl, Boc, Fmoc, Trt, Mtr, 4,4-dimethyl-2,6-dioxocyclohexylideneyl (Dde) and the like.

Examples of the protecting group for indolyl of tryptophan include formyl (For), Z, Boc, Mts, Mtr and the like.

Examples of the protecting group for asparagine and glutamine include Trt, xanthyl (Xan), 4,4'-dimethoxybenzhydryl (Mbh), 2,4,6-trimethoxybenzyl (Tmob) and the like.

Examples of activated carboxyl groups in the starting material include corresponding acid anhydride, azide, active esters [ester with alcohol (e.g., pentachlorophenol, 2,4,5-trichlorophenol, 2,4-dinitrophenol, cyanomethylalcohol, paranitrophenol, HONB, N-hydroxysuccimide, 1-hydroxybenzotriazole (HOBt), 1-hydroxy-7-azabenzotriazole (HOAt))] and the like. Examples of the activated amino group in the starting material include corresponding phosphorous amide.

Examples of the method for removing (eliminating) a protecting group include a catalytic reduction in a hydrogen stream in the presence of a catalyst such as Pd-black or Pd-carbon; an acid treatment using anhydrous hydrogen fluoride, methanesulfonic acid, trifluoromethanesulfonic acid, trifluoroacetate, trimesylsilyl bromide (TMSBr), trimethylsilyl trifluoromethanesulfonate, tetrafluoroboric acid, tris(trifluoro)boric acid, boron tribromide, or a mixture solution thereof; a base treatment using diisopropylethylamine, triethylamine, piperidine, piperazine or the like; and reduction with sodium in liquid ammonia, and the like. The elimination reaction by the above-described acid treatment is generally carried out at a temperature of −20° C. to 40° C.; the acid treatment is efficiently conducted by adding a cation scavenger such as anisole, phenol, thioanisole, metacresol and paracresol; dimethylsulfide, 1,4-butanedithiol, 1,2-ethanedithiol and the like. Also, a 2,4-dinitrophenyl group used as a protecting group of the imidazole of histidine is removed by thiophenol treatment; a formyl group used as a protecting group of the indole of tryptophan is removed by deprotection by acid treatment in the presence of 1,2-ethanedithiol, 1,4-butanedithiol, or the like, as well as by alkali treatment with dilute sodium hydroxide, dilute ammonia, or the like.

Protection of a functional group that should not be involved in the reaction of a starting material and a protecting group, elimination of the protecting group, activation of a functional group involved in the reaction and the like can be appropriately selected from known protecting groups and known means.

In a method of preparing an amide of the peptide, it is formed by a solid phase synthesis using a resin for amide synthesis, or the a-carboxyl group of the carboxy terminal amino acid is amidated, and a peptide chain is elongated to a desired chain length toward the amino group side, thereafter a peptide wherein the protecting group for the N terminal α-amino group of the peptide chain only removed and a peptide wherein the protecting group for the C terminal carboxyl group only removed of the peptide chain are prepared, and the both peptides are condensed in a mixed solvent described above. For details about the condensation reaction, the same as above applies. After the protected peptide obtained by the condensation is purified, all protecting groups can be removed by the above-described method to yield a desired crude polypeptide. By purifying this crude peptide using various publicly known means of purification, and freeze-drying the main fraction, a desired amide of the peptide can be prepared.

Compound (I) can be produced, for example, by the following method: first, compound (II) in which the Lys(-Gly-Gly-Gly-Gly-$R^{410}$) moiety of compound (I) is Lys is produced by a peptide synthesis method known per se. Compound (II) may be supported by a resin. Here, the amino acids and $P^1$ constituting compound (II) are preferably protected with appropriate protecting groups so as not to adversely influence the production of compound (I). Examples of the protecting groups include protecting groups used in Reference Examples and Examples mentioned later. Lys in the compound (II) is protected at its side chain amino group with an orthogonal protecting group (e.g., ivDde; in the present specification, (1-(4,4-dimethyl-2,6-dioxocyclohex-1-ylidene)-3-methylbutyl) is to be sometimes abbreviated to ivDde). Subsequently, the orthogonal protecting group of Lys in compound (II) is removed under selective conditions, and amino acids corresponding to (-Gly-Gly-Gly-Gly-H) are successively condensed by a method known per se to give compound (III). Compound (III) may be supported by a resin.

(SEQ ID NO: 1)
$P^1$-Tyr-Aib-Glu-Gly-Thr-α-MePhe-Thr-Ser-Asp-Tyr-

Aib-Lys-Aib-Leu-Asp-A16-A17-Ala-A19-Ala-Glu-Phe-

Val-A24-Trp-Leu-Leu-A28-Gly (II)

wherein each symbol is as defined above.

(SEQ ID NO: 1)
$P^1$-Tyr-Aib-Glu-Gly-Thr-α-MePhe-Thr-Ser-Asp-Tyr-

Aib-Lys(-Gly-Gly-Gly-Gly-H)-Aib-Leu-Asp-A16-A17-

Ala-A19-Ala-Glu-Phe-Val-A24-Trp-Leu-Leu-A28-Gly (III)

wherein each symbol is as defined above.

The amino acids and $P^1$ constituting compound (III), as with compound (II), are preferably protected with appropriate protecting groups.

Compound (III) is condensed with compound (IV) by a method known per se, and all protecting groups are removed to give compound (I) (in some cases, by cleavage from a resin). $R^{410}$ constituting compound (IV), as with compounds (II) and (III), is preferably protected with an appropriate protecting group (hereinafter sometimes to be abbreviated as P).

$$HO-R^{410} \qquad (IV)$$

wherein $R^{410}$ is Oda or Pal.

Examples of the protecting group represented by P include the above-mentioned protecting group for the carboxyl group (preferably tert-butyl). For example, a commercially available product can be used as compound (IV).

Compound (I) can also be produced by successively condensing fragment peptides produced by a method similar to the above-mentioned method, by a method known per se. The amino acids and $P^1$ constituting the fragment peptides, as with compound (II), may be protected with appropriate protecting groups. Also, the fragment peptides may be supported by resins.

When the compound (I) is present as a configurational isomer such as enantiomer, diastereomer etc., a conformer or the like, they are also encompassed in compound (I) and each can be isolated by a means known per se or the above separation and purification methods on demand. In addition, when the compound (I) is in the form of a racemate, it can be separated into S- and R-forms by conventional optical resolution.

When the compound (I) includes stereoisomers, both the isomers alone and mixtures of each isomers are also encompassed in compound (I).

Compound (I) can be chemically modified according to a method known per se and using polyethylene glycol. For example, chemically modified compound (I) can be produced by conjugatedly binding polyethylene glycol to Cys residue, Asp residue, Glu residue, Lys residue and the like of compound (I). Also, a linker structure may be present between compound (I) and polyethylene glycol.

Compound (I) modified by polyethylene glycol (PEG) may produce, for example, the effects of promoting the biological activity, prolonging the blood circulation time, reducing the immunogenicity, enhancing the solubility, and enhancing the resistance to metabolism, of a therapeutically and diagnostically important peptide.

The molecular weight of PEG is not particularly limited and is normally about 1 K to about 1000 K daltons, preferably about 10 K to about 100 K daltons, more preferably about 20 K to about 60 K daltons.

A method well known in the art can be used as a method for modifying compound (I) by PEG, and, for example, the methods described below can be used.

(1) A PEGylating reagent having an active ester (e.g., SUNBRIGHT MEGC-30TS (trade name), NOF Corp.) is bound to the amino group of compound (I).

(2) A PEGylating reagent having an aldehyde (e.g., SUNBRIGHT ME-300AL (trade name), NOF Corp.) is bound to the amino group of compound (I).

(3) A divalent cross-linking reagent (e.g., GMBS (Dojindo Laboratories), EMCS (Dojindo Laboratories), KMUS (Dojindo Laboratories), SMCC (Pierce)) is bound to compound (I), to which a PEGylating reagent having a thiol group (e.g., SUNBRIGHT ME-300-SH (trade name), NOF Corp.) is then bound.

(4) A thiol group is introduced to compound (I) using an SH introducing agent (e.g., D-cysteine residue, L-cysteine residue, Traut's reagent), and this thiol group is reacted with a PEGylating reagent having a maleimide group (e.g., SUNBRIGHT ME-300MA (trade name), NOF Corp.).

(5) A thiol group is introduced to compound (I) using an SH introducing agent (e.g., D-cysteine residue, L-cysteine residue, Traut's reagent), and this thiol group is reacted with a PEGylating reagent having an iodoacetamide group (e.g., SUNBRIGHT ME-300IA (trade name), NOF Corp.).

(6) A ω-aminocarboxylic acid, an α-amino acid or the like is introduced as a linker to the N-terminal amino group of compound (I), and an amino group derived from this linker is reacted with a PEGylating reagent having an active ester (e.g., SUNBRIGHT MEGC-30TS (trade name), NOF Corp.).

(7) A ω-aminocarboxylic acid, an α-amino acid or the like is introduced as a linker to the N-terminal amino group of compound (I), and an amino group derived from this linker is reacted with a PEGylating reagent having an aldehyde group (e.g., SUNBRIGHT ME-300AL (trade name), NOF Corp.).

In addition, the compound (I) may be a solvate (e.g., hydrate) or a non-solvate (e.g., non-hydrate).

The compound (I) may be labeled with an isotope (e.g., $^3$H, $^{14}$C, $^{33}$S, $^{125}$I) or the like.

Furthermore, compound (I) may be a deuterium conversion form wherein $^1$H is converted to $^2$H(D).

Compound (I) labeled or substituted with an isotope can be used as, for example, a tracer (PET tracer) for use in Positron Emission Tomography (PET), and may be useful in the fields of medical diagnosis and the like.

For the peptides mentioned herein, the left end is the N terminal (amino terminal) and the right end is the C terminal (carboxyl terminal) in accordance with the conventional peptide marking. The C terminal of peptide may be any of an amide (—CONH$_2$), a carboxyl group (—COOH), a carboxylate (—COO$^-$), an alkylamide (—CONHR$^a$), and an ester (—COOR$^a$). Particularly, amide (—CONH$_2$) is preferable.

Compound (I) may be in a salt form. Examples of such salt include metal salts, ammonium salts, salts with organic base, salts with inorganic acid, salts with organic acid, salts with basic or acidic amino acid, and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like. Preferable examples of the salt with acidic amino acid include salts with aspartic acid, glutamic acid and the like.

Among the above-mentioned salts, a pharmaceutically acceptable salt is preferable. For example, when a compound has an acidic functional group, an inorganic salt such as alkali metal salt (e.g., sodium salt, potassium salt etc.), alkaline earth metal salt (e.g., calcium salt, magnesium salt, barium salt etc.) and the like, ammonium salt etc., and when a compound has a basic functional group, for example, a salt with inorganic acid such as hydrochloric acid, hydrobromic acid, nitric acid, sulfuric acid, phosphoric acid and the like, or a salt with organic acid such as acetic acid, phthalic acid, fumaric acid, oxalic acid, tartaric acid, maleic acid, citric acid, succinic acid, methanesulfonic acid, p-toluenesulfonic acid and the like are preferable.

Compound (I) may be in a prodrug form.

A prodrug means a compound which is converted to compound (I) with a reaction due to an enzyme, gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

Examples of a prodrug of compound (I) include a compound wherein an amino of compound (I) is acylated, alkylated or phosphorylated (e.g., compound wherein amino of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated, and the like); a compound wherein a hydroxy of compound (I) is acylated, alkylated, phosphorylated or borated (e.g., a compound wherein a hydroxy of compound (I) is acetylated, palmitoylated, propanoylated, pivaloylated, succinylated, fumarylated, alanylated or dimethylaminomethylcarbonylated); a compound wherein a carboxy of compound (I) is esterified or amidated (e.g., a compound wherein a carboxy of compound (I) is $C_{1-6}$ alkyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated) and the like. Among others, a compound wherein carboxy of compound (I) is esterified with $C_{1-6}$ alkyl such as methyl, ethyl, tert-butyl or the like is preferably used. These compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

In the present specification, the prodrug may form a salt. Examples of such a salt include those exemplified as the salt of compound (I).

Compound (I) may be a crystal. Crystals having a singular crystal form or a mixture of plural crystal forms are also included in compound (I). Crystals can be produced by crystallizing compound (I) according to a crystallization method known per se.

In addition, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization known per se.

The crystal of compound (I) may be superior in physicochemical properties (e.g., melting point, solubility, stability) and biological properties (e.g., pharmacokinetics (absorption, distribution, metabolism, excretion), efficacy expression), and thus it may be extremely useful as a medicament.

Compound (I) and a prodrug thereof (hereinafter to be sometimes abbreviated as the compound of the present invention) may have an activating action on Y2 receptors, GLP-1 receptors and GIP receptors.

The compound of the present invention may have a high activating action on Y2 receptors, GLP-1 receptors and GIP receptors, particularly, in vivo.

Since Y2 receptors have a feeding suppressive action, the peptide having a Y2 receptor-activating action may be useful in the prophylaxis or treatment of symptoms associated with eating disorder, including obesity and diabetes. GLP-1 and GIP are gut hormones called incretin, and have the action of promoting insulin secretion from the pancreas. Since incretin is closely related to glucose metabolism, the compound having an activating action on GLP-1 receptors and GIP receptors may be useful in the prophylaxis or treatment of symptoms associated with glucose metabolism disorder, including diabetes and obesity.

Thus, the compound of the present invention may have a feeding suppressive action, a body weight-lowering action and the like.

The compound of the present invention has high biological and chemical stability, and may be expected to have the durability of its effect in vivo.

GLP-1 receptor agonists are clinically known to have nausea and emesis as side effects. The compound of the present invention may reduce such an emetic action as compared to GLP-1 receptor agonists.

The compound of the present invention may be used as an activator of a Y2 receptor, a GLP-1 receptor and a GIP receptor.

In the present invention, the activator of a Y2 receptor, a GLP-1 receptor and a GIP receptor means an agent having a Y2 receptor-activating action (Y2 receptor agonist action), a GLP-1 receptor-activating action (GLP-1 receptor agonist action) and a GIP receptor-activating action (GIP receptor agonist action).

The compound of the present invention has low toxicity (e.g., acute toxicity, chronic toxicity, genetic toxicity, reproductive toxicity, cardiac toxicity, carcinogenicity), shows a few side effects, and can be safely administered to a mammal (e.g., human, bovine, horse, dog, cat, monkey, mouse, rat) as an agent for the prophylaxis or treatment of various diseases mentioned below and the like.

The compound of the present invention may be used as an agent for the treatment or prophylaxis of various diseases including diabetes and obesity, by virtue of the above-mentioned activating action on GLP-1 receptors and GIP receptors. The compound of the present invention may be used as an agent for the prophylaxis or treatment of, for example, symptomatic obesity, obesity based on simple obesity, disease state or disease associated with obesity, eating disorder, diabetes (e.g., type 1 diabetes, type 2 diabetes, gestational diabetes, obese diabetes), hyperlipidemia (e.g., hypertriglyceridemia, hypercholesterolemia, high LDL-cholesterolemia, low HDL-cholesterolemia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (disease states having 3 or more selected from hypertriglycerid(TG)emia, low HDL cholesterol(HDL-C)emia, hypertension, abdominal obesity and impaired glucose tolerance), sarcopenia and the like.

Examples of the symptomatic obesity include endocrine obesity (e.g., Cushing syndrome, hypothyroidism, insulinoma, obese type II diabetes, pseudohypoparathyroidism, hypogonadism), central obesity (e.g., hypothalamic obesity, frontal lobe syndrome, Kleine-Levin syndrome), hereditary obesity (e.g., Prader-Willi syndrome, Laurence-Moon-Biedl syndrome), drug-induced obesity (e.g., steroid, phenothiazine, insulin, sulfonylurea (SU) agent, β-blocker-induced obesity) and the like.

Examples of the disease state or disease associated with obesity include glucose tolerance disorders, diabetes (particularly type 2 diabetes, obese diabetes), lipid metabolism abnormality (synonymous with the above-mentioned hyperlipidemia), hypertension, cardiac failure, hyperuricemia/gout, fatty liver (including non-alcoholic steato-hepatitis), coronary heart disease (myocardial infarction, angina pectoris), cerebral infarction (brain thrombosis, transient cerebral ischemic attack), bone/articular disease (knee osteoarthritis, hip osteoarthritis, spondylitis deformans, lumbago), sleep apnea syndrome/Pickwick syndrome, menstrual disorder (abnormal menstrual cycle, abnormality of menstrual flow and cycle, amenorrhea, abnormal catamenial symptom), metabolic syndrome and the like.

New diagnostic criteria were reported by The Japan Diabetes Society in 1999 about the diagnostic criteria of diabetes.

According to this report, diabetes refers to a state that meets any of a fasting blood glucose level (glucose concentration in venous plasma) of 126 mg/dl or more, a 2-hr value (glucose concentration in venous plasma) of 200 mg/dl or more in the 75 g oral glucose tolerance test (75 g OGTT), and a casual blood glucose level (glucose concentration in venous plasma) of 200 mg/dl or more. Also, a state that does not apply to the above-mentioned diabetes, and is not a state exhibiting "a fasting blood glucose level (glucose concentration in venous plasma) less than 110 mg/dl or a 2-hr value (glucose concentration in venous plasma) less than 140 mg/dl in the 75 g oral glucose tolerance test (75 g OGTT)" (normal type) is called "borderline type".

Moreover, new diagnostic criteria were reported by American Diabetes Association (ADA) in 1997 and by World Health Organization (WHO) in 1998 about the diagnostic criteria of diabetes.

According to these reports, diabetes refers to a state that meets a fasting blood glucose level (glucose concentration in venous plasma) of 126 mg/dl or more and a 2-hr value (glucose concentration in venous plasma) of 200 mg/dl or more in the 75 g oral glucose tolerance test.

According to the above-mentioned reports, impaired glucose tolerance refers to a state that meets a fasting blood glucose level (glucose concentration in venous plasma) less than 126 mg/dl and a 2-hr value (glucose concentration in venous plasma) of 140 mg/dl or more and less than 200 mg/dl in the 75 g oral glucose tolerance test. According to the report of ADA, a state exhibiting a fasting blood glucose level (glucose concentration in venous plasma) of 110 mg/dl or more and less than 126 mg/dl is called IFG (Impaired Fasting Glucose). On the other hand, according to the report of WHO, a state of the IFG (Impaired Fasting Glucose) exhibiting a 2-hr value (glucose concentration in venous plasma) less than 140 mg/dl in the 75 g oral glucose tolerance test is called IFG (Impaired Fasting Glycemia).

The compound of the present invention may also be used as an agent for the prophylaxis or treatment of diabetes determined according to the above-mentioned new diagnostic criteria, borderline type diabetes, impaired glucose tolerance, IFG (Impaired Fasting Glucose) and IFG (Impaired Fasting Glycemia). Moreover, the compound of the present invention may prevent progress of borderline type, impaired glucose tolerance, IFG (Impaired Fasting Glucose) or IFG (Impaired Fasting Glycemia) into diabetes.

The compound of the present invention may be used as a body weight-lowering agent for mammals based on a body weight-lowering action. A mammal that is subject to the application of the compound of the present invention can be a mammal desired to decrease weight. The mammal may be a mammal having a genetic risk of overweight, or may be a mammal affected by lifestyle-related disease such as diabetes, hypertension and/or hyperlipidemia. The overweight may be attributed to excessive died ingestion or unbalanced diets, or may be overweight derived from a concomitant drug (e.g., insulin sensitizers having a PPARγ agonist-like action, such as troglitazone, rosiglitazone, englitazone, ciglitazone, pioglitazone and the like). Alternatively, the overweight may be overweight before reaching obesity, or may be overweight in obesity patients. Here, obesity is defined as a body mass index (BMI: body weight $(kg) \pm [\text{height }(m)]^2$) of 25 or more (according to the criteria of Japan Society for the Study of Obesity) for Japanese and as BMI of 30 or more (according to the criteria of WHO) for Western people.

The compound of the present invention may also be useful as an agent for the prophylaxis or treatment of metabolic syndrome. The incidence of cardiovascular disease is significantly high in metabolic syndrome patients, compared with patients with a single lifestyle-related disease. Thus, the prophylaxis or treatment of metabolic syndrome is exceedingly important for preventing cardiovascular disease.

The diagnostic criteria of metabolic syndrome were announced by WHO in 1999 and by NCEP in 2001. According to the diagnostic criteria of WHO, an individual having hyperinsulinemia or abnormal glucose tolerance as a requirement and two or more of visceral obesity, dyslipidemia (high TG or low HDL) and hypertension is diagnosed as having metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the diagnostic criteria of the Adult Treatment Panel III of the National Cholesterol Education Program (guideline of ischemic heart disease) in USA, an individual having three or more of visceral obesity, hypertriglyceridemia, low HDL-cholesterolemia, hypertension and abnormal glucose tolerance is diagnosed as having metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention may also be used as an agent for the prophylaxis or treatment of, for example, osteoporosis, cachexia (e.g., cancerous cachexia, tuberculous cachexia, diabetic cachexia, cachexia associated with blood disease, cachexia associated with endocrine disease, cachexia associated with infectious disease or cachexia caused by acquired immunodeficiency syndrome), fatty liver, polycystic ovary syndrome, renal disease (e.g., chronic renal failure, diabetic nephropathy, glomerulonephritis, glomerulosclerosis, Nephrotic syndrome, hypertensive nephrosclerosis, end-stage renal disease), muscular dystrophy, myocardial infarction, angina pectoris, cerebrovascular disorder (e.g., cerebral infarction, stroke), Alzheimer's disease, Parkinson's disease, anxiety, dementia, insulin resistant syndrome, syndrome X, hyperinsulinemia, paresthesia caused by hyperinsulinemia, acute or chronic diarrhea, inflammatory disease (e.g., chronic rheumatoid arthritis, spondylitis deformans, arthritis deformans, lumbago, gout, post-operational or post-traumatic inflammation, bloating, neuralgia, laryngopharyngitis, cystitis, hepatitis (including non-alcoholic steatohepatitis), pneumonia, pancreatitis, enteritis, inflammatory bowel disease (including inflammatory large bowel disease), colitis ulcerosa, gastric mucosal injury (including gastric mucosal injury caused by aspirin)), small intestinal mucosal injury, malabsorption, testicular dysfunction, visceral obesity syndrome and sarcopenia.

Moreover, the compound of the present invention may also be used as an agent for the prophylaxis or treatment of various cancers (particularly, breast cancer (e.g., invasive ductal breast cancer, noninvasive ductal breast cancer, inflammatory breast cancer, etc.), prostate cancer (e.g., hormone-dependent prostate cancer, hormone-independent prostate cancer, etc.), pancreatic cancer (e.g., ductal pancreatic cancer, etc.), gastric cancer (e.g., papillary adenocarcinoma, mucous adenocarcinoma, adenosquamous carcinoma, etc.), lung cancer (e.g., non-small cell lung cancer, small-cell lung cancer, malignant mesothelioma, etc.), colon cancer (e.g., gastrointestinal stromal tumor, etc.), rectal cancer (e.g., gastrointestinal stromal tumor, etc.), colorectal cancer (e.g., familial colorectal cancer, hereditary non-polyposis colorectal cancer, gastrointestinal stromal tumor, etc.), small intestinal cancer (e.g., non-Hodgkin's lymphoma, gastrointestinal stromal tumor, etc.), esophageal cancer, duodenal cancer, tongue cancer, pharyngeal cancer (e.g., nasopharyngeal cancer, oropharynx cancer, hypopharyngeal cancer, etc.), salivary gland cancer, brain tumor (e.g., pineal astrocytoma, pilocytic astrocytoma, diffuse astrocytoma, anaplastic astrocytoma, etc.), neurilemmoma, liver cancer (e.g., primary liver cancer, extrahepatic bile duct cancer, etc.), renal cancer (e.g., renal cell cancer, transitional cell cancer of the renal pelvis and ureter, etc.), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential, etc.), bladder cancer, urethral cancer, skin cancer (e.g., intraocular (ocular) melanoma, Merkel cell carcinoma, etc.), hemangioma, malignant lymphoma, malignant melanoma, thyroid cancer (e.g., medullary thyroid cancer, etc.), parathyroid cancer, nasal cavity cancer, sinus cancer, bone tumor (e.g., osteosarcoma, Ewing tumor, uterine sarcoma, soft tissue sarcoma, etc.), angiofibroma, sarcoma of the retina, penis cancer, testicular tumor, pediatric solid tumor (e.g., Wilms' tumor, childhood kidney tumor, etc.), Kaposi's sarcoma, Kaposi's sarcoma caused by AIDS, tumor of maxillary sinus, fibrous histiocytoma, leiomyosarcoma, rhabdomyosarcoma, leukemia (e.g., acute myeloid leukemia, acute lymphoblastic leukemia, etc.), etc.).

The compound of the present invention may also be used for secondary prevention or suppression of progression of the above-mentioned various diseases (e.g., cardiovascular events such as myocardial infarction and the like). In addition, the compound of the present invention may also be useful as a feeding suppressant and a body weight-lowering agent. The compound of the present invention may also be used in combination with a diet therapy (e.g., diet therapy for diabetes), and an exercise therapy.

A medicament containing the compound of the present invention shows low toxicity and is obtained using the compound of the present invention alone or in admixture with a pharmacologically acceptable carrier according to a method known per se (e.g., the method described in the Japanese Pharmacopoeia) generally used as production methods of pharmaceutical preparations, and may be safely administered orally or parenterally (e.g., topically, rectally, intravenously administered) as a pharmaceutical preparation, for example, tablets (inclusive of sugar-coated tablets, film-coated tablets, sublingual tablets, orally disintegrating tablets), powders, granules, capsules (inclusive of soft capsules, microcapsules), liquids, troches, syrups, emulsions, suspensions, injections (e.g., subcutaneous injections, intravenous injections, intramuscular injections, intraperitoneal injections etc.), external preparations (e.g., transnasal preparations, dermal preparations, ointments), suppository (e.g., rectal suppositories, vaginal suppositories), pellets, nasal preparations, pulmonary preparations (inhalants), transfusions and the like.

These preparations may be controlled release preparations such as a rapid release preparation, a sustained release preparation and the like (e.g., a sustained release microcapsule).

The content of the compound of the present invention in a pharmaceutical preparation is about 0.01-about 100 wt % of the whole preparation.

The above-mentioned pharmaceutically acceptable carrier may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Further, if necessary, general additives such as preservative, antioxidant, colorant, sweetening agent, adsorbing agent, wetting agent and the like may also be used appropriately in a suitable amount.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, sucrose, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoic acid esters, chlorobutanol, benzyl alcohol, phenethyl alcohol, dehydroacetic acid, sorbic acid and the like.

Examples of the antioxidant include sulfites, ascorbic acid, a-tocopherol and the like.

Examples of the colorant include water-soluble Food coal tar dyes (e.g., Food dyes such as Food Red No. 2 and No. 3, Food Yellow No. 4 and No. 5, Food Blue No. 1 and No. 2, and the like), water-insoluble lake dyes (e.g., aluminum salts of the aforementioned water-soluble Food coal tar dyes), natural dyes (e.g., β-carotene, chlorophyll, ferric oxide red) and the like.

Examples of the sweetening agent include saccharin sodium, dipotassium glycyrrhizinate, aspartame, stevia and the like.

Examples of the adsorbent include porous starch, calcium silicate (trade name: Florite RE), magnesium alumino metasilicate (trade name: Neusilin) and light anhydrous silicic acid (trade name: Sylysia).

Examples of the wetting agent include propylene glycol monostearate, sorbitan monooleate, diethylene glycol monolaurate and polyoxyethylenelauryl ether.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The dosage of the compound of the present invention is appropriately determined according to the subject of administration, symptom, administration method and the like. For example, when the compound of the present invention is administered orally to an obesity or diabetes patient (body weight 60 kg), the daily dose of the compound of the present invention is about 0.1 to 100 mg, preferably about 1.0 to 50 mg, more preferably about 1.0 to 20 mg. When the compound of the present invention is administered parenterally to an obesity or diabetes patient (body weight 60 kg), the daily dose of the compound of the present invention is about 0.001 to 30 mg, preferably about 0.01 to 20 mg, more preferably about 0.1 to 10 mg. These amounts may be administered in about 1 to several portions a day.

The compound of the present invention may be administered, for example, every 2 days, every 3 days, every 4 days, every 5 days, every 6 days, every week, twice a week, every other week, every 3 weeks, every month, every 2 months, every 3 months, every 4 months, every 5 months or every 6 months.

The compound of the present invention may be used in combination with other drug that does not adversely influence the compound of the present invention, for the purpose of, for example, promoting the action (treatment of effect for obesity, diabetes and the like) of the compound of the present invention, reducing the dose of the compound of the present invention, and the like.

Examples of a drug that can be used in combination with the compound of the present invention (hereinafter sometimes to be abbreviated as a concomitant drug) include antiobesity agents, therapeutic agents for diabetes, therapeutic agents for diabetic complications, therapeutic agents for hyperlipidemia, antihypertensive agents, diuretics, chemotherapeutics, immunotherapeutics, anti-inflammatory drugs, antithrombotic agents, therapeutic agents for osteoporosis, vitamins, antidementia drugs, erectile dysfunction drugs, therapeutic drugs for urinary frequency or urinary incontinence, therapeutic agents for dysuria and the like. Specific examples of the concomitant drug include those mentioned below.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor modulator, GABA modulator (e.g., topiramate), neuropeptide Y antagonists (e.g., velneperit), cannabinoid receptor antagonists (e.g., rimonabant, taranabant), ghrelin antagonists, ghrelin receptor antagonists, ghrelinacylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFκ inhibitory (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821, MBX-2982, APD597), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine or swine; human FGF21 preparations genetically synthesized using *Escherichia coli* or yeast; fragments or derivatives of FGF21), anorexigenic agents (e.g., P-57) and the like.

Here, as the therapeutic agent for diabetes, for example, insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably, hydrochloride), rosiglitazone or a salt thereof (preferably, maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 or WO2008/099794), a-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof), dipeptidyl peptidase IV inhibitors (e.g., Alogliptin or a salt thereof (preferably, benzoate), Vildagliptin, Sitagliptin, Saxagliptin, Bl1356, GRC8200, MP-513, PF-00734200, PHX1149, SK-0403, ALS2-0426, TA-6666, TS-021, KRP-104, Trelagliptin or a salt thereof (preferably succinate)), β3 agonists (e.g., N-5984), GPR40 agonists (e.g., Fasiglifam or a hydrate thereof, compound described in WO2004/041266, WO2004/106276, WO2005/063729, WO2005/063725, WO2005/087710, WO2005/095338, WO2007/013689 or WO2008/001931), SGLT2 (sodium-glucose cotransporter 2) inhibitors (e.g., Dapagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or agonist thereof, IKK inhibitors (e.g., AS-2868), leptin resistance improving drugs, somatostatin receptor agonists, glucokinase activators (e.g., Piragliatin, AZD1656, AZD6370, TTP-355, compound described in WO2006/112549, WO2007/028135, WO2008/047821, WO2008/050821, WO2008/136428 or WO2008/156757), GPR119 agonists (e.g., PSN821, MBX-2982, APD597), FGF21, FGF analogue, ACC2 inhibitors and the like can be mentioned.

As the therapeutic agent for diabetic complications, aldose reductase inhibitors (e.g., tolrestat, epalrestat, zopolrestat, fidarestat, CT-112, ranirestat (AS-3201), lidorestat), neurotrophic factor and increasing agents thereof (e.g., NGF, NT-3, BDNF, neurotrophic production/secretion promoting agent described in WO01/14372 (e.g., 4-(4-chlorophenyl)-2-(2-methyl-1-imidazolyl)-5-[3-(2-methylphenoxy)propyl]oxazole), compound described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitors and the like can be mentioned.

As the therapeutic agent for hyperlipidemia, HMG-COA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resin (e.g., colestyramine), probucol, nicotinic acid drugs (e.g., nicomol, niceritrol, niaspan), ethyl icosapentate, phytosterol (e.g., soysterol, gamma oryzanol (γ-oryzanol)), cholesterol absorption inhibitors (e.g., zechia), CETP inhibitors (e.g., dalcetrapib, anacetrapib), ω-3 fatty acid preparations (e.g., ω-3-fatty acid ethyl esters 90 (ω-3-acid ethyl esters 90)) and the like can be mentioned.

Examples of the antihypertensive agent include angiotensin converting enzyme inhibitors (e.g., captopril, enalapril, delapril, etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil, etc.), calcium antagonists (e.g., manidipine, nifedipine, amlodipine, efonidipine, nicardipine, cilnidipine, etc.), β blockers (e.g., metoprolol, atenolol, propranolol, carvedilol, pindolol, etc.), clonidine and the like.

As the diuretic, for example, xanthine derivatives (e.g., theobromine sodium salicylate, theobromine calcium salicylate and the like), thiazide preparations (e.g., ethiazide, cyclopenthiazide, trichloromethiazide, hydrochlorothiazide, hydroflumethiazide, benzylhydrochlorothiazide, penfluthiazide, poly5thiazide, methyclothiazide and the like), antialdosterone preparations (e.g., spironolactone, triamterene and the like), carbonic anhydrase inhibitors (e.g., acetazolamide and the like), chlorobenzenesulfonamide agents (e.g., chlortalidone, mefruside, indapamide and the like), azosemide, isosorbide, ethacrynic acid, piretanide, bumetanide, furosemide and the like can be mentioned.

Examples of the chemotherapeutic include alkylating agents (e.g., cyclophosphamide, ifosfamide), antimetabolites (e.g., methotrexate, 5-fluorouracil), anticancer antibiotics (e.g., mitomycin, adriamycin), plant-derived anticancer agents (e.g., vincristine, vindesine, Taxol), cisplatin, carboplatin, etoposide and the like. Among others, a 5-fluorouracil derivative Furtulon or Neofurtulon or the like is preferable.

Examples of the immunotherapeutic include microbial or bacterial components (e.g., muramyl dipeptide derivative, Picibanil), polysaccharides having immunoenhancing activity (e.g., lentinan, sizofiran, Krestin), cytokines obtained by genetic engineering approaches (e.g., interferon, interleukin (IL)), colony-stimulating factors (e.g., granulocyte colony-stimulating factor, erythropoietin) and the like. Among others, interleukins such as IL-1, IL-2, IL-12 and the like are preferable.

Examples of the anti-inflammatory drug include non-steroidal anti-inflammatory drugs such as aspirin, acetaminophen, indomethacin and the like.

As the antithrombotic agent, for example, heparin (e.g., heparin sodium, heparin calcium, enoxaparin sodium, dalteparin sodium), warfarin (e.g., warfarin potassium), anti-thrombin drugs (e.g., aragatroban, dabigatran), FXa inhibitors (e.g., rivaroxaban, apixaban, edoxaban, YM150, compound described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like can be mentioned.

Examples of the therapeutic agent for osteoporosis include alfacalcidol, calcitriol, elcatonin, calcitonin salmon, estriol, ipriflavone, pamidronate disodium, alendronate sodium hydrate, incadronate disodium, risedronate disodium and the like.

Examples of the vitamin include vitamin $B_1$, vitamin $B_{12}$ and the like.

Examples of the antidementia drug include tacrine, donepezil, rivastigmine, galanthamine and the like.

Examples of the erectile dysfunction drug include apomorphine, sildenafil citrate and the like.

Examples of the therapeutic drug for urinary frequency or urinary incontinence include flavoxate hydrochloride, oxybutynin hydrochloride, propiverine hydrochloride and the like.

Examples of the therapeutic agent for dysuria include acetylcholine esterase inhibitors (e.g., distigmine) and the like.

Moreover, a drug confirmed to have a cachexia-ameliorating action either in animal models or clinically, i.e., a cyclooxygenase inhibitor (e.g., indomethacin), a progesterone derivative (e.g., megestrol acetate), glucocorticoid (e.g., dexamethasone), a metoclopramide drug, a tetrahydrocannabinol drug, an agent for improving fat metabolism (e.g., eicosapentaenoic acid), growth hormone, IGF-1, or an antibody against a cachexia-inducing factor TNF-α, LIF, IL-6 or oncostatin M or the like may also be used in combination with the compound of the present invention.

Alternatively, a glycation inhibitor (e.g., ALT-711), a nerve regeneration-promoting drug (e.g., Y-128, VX853, prosaptide), an antidepressant (e.g., desipramine, amitriptyline, imipramine), an antiepileptic drug (e.g., lamotrigine, Trileptal, Keppra, Zonegran, Pregabalin, Harkoseride, carbamazepine), an antiarrhythmic drug (e.g., mexiletine), an acetylcholine receptor ligand (e.g., ABT-594), an endothelin receptor antagonist (e.g., ABT-627), a monoamine uptake inhibitor (e.g., tramadol), a narcotic analgesic (e.g., morphine), a GABA receptor agonist (e.g., gabapentin, MR preparation of gabapentin), an α2 receptor agonist (e.g., clonidine), a local analgesic (e.g., capsaicin), an antianxiety drug (e.g., benzothiazepine), a phosphodiesterase inhibitor (e.g., sildenafil), a dopamine receptor agonist (e.g., apomorphine), midazolam, ketoconazole or the like may be used in combination with the compound of the present invention.

The time of administration of the compound of the present invention and that of the concomitant drug are not limited, and they may be administered simultaneously or in a staggered manner to the administration subject.

Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, symptom, administration method, target disease, combination and the like. When the subject of administration is human, for example, a concomitant drug can be used in 0.01-100 parts by weight relative to 1 part by weight of the compound of the present invention.

By combining the compound of the present invention and a concomitant drug:
(1) the dose of the compound of the present invention or a concomitant drug may be reduced as compared to single administration of the compound of the present invention or a concomitant drug,
(2) the drug to be used in combination with the compound of the present invention may be selected depending on the condition of patients (mild, severe and the like),
(3) the period of treatment may be set longer by selecting a concomitant drug having different action and mechanism from those of the compound of the present invention,
(4) a sustained treatment effect may be designed by selecting a concomitant drug having different action and mechanism from those of the compound of the present invention, and
(5) a synergistic effect may be afforded by a combined use of the compound of the present invention and a concomitant drug.

EXAMPLES

The abbreviations used in the present specification mean the following (Table 1-1, Table 1-2 and Table 1-3). A hyphen in terms such as α-MePhe and the like as described herein may be omitted, and the event of omission also represents the same meaning.

The amino acid sequences used in the present specification represent the N terminal on the left and the C terminal on the right.

TABLE 1-1

| | |
|---|---|
| Aad | 2-Aminoadipic acid |
| Abu | 2-Aminobutanoic acid |
| Abz(2) | 2-Aminobenzoic acid |
| Ac | Acetyl |
| Acp | 6-Aminocaproic acid |
| Acpc | 1-Aminocyclopropanecarboxylic acid |
| Adc(12) | 12-Aminododecanoic acid |
| Aib | α-Aminoisobutanoic acid |
| Aipe | 3-Aminobutanoic acid |
| Ala(4Pip) | 4-Piperidinylalanine |
| Ala(cPr) | Cyclopropylalanine |
| Alb | Albizziin 2-amino-3-ureidopropionic acid |
| Ambz(4) | 4-Aminomethylbenzoyl |
| Aoc(8) | 8-Aminocaprylic acid |
| Arg(Me) | Nω-Methylarginine |
| Asn(Me) | Nω-Methylasparagine |
| Aze(2) | Azetidine-2-carboxylic acid |
| Aze(3) | Azetidine-3-carboxylic acid |
| CC(Acp) | 6-Carboxypentylcarbamoyl |
| CC(β-Ala) | 2-Carboxyethylcarbamoyl |
| CC(GABA) | 3-Carboxypropylcarbamoyl |
| CC(Gly) | Carboxymethylcarbamoyl |
| CC(Leu) | [(1S)-1-Carboxy-3-methylbutyl]carbamoyl |
| CC(Ser) | [(1S)-1-Carboxy-2-hydroxyethyl]carbamoyl |
| CC(Tyr) | [(1S)-1-Carboxy-2-(4-hydroxyphenyl)ethyl]carbamoyl |
| Cha | Cyclohexylalanine |
| cisHyp | cis-4-Hydroxyproline |
| Cit | Citrulline |
| Dab | 2,4-Diaminobutanoic acid |
| Dap | 2,3-Diaminopropionic acid |
| GABA | γ-Aminobutanoic acid |
| Gly(cPr) | Cyclopropylglycine |
| Gly-ψ[(E)CH=CH]-Leu | which represents that the —CONH— bond between Gly and Leu is substituted by (E)-alkene |
| Har | Homoarginine |
| homoLeu | Homoleucine |
| Hse | Homoserine |
| Hyp | trans-4-Hydroxyproline |
| Iva | Isovaline |
| ivDde | 1-(4,4-Dimethyl-2,6-dioxocyclohex-1-ylidene)-3-methylbutyl |
| Iva | Isovaline, 2-amino-2-methylbutanoic acid |
| Leu(Me) | γ-Methylleucine |
| Lys(Ac) | Nε-Acetyllysine |
| Lys(Hexyl) | Nε-Hexyllysine |
| Lys(Me) | Nε-methyllysine |
| Lys(Me2) | Nε,ε-Dimethyllysine |
| Lys[Hexadecanoyl-(PEG2)] | 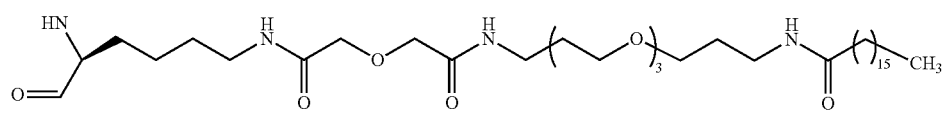 |
| Mtt | 4-Methyltrityl |

TABLE 1-2

| | |
|---|---|
| Abz(2) | 2-Aminobenzoic acid |
| Ac | Acetyl |
| Acp | 6-Aminocaproic acid |
| N(2-hydroxyethyl)Gly | N-(2-Hydroxyethyl)glycine |
| N(iBu)Gly | N-Isobutylglycine |
| Nal(1) | 1-Naphthylalanine |
| Nal(2) | 2-Naphthylalanine |
| Nar | Norarginine |
| Nle | Norleucine |
| NMeAla | Nα-Methylalanine |
| NMeSer | Nα-Methylserine |
| NMePhe | Nα-Methylphenylalanine |
| Nva | Norvaline |
| Orn | Ornithine |
| PEG2 | 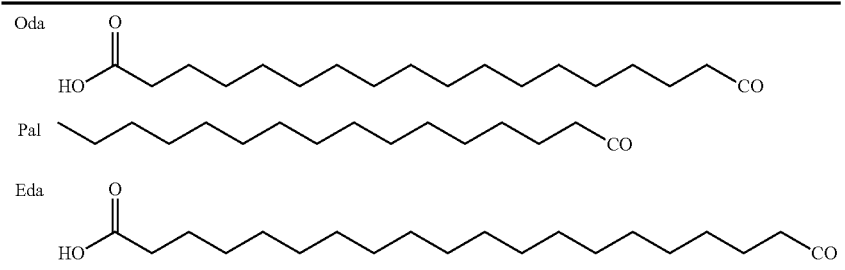 |
| Phe(2,6-Me$_2$) lat | 2,6-Dimethylphenylalanine |
| Phe(2-F) | 2-Fluorophenylalanine |
| Phe(2-Me) | 2-Methylphenylalanine |
| Phe(3-F) | 3-Fluorophenylalanine |
| Phe(3-Me) | 3-Methylphenylalanine |
| Phe(4-Cl) | 4-Chlorophenylalanine |
| Phe(4-F) | 4-Fluorophenylalanine |
| Phe(4-Me) | 4-Methylphenylalanine |
| Phe(4-NH$_2$) | 4-Aminophenylalanine |
| Phg | Phenylglycine |
| Pic(2) | 2-Piperidinecarboxylic acid |
| Pic(4) | 4-Piperidinecarboxylic acid |
| Pya(2) | 2-Pyridylalanine |
| Pya(3) | 3-Pyridylalanine |
| Pya(4) | 4-Pyridylalanine |
| Ser(Me) | O-Methylserine |
| Thp(4) | Tetrahydro-2H-pyran-4-yl |
| Thr(Me) | O-Methylthreonine |
| threo-PhSer | threo-3-phenylserine |
| Tic | 1,2,3,4-Tetrahydroisoquinoline-3-carboxylic acid |
| Tyr(2F) | 2-Fluorotyrosine |
| Tyr(3F) | 3-Fluorotyrosine |
| Tyr(Me) | O-Methyltyrosine |
| z | Benzyloxycarbonyl |
| α-MePhe | α-Methylphenylalanine |
| α-MePro | α-Methylproline |
| β-Ala | β-Alanine |
| β-HOAla | β-Homoalanine |

TABLE 1-3

Oda, Pal, Eda (fatty acid structures shown)

In the specification, where bases, amino acids, etc. are denoted by their codes, they are based on conventional codes in accordance with the IUPAC-IUB Commission on Biochemical Nomenclature or by the common codes in the art, examples of which are shown below. For amino acids that may have an optical isomer, L-form is presented unless otherwise indicated (e.g., "Ala" is L-form of Ala). In addition, "D-" means a D-form (e.g., "D-Ala" is D-form of Ala), and "DL-" means a racemate of a D-form and an L-form (e.g., "DL-Ala" is DL racemate of Ala).

TFA : : trifluoroacetic acid
Gly or G : : glycine
Ala or A : : alanine
Val or V : : valine
Leu or L : : leucine
Ile or I : : isoleucine
Ser or S : : serine
Thr or T : : threonine
Cys or C : : cysteine
Met or M : : methionine

| Glu or E : : glutamic acid |
| Asp or D : : aspartic acid |
| Lys or K : : lysine |
| Arg or R : : arginine |
| His or H : : histidine |
| Phe or F : : phenylalanine |
| Tyr or Y : : tyrosine |
| Trp or W : : tryptophan |
| Pro or P : : proline |
| Asn or N : : asparagine |
| Gln or Q : : glutamine |
| pGlu : : pyroglutamic acid |
| α-MeTyr : : α-methyltyrosine |

The present invention is explained in detail in the following by referring to the following Reference Examples, Examples, Experimental Examples and Formulation Examples, which are mere embodiments and not to be construed as limitative. In addition, the present invention may be modified without departing from the scope of invention.

The term "room temperature" in the following Examples indicates the range of generally from about 10° C. to about 35° C. As for "%", the yield is in mol/mol %, the solvent used for chromatography is in % by volume and other "%" is in % by weight.

THF: tetrahydrofuran
DMF: N,N-dimethylformamide
WSC: 1-(3-dimethylaminopropyl)-3-ethylcarbodiimide hydrochloride
HOBt: 1-hydroxybenzotriazole monohydrate Reference Example 1

Synthesis of H-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Phe(2-F)-Sieber Amide Resin
(SEQ ID NO: 2)

Sieber amide resin (0.71 meq/g, 352 mg) was added to a reaction tube, which was then loaded in a peptide synthesizer. Amino acids were successively condensed according to the Fmoc/DCC/HOBt protocol. Double coupling was performed for introducing 29-position Lys(Boc). In the final step, the N-terminal Fmoc group was removed. After the termination of condensation, the resin was washed with MeOH, and dried under reduced pressure. As a result, 1384 mg (0.181 meq/g) of the protected peptide resin of interest was obtained.

Reference Example 2

Synthesis of H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Ala-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Phe(2-F)-Sieber Amide Resin
(SEQ ID NO: 3)

H-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Phe(2-F)-Sieber amide resin (0.181 meq/g, 276 mg) prepared in Reference Example 1 was added to a reaction tube, which was then loaded in a peptide synthesizer. Amino acids were successively condensed according to the Fmoc/DIPCDI/OxymaPure protocol. Double coupling was performed for introducing 19-position Gln(Trt), 18-position Ala, 12-position Ile and 5-position Thr(tBu). In the final step, the N-terminal Fmoc group was removed. After the termination of condensation, the resin was washed with MeOH, and dried under reduced pressure. As a result, 389 mg (0.129 meq/g) of the protected peptide resin of interest was obtained.

Reference Example 3

Synthesis of H-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Phe(2-F)-Rink Amide AM Resin
(SEQ ID NO: 4)

Rink amide AM resin (0.29 meq/g, 862 mg) was added to a reaction tube, which was then loaded in a peptide synthesizer. Amino acids were successively condensed according to the Fmoc/DCC/HOBt protocol. Double coupling was performed for introducing 29-position Lys(Mtt). In the final step, the N-terminal Fmoc group was removed. After the termination of condensation, the resin was washed with MeOH, and dried under reduced pressure. As a result, 1788 mg (0.140 meq/g) of the protected peptide resin of interest was obtained.

Reference Example 4

Synthesis of H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Phe(2-F)-Rink Amide AM Resin
(SEQ ID NO: 5)

H-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Phe(2-F)-Rink amide AM resin (0.140 meq/g, 357 mg) prepared in Reference Example 3 was added to a reaction tube, which was then loaded in a peptide synthesizer. Amino acids were successively condensed according to the Fmoc/DIPCDI/OxymaPure protocol. Double coupling was performed for introducing 19-position Gln(Trt), 18-position Arg(Pbf), 12-position Ile and 5-position Thr(tBu). In the final step, the N-terminal Fmoc group was removed. After the termination of condensation, the resin was washed with MeOH, and dried under reduced pressure. As a result, 452 mg (0.111 meq/g) of the protected peptide resin of interest was obtained.

Reference Example 5

Synthesis of H-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink Amide AM Resin
(SEQ ID NO: 6)

Rink amide AM resin (0.29 meq/g, 690 mg was added to a reaction tube, which was then loaded in a peptide synthesizer. Amino acids were successively condensed according to the Fmoc/DCC/HOBt protocol. Double coupling was performed for introducing 29-position Lys(Mtt). In the final step, the N-terminal Fmoc group was removed. After the termination of condensation, the resin was washed with MeOH, and dried under reduced pressure. As a result, 1449 mg (0.138 meq/g) of the protected peptide resin of interest was obtained.

Reference Example 6

Synthesis of H-Aib-Glu(OtBu)-Gly-Thr(tBu)-αMePhe-Thr(tBu)-Ser(tBu)-Asp(OtBu)-Lys(ivDde)-Aib-Ile-Aib-Leu- Asp(OtBu)-Lys(Boc)-Gln(Trt)-Arg(Pbf)-Gln(Trt)-Iva-Glu
(OtBu)-Phe-Val-Arg(Pbf)-His(Trt)-Leu-Leu-Asn(Trt)-Lys
(Mtt)-Aib-Thr(tBu)-Arg(Pbf)-Gln(Trt)-Arg(Pbf)-Tyr(tBu)-
Rink Amide AM Resin (SEQ ID NO: 7)

H-Iva-Glu(OtBu)-Phe-Val-Arg(Pbf)-His(Trt)-Leu-Leu-
Asn(Trt)-Lys(Mtt)-Aib-Thr(tBu)-Arg(Pbf)-Gln(Trt)-Arg
(Pbf)-Tyr(tBu)-Rink amide AM resin (0.138 meq/g, 290 mg)
prepared in Reference Example 5 was added to a reaction
tube, which was then loaded in a peptide synthesizer. Amino
acids were successively condensed according to the Fmoc/
DIPCDI/OxymaPure protocol. Double coupling was per-
formed for introducing 19-position Gln(Trt), 18-position
Arg(Pbf), 12-position Ile and 5-position Thr(tBu). In the
final step, the N-terminal Fmoc group was removed. After
the termination of condensation, the resin was washed with
MeOH, and dried under reduced pressure. As a result, 417
mg (0.096 meq/g) of the protected peptide resin of interest
was obtained.

Reference Example 7

Synthesis of H-Iva-Glu(OtBu)-Phe-Val-Arg(Pbf)-His(Trt)-
Leu-Leu-Asn(Trt)-Lys(Boc)-Aib-Thr(tBu)-Arg(Pbf)-Gln
(Trt)-Arg(Pbf)-Tyr(tBu)-Sieber Amide Resin (SEQ ID NO: 8)

Sieber amide resin (0.71 meq/g, 352 mg) was added to a
reaction tube, which was then loaded in a peptide synthe-
sizer. Amino acids were successively condensed according
to the Fmoc/DCC/HOBt protocol. Double coupling was
performed for introducing 29-position Lys(Boc). In the final
step, the N-terminal Fmoc group was removed. After the
termination of condensation, the resin was washed with
MeOH, and dried under reduced pressure. As a result, 1373
mg (0.182 meq/g) of the protected peptide resin of interest
was obtained.

Reference Example 8

Synthesis of H-Aib-Glu(OtBu)-Gly-Thr(tBu)-αMePhe-Thr
(tBu)-Ser(tBu)-Asp(OtBu)-Lys(ivDde)-Aib-Ile-Aib-Leu-
Asp(OtBu)-Lys(Boc)-Gln(Trt)-Ala-Gln(Trt)-Iva-Glu
(OtBu)-Phe-Val-Arg(Pbf)-His(Trt)-Leu-Leu-Asn(Trt)-Lys
(Boc)-Aib-Thr(tBu)-Arg(Pbf)-Gln(Trt)-Arg(Pbf)-Tyr(tBu)-
Sieber Amide Resin (SEQ ID NO: 9)

H-Iva-Glu(OtBu)-Phe-Val-Arg(Pbf)-His(Trt)-Leu-Leu-
Asn(Trt)-Lys(Boc)-Aib-Thr(tBu)-Arg(Pbf)-Gln(Trt)-Arg
(Pbf)-Tyr(tBu)-Sieber amide resin (0.182 meq/g, 275 mg)
prepared in Reference Example 7 was added to a reaction
tube, which was then loaded in a peptide synthesizer. Amino
acids were successively condensed according to the Fmoc/
DIPCDI/OxymaPure protocol. Double coupling was per-
formed for introducing 19-position Gln(Trt), 18-position
Ala, 12-position Ile and 5-position Thr(tBu). In the final
step, the N-terminal Fmoc group was removed. After the
termination of condensation, the resin was washed with
MeOH, and dried under reduced pressure. As a result, 409
mg (0.122 meq/g) of the protected peptide resin of interest
was obtained.

Example 1

(SEQ ID NO: 10)
H-Tyr-Aib-Glu-Gly-Thr-αMePhe-Thr-Ser-Asp-Lys(-Gly-

Gly-Gly-Gly-Pal)-Aib-Ile-Aib-Leu-Asp-Lys-Gln-Ala-

Gln-Iva-Glu-Phe-Val-Arg-His-Leu-Leu-Asn-Lys-Aib-

Thr-Arg-Gln-Arg-Phe(2-F)-NH$_2$

H-Aib-Glu(OtBu)-Gly-Thr(tBu)-αMePhe-Thr(tBu)-Ser
(tBu)-Asp(OtBu)-Lys(ivDde)-Aib-Ile-Aib-Leu-Asp(OtBu)-
Lys(Boc)-Gln(Trt)-Ala-Gln(Trt)-Iva-Glu(OtBu)-Phe-Val-
Arg(Pbf)-His(Trt)-Leu-Leu-Asn(Trt)-Lys(Boc)-Aib-Thr
(tBu)-Arg(Pbf)-Gln(Trt)-Arg(Pbf)-Phe(2-F)-Sieber amide
resin (0.129 meq/g, 97 mg) prepared in Reference Example
2 was weighed into a reaction tube, and swollen with NMP.
After removal of NMP by filtration, Boc-Tyr(tBu)-OH (33.7
mg), 0.5 M OxymaPure in NMP (200 µL) and diisopropy-
lcarbodiimide (15.9 µL) were successively added to the
resin, and then the mixture was shaken overnight. The
reaction solution was filtered off, and the resin was then
washed with NMP 6 times. After confirmation of negativity
in the Kaiser test, a NMP solution of 2% hydrazine was
added to the obtained resin, and the mixture was shaken for
3 hours. The solution was filtered off, and a NMP solution
of 2% hydrazine was then added thereto again, and the
mixture was shaken overnight. The reaction solution was
filtered off, and the resin was then washed with NMP 6
times. Fmoc-Gly-OH (29.7 mg), 0.5 M OxymaPure in NMP
(200 µL) and diisopropylcarbodiimide (15.9 µL) were suc-
cessively added to the obtained resin, and then the mixture
was shaken overnight. The reaction solution was filtered off,
and the resin was then washed with NMP 6 times. After
confirmation of negativity in the Kaiser test, a NMP solution
of 20% piperidine was added thereto, and the mixture was
shaken for 1 minute. The solution was filtered off, and a
NMP solution of 20% piperidine was then added thereto
again, and the mixture was shaken for 20 minutes. The
solution was filtered off, and the resin was then washed with
NMP 10 times. Fmoc-Gly-Gly-Gly-OH (41.1 mg), 0.5 M
OxymaPure in NMP (200 µL) and diisopropylcarbodiimide
(15.9 µL) were successively added to the obtained resin, and
then the mixture was shaken overnight. The reaction solu-
tion was filtered off, and the resin was then washed with
NMP 6 times. After confirmation of negativity in the Kaiser
test, a NMP solution of 20% piperidine was added thereto,
and the mixture was shaken for 1 minute. The solution was
filtered off, and a NMP solution of 20% piperidine was then
added thereto again, and the mixture was shaken for 20
minutes. The solution was filtered off, and the resin was then
washed with NMP 10 times. A NMP solution (200 µL) of
Pal-OSu (35.4 mg) and DIPEA (17.4 µL) was added to the
obtained resin, and the mixture was then shaken overnight.
The reaction solution was filtered off, and the resin was then
washed with NMP 6 times. After confirmation of negativity
in the Kaiser test, the resin was washed with MeOH, and
dried under reduced pressure to give 101.3 mg of Boc-Tyr
(tBu)-Aib-Glu(OtBu)-Gly-Thr(tBu)-αMePhe-Thr(tBu)-Ser
(tBu)-Asp(OtBu)-Lys(-Gly-Gly-Gly-Gly-Pal)-Aib-Ile-Aib-
Leu-Asp(OtBu)-Lys(Boc)-Gln(Trt)-Ala-Gln(Trt)-Iva-Glu
(OtBu)-Phe-Val-Arg(Pbf)-His(Trt)-Leu-Leu-Asn(Trt)-Lys
(Boc)-Aib-Thr(tBu)-Arg(Pbf)-Gln(Trt)-Arg(Pbf)-Phe(2-F)-
Sieber amide resin.

To 101.3 mg of the obtained resin was added 1 mL of
TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 56/44-46/54 linear concentration gradient elution (60 min)]. The fractions containing the object product were collected and freeze-dried to give 23.1 mg of a white powder.

Mass spectrometry, (M+H)$^+$ 4606.1 (Calculated: 4605.5)
HPLC elution time: 17.4 min
Elution Condition:
  Column: YMC Triart C8 (100×4.6 mm I.D.)
  Eluent: using Solution A: 0.1% TFA-water, Solution B: 0.1% TFA-containing acetonitrile, A/B: 80/20-30/70 linear concentration gradient elution (25 min).
  Flow rate: 1.0 mL/min Example 2

(SEQ ID NO: 11)
H-Tyr-Aib-Glu-Gly-Thr-αMePhe-Thr-Ser-Asp-Lys(-Gly-

Gly-Gly-Gly-Oda)-Aib-Ile-Aib-Leu-Asp-Lys-Gln-Ala-

Gln-Iva-Glu-Phe-Val-Arg-His-Leu-Leu-Asn-Lys-Aib-

Thr-Arg-Gln-Arg-Phe(2-F)-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Ala-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Phe(2-F)-Sieber amide resin (0.129 meq/g, 97 mg) prepared in Reference Example 2 was weighed into a reaction tube, and swollen with NMP. After removal of NMP by filtration, Boc-Tyr(tBu)-OH (33.7 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and dried under reduced pressure to give 94.6 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(tBu))-Aib-Ile-Aib-Leu-Asp(OtBu)-Lys(Boc)-Gln(Trt)-Ala-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Phe(2-F)-Sieber amide resin.

To 94.6 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 60/40-50/50 linear concentration gradient elution (60 min)]. The fractions containing the object product were collected and freeze-dried to give 21.4 mg of a white powder.

Mass spectrometry, (M+H)$^+$ 4664.4 (Calculated: 4663.6)
HPLC elution time: 15.4 min
Elution Condition:
  Column: YMC Triart C8 (100×4.6 mm I.D.)
  Eluent: using Solution A: 0.1% TFA-water, Solution B: 0.1% TFA-containing acetonitrile, A/B: 80/20-30/70 linear concentration gradient elution (25 min).
  Flow rate: 1.0 mL/min Example 3

(SEQ ID NO: 12)
H-Tyr-Aib-Glu-Gly-Thr-αMePhe-Thr-Ser-Asp-Lys(-Gly-

Gly-Gly-Gly-Pal)-Aib-Ile-Aib-Leu-Asp-Lys-Gln-Arg-

Gln-Iva-Glu-Phe-Val-Arg-His-Leu-Leu-Asn-Lys-Aib-

Thr-Arg-Gln-Arg-Phe(2-F)-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Phe(2-F)-Rink amide AM resin (0.111 meq/g, 89.3 mg) prepared in Reference Example 4 was weighed into a reaction tube, and swollen with NMP. After removal of NMP by filtration, Boc-Tyr(tBu)-OH (33.7 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 μL) of Pal-OSu (35.4 mg) and DIPEA (17.4 μL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 110.2 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Phe(2-F)-Rink amide AM resin.

To 110.2 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 58/42-48/52 linear concentration gradient elution (60 min)]. The fractions containing the object product were collected and freeze-dried to give 9.3 mg of a white powder.

Mass spectrometry, (M+H)$^+$ 4691.1 (Calculated: 4690.6)
HPLC elution time: 16.9 min
Elution Condition:
  Column: YMC Triart C8 (100×4.6 mm I.D.)
  Eluent: using Solution A: 0.1% TFA-water, Solution B: 0.1% TFA-containing acetonitrile, A/B: 80/20-30/70 linear concentration gradient elution (25 min).
  Flow rate: 1.0 mL/min Example 4

(SEQ ID NO: 13)
H-Tyr-Aib-Glu-Gly-Thr-αMePhe-Thr-Ser-Asp-Lys(-Gly-Gly-Gly-Gly-Oda)-Aib-Ile-Aib-Leu-Asp-Lys-Gln-Arg-Gln-Iva-Glu-Phe-Val-Arg-His-Leu-Leu-Asn-Lys-Aib-Thr-Arg-Gln-Arg-Phe(2-F)-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Phe(2-F)-Rink amide AM resin (0.111 meq/g, 89.3 mg) prepared in Reference Example 4 was weighed into a reaction tube, and swollen with NMP. After removal of NMP by filtration, Boc-Tyr(tBu)-OH (33.7 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 109.6 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Phe(2-F)-Rink amide AM resin.

To 109.6 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 9.5 mg of a white powder.

Mass spectrometry, (M+H)$^+$ 4749.1 (Calculated: 4748.6)
HPLC elution time: 14.9 min
Elution Condition:
  Column: YMC Triart C8 (100×4.6 mm I.D.)
  Eluent: using Solution A: 0.1% TFA-water, Solution B: 0.1% TFA-containing acetonitrile, A/B: 80/20-30/70 linear concentration gradient elution (25 min).
  Flow rate: 1.0 mL/min

Example 5

(SEQ ID NO: 14)
Me-Tyr-Aib-Glu-Gly-Thr-αMePhe-Thr-Ser-Asp-

Lys(-Gly-Gly-Gly-Gly-Pal)-Aib-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Phe(2-F)-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Phe(2-F)-Rink amide AM resin (0.111 meq/g, 89.3 mg) prepared in Reference Example 4 was weighed into a reaction tube, and swollen with NMP. After removal of NMP by filtration, Boc-NMe-Tyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 μL) of Pal-OSu (35.4 mg) and DIPEA (17.4 μL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 135.1 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Phe(2-F)-Rink amide AM resin.

To 135.1 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 10.8 mg of a white powder.

Mass spectrometry, (M+H)$^+$ 4705.1 (Calculated: 4704.6)

HPLC elution time: 16.9 min

Elution Condition:
 Column: YMC Triart C8 (100×4.6 mm I.D.)
 Eluent: using Solution A: 0.1% TFA-water, Solution B: 0.1% TFA-containing acetonitrile, A/B: 80/20-30/70 linear concentration gradient elution (25 min).
 Flow rate: 1.0 mL/min

Example 6

(SEQ ID NO: 15)
Me-Tyr-Aib-Glu-Gly-Thr-αMePhe-Thr-Ser-Asp-

Lys(-Gly-Gly-Gly-Gly-Oda)-Aib-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Phe(2-F)-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Phe(2-F)-Rink amide AM resin (0.111 meq/g, 89.3 mg) prepared in Reference Example 4 was weighed into a reaction tube, and swollen with NMP. After removal of NMP by filtration, Boc-NMe-Tyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 121.2 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Phe(2-F)-Rink amide AM resin.

To 121.2 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 9.1 mg of a white powder.

Mass spectrometry, (M+H)$^+$ 4763.3 (Calculated: 4762.6)
HPLC elution time: 14.9 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 7

(SEQ ID NO: 16)
H-Tyr-Aib-Glu-Gly-Thr-αMePhe-Thr-Ser-Asp-

Lys(-Gly-Gly-Gly-Gly-Pal)-Aib-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.096 meq/g, 104 mg) prepared in Reference Example 6 was weighed into a reaction tube, and swollen with NMP. After removal of NMP by filtration, Boc-Tyr(tBu)-OH (33.7 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 µL) of Pal-OSu (35.4 mg) and DIPEA (17.4 µL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 109.1 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 109.1 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 7.9 mg of a white powder.

Mass spectrometry, (M+H)$^+$ 4689.4 (Calculated: 4688.6)
HPLC elution time: 16.6 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 8

(SEQ ID NO: 17)
H-Tyr-Aib-Glu-Gly-Thr-αMePhe-Thr-Ser-Asp-

Lys(-Gly-Gly-Gly-Gly-Oda)-Aib-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.096 meq/g, 104 mg) prepared in Reference Example 6 was weighed into a reaction tube, and swollen with NMP. After removal of NMP by filtration, Boc-Tyr(tBu)-OH (33.7 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 104.1 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 104.1 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 7.7 mg of a white powder.

Mass spectrometry, (M+H)$^+$ 4747.5 (Calculated: 4746.6)
HPLC elution time: 14.6 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 9

(SEQ ID NO: 18)
Me-Tyr-Aib-Glu-Gly-Thr-αMePhe-Thr-Ser-Asp-

Lys(-Gly-Gly-Gly-Gly-Pal)-Aib-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.096 meq/g, 104 mg) prepared in Reference Example 6 was weighed into a reaction tube, and swollen with NMP. After removal of NMP by filtration, Boc-NMe-Tyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 μL) of Pal-OSu (35.4 mg) and DIPEA (17.4 μL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 99.6 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 99.6 mg of the obtained resin was added 1 mL of TFA:m-cresol:thioanisole:ethanedithiol:H₂O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 8.3 mg of a white powder.

Mass spectrometry, (M+H)⁺ 4703.5 (Calculated: 4702.6)
HPLC elution time: 16.6 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 10

(SEQ ID NO: 19)
Me-Tyr-Aib-Glu-Gly-Thr-αMePhe-Thr-Ser-Asp-

Lys(-Gly-Gly-Gly-Gly-Oda)-Aib-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH₂

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.096 meq/g, 104 mg) prepared in Reference Example 6 was weighed into a reaction tube, and swollen with NMP. After removal of NMP by filtration, Boc-NMe-Tyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 110.6 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Aib-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 110.6 mg of the obtained resin was added 1 mL of TFA:m-cresol:thioanisole:ethanedithiol:H₂O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 7.9 mg of a white powder.

Mass spectrometry, (M+H)⁺ 4761.5 (Calculated: 4760.6)
HPLC elution time: 14.6 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 11

(SEQ ID NO: 20)
H-Tyr-Aib-Glu-Gly-Thr-αMePhe-Thr-Ser-Asp-

Lys(-Gly-Gly-Gly-Gly-Pal)-Ala-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH₂

H-Aib-Glu(OtBu)-Gly-Thr(tBu)-αMePhe-Thr(tBu)-Ser(tBu)-Asp(OtBu)-Lys(ivDde)-Ala-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.089 meq/g, 112 mg) prepared by an approach similar to Reference Example 6 was weighed into a reaction tube, and swollen with NMP. After removal of NMP by filtration, Boc-Tyr(tBu)-OH (33.7 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 µL) of Pal-OSu (35.4 mg) and DIPEA (17.4 µL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 103.9 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Ala-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 103.9 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 56/44-46/54 linear concentration gradient elution (60 min)]. The fractions containing the object product were collected and freeze-dried to give 8.8 mg of a white powder.

Mass spectrometry, (M+H)$^+$ 4674.6)
HPLC elution time: 16.6 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 12

(SEQ ID NO: 21)
H-Tyr-Aib-Glu-Gly-Thr-αMePhe-Thr-Ser-Asp-

Lys(-Gly-Gly-Gly-Gly-Oda)-Ala-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ala-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.089 meq/g, 112 mg) prepared by an approach similar to Reference Example 6 was weighed into a reaction tube, and swollen with NMP. After removal of NMP by filtration, Boc-Tyr(tBu)-OH (33.7 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 103.2 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Ala-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 103.2 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 60/40-50/50 linear concentration gradient elution (60 min)]. The fractions containing the object product were collected and freeze-dried to give 8.5 mg of a white powder.

Mass spectrometry, (M+H)$^+$ 4732.1 (Calculated: 4732.6)
HPLC elution time: 14.5 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min

Example 13

(SEQ ID NO: 22)
Me-Tyr-Aib-Glu-Gly-Thr-αMePhe-Thr-Ser-Asp-Lys (-Gly-Gly-Gly-Gly-Pal)-Ala-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ala-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.089 meq/g, 112 mg) prepared by an approach similar to Reference Example 6 was weighed into a reaction tube, and swollen with NMP. After removal of NMP by filtration, Boc-NMeTyr(tBu)-OH (35.1 mg), 0.5 M Oxyma-Pure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M Oxyma-Pure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 μL) of Pal-OSu (35.4 mg) and DIPEA (17.4 μL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 99.9 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Ala-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 99.9 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 56/44-46/54 linear concentration gradient elution (60 min)]. The fractions containing the object product were collected and freeze-dried to give 8.8 mg of a white powder.

Mass spectrometry, (M+H)$^+$ 4688.4 (Calculated: 4688.6)

HPLC elution time: 16.6 min

Elution Condition:

Column: YMC Triart C8 (100×4.6 mm I.D.)

Eluent: using Solution A: 0.1% TFA-water, Solution B: 0.1% TFA-containing acetonitrile, A/B: 80/20-30/70 linear concentration gradient elution (25 min).

Flow rate: 1.0 mL/min

Example 14

(SEQ ID NO: 23)
Me-Tyr-Aib-Glu-Gly-Thr-αMePhe-Thr-Ser-Asp-Lys (-Gly-Gly-Gly-Gly-Oda)-Ala-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ala-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.089 meq/g, 112 mg) prepared by an approach similar to Reference Example 6 was weighed into a reaction tube, and swollen with NMP. After removal of NMP by filtration, Boc-NMeTyr(tBu)-OH (35.1 mg), 0.5 M Oxyma-Pure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 111.4 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda (OtBu))-Ala-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 111.4 mg of the obtained resin was added 1 mL of TFA:m-cresol:thioanisole:ethanedithiol:$H_2O$:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 60/40-50/50 linear concentration gradient elution (60 min)]. The fractions containing the object product were collected and freeze-dried to give 7.0 mg of a white powder.

Mass spectrometry, $(M+H)^+$ 4746.2 (Calculated: 4746.6)
HPLC elution time: 14.5 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 15

(SEQ ID NO: 24)
H-Tyr-Aib-Glu-Gly-Thr-αMePhe-Thr-Ser-Asp-Lys (-Gly-Gly-Gly-Gly-Pal)-Ser-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-$NH_2$

H-Aib-Glu(OtBu)-Gly-Thr(tBu)-αMePhe-Thr(tBu)-Ser(tBu)-Asp(OtBu)-Lys(ivDde)-Ser(tBu)-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.088 meq/g, 113 mg) prepared by an approach similar to Reference Example 6 was weighed into a reaction tube, and swollen with NMP. After removal of NMP by filtration, Boc-Tyr(tBu)-OH (33.7 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M Oxyma-Pure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 μL) of Pal-OSu (35.4 mg) and DIPEA (17.4 μL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 100.5 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Ser(tBu)-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 100.5 mg of the obtained resin was added 1 mL of TFA:m-cresol:thioanisole:ethanedithiol:$H_2O$:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 56/44-46/54 linear concentration gradient elution (60 min)]. The fractions containing the object product were collected and freeze-dried to give 7.8 mg of a white powder.

Mass spectrometry, $(M+H)^+$ 4690.3 (Calculated: 4690.6)
HPLC elution time: 16.6 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 16

(SEQ ID NO: 25)
H-Tyr-Aib-Glu-Gly-Thr-αMePhe-Thr-Ser-Asp-Lys (-Gly-Gly-Gly-Gly-Oda)-Ser-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-$NH_2$

H-Aib-Glu(OtBu)-Gly-Thr(tBu)-αMePhe-Thr(tBu)-Ser(tBu)-Asp(OtBu)-Lys(ivDde)-Ser(tBu)-Ile-Aib-Leu-Asp(OtBu)-Lys(Boc)-Gln(Trt)-Arg(Pbf)-Gln(Trt)-Iva-Glu (OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.088 meq/g, 113 mg) prepared by an approach similar to Reference Example 6 was weighed into a reaction tube, and swollen with NMP. After removal of NMP by filtration, Boc-Tyr(tBu)-OH (33.7 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 96.8 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Ser(tBu)-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 96.8 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 60/40-50/50 linear concentration gradient elution (60 min)]. The fractions containing the object product were collected and freeze-dried to give 7.5 mg of a white powder.

Mass spectrometry, (M+H)$^+$ 4748.5 (Calculated: 4748.6)
HPLC elution time: 14.5 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 17

(SEQ ID NO: 26)
Me-Tyr-Aib-Glu-Gly-Thr-αMePhe-Thr-Ser-Asp-Lys
(-Gly-Gly-Gly-Gly-Pal)-Ser-Ile-Aib-Leu-Asp-Lys-
Gln-Arg-Gln-Iva-Glu-Phe-Val-Arg-His-Leu-Leu-Asn-
Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ser(tBu)-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.088 meq/g, 113 mg) prepared by an approach similar to Reference Example 6 was weighed into a reaction tube, and swollen with NMP. After removal of NMP by filtration, Boc-NMeTyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 μL) of Pal-OSu (35.4 mg) and DIPEA (17.4 μL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 96.4 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Ser(tBu)-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 96.4 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 56/44-46/54 linear concentration gradient elution (60 min)]. The fractions containing the object product were collected and freeze-dried to give 7.9 mg of a white powder.

Mass spectrometry, (M+H)$^+$ 4704.3 (Calculated: 4704.6)
HPLC elution time: 16.6 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 18

(SEQ ID NO: 27)
Me-Tyr-Aib-Glu-Gly-Thr-αMePhe-Thr-Ser-Asp-Lys (-Gly-Gly-Gly-Gly-Oda)-Ser-Ile-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ser(tBu)-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.088 meq/g, 113 mg) prepared by an approach similar to Reference Example 6 was weighed into a reaction tube, and swollen with NMP. After removal of NMP by filtration, Boc-NMeTyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 115.1 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Ser(tBu)-Ile-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 115.1 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 60/40-50/50 linear concentration gradient elution (60 min)]. The fractions containing the object product were collected and freeze-dried to give 7.0 mg of a white powder.

Mass spectrometry, (M+H)$^+$ 4762.7 (Calculated: 4762.6)
HPLC elution time: 14.5 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 19

(SEQ ID NO: 28)
H-Tyr-Aib-Glu-Gly-Thr-αMePhe-Thr-Ser-Asp-Lys (-Gly-Gly-Gly-Gly-Pal)-Aib-Lys-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.093 meq/g, 108 mg) prepared by an approach similar to Reference Example 6 was weighed into a reaction tube, and swollen with NMP. After removal of NMP by filtration, Boc-Tyr(tBu)-OH (33.7 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M Oxyma-Pure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 µL) of Pal-OSu (35.4 mg) and DIPEA (17.4 µL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 105.4 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Aib-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 105.4 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 10.0 mg of a white powder.

Mass spectrometry, (M+H)$^+$ 4703.5 (Calculated: 4703.6)

HPLC elution time: 16.0 min

Elution Condition:

Column: YMC Triart C8 (100×4.6 mm I.D.)

Eluent: using Solution A: 0.1% TFA-water, Solution B: 0.1% TFA-containing acetonitrile, A/B: 80/20-30/70 linear concentration gradient elution (25 min).

Flow rate: 1.0 mL/min

Example 20

(SEQ ID NO: 29)
H-Tyr-Aib-Glu-Gly-Thr-αMePhe-Thr-Ser-Asp-Lys
(-Gly-Gly-Gly-Gly-Oda)-Aib-Lys-Aib-Leu-Asp-Lys-
Gln-Arg-Gln-Iva-Glu-Phe-Val-Arg-His-Leu-Leu-Asn-
Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.093 meq/g, 108 mg) prepared by an approach similar to Reference Example 6 was weighed into a reaction tube, and swollen with NMP. After removal of NMP by filtration, Boc-Tyr(tBu)-OH (33.7 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 101.6 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Aib-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 101.6 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 8.9 mg of a white powder.

Mass spectrometry, (M+H)$^+$ 4761.3 (Calculated: 4761.6)

HPLC elution time: 13.9 min

Elution Condition:

Column: YMC Triart C8 (100×4.6 mm I.D.)

Eluent: using Solution A: 0.1% TFA-water, Solution B: 0.1% TFA-containing acetonitrile, A/B: 80/20-30/70 linear concentration gradient elution (25 min).

Flow rate: 1.0 mL/min

Example 21

(SEQ ID NO: 30)
Me-Tyr-Aib-Glu-Gly-Thr-αMePhe-Thr-Ser-Asp-Lys (-Gly-Gly-Gly-Gly-Pal)-Aib-Lys-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.093 meq/g, 108 mg) prepared by an approach similar to Reference Example 6 was weighed into a reaction tube, and swollen with NMP. After removal of NMP by filtration, Boc-NMeTyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 μL) of Pal-OSu (35.4 mg) and DIPEA (17.4 μL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 106 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Aib-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 106 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 9.9 mg of a white powder.

Mass spectrometry, (M+H)$^+$ 4717.2 (Calculated: 4717.6)

HPLC elution time: 16.0 min

Elution Condition:

Column: YMC Triart C8 (100×4.6 mm I.D.)

Eluent: using Solution A: 0.1% TFA-water, Solution B: 0.1% TFA-containing acetonitrile, A/B: 80/20-30/70 linear concentration gradient elution (25 min).

Flow rate: 1.0 mL/min

Example 22

(SEQ ID NO: 31)
Me-Tyr-Aib-Glu-Gly-Thr-αMePhe-Thr-Ser-Asp-Lys (-Gly-Gly-Gly-Gly-Oda)-Aib-Lys-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.093 meq/g, 108 mg) prepared by an approach similar to Reference Example 6 was weighed into a reaction tube, and swollen with NMP. After removal of NMP by filtration, Boc-NMeTyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 98.4 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Aib-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 98.4 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 8.8 mg of a white powder.

Mass spectrometry, (M+H)$^+$ 4775.5 (Calculated: 4775.6)
HPLC elution time: 13.9 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 23

(SEQ ID NO: 32)
H-Tyr-Aib-Glu-Gly-Thr-αMePhe-Thr-Ser-Asp-Lys (-Gly-Gly-Gly-Gly-Pal)-Ser-Lys-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ser(tBu)-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.084 meq/g, 119 mg) prepared by an approach similar to Reference Example 6 was weighed into a reaction tube, and swollen with NMP. After removal of NMP by filtration, Boc-Tyr(tBu)-OH (33.7 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M Oxyma-Pure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 μL) of Pal-OSu (35.4 mg) and DIPEA (17.4 μL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 111.3 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Ser(tBu)-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 111.3 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 9.3 mg of a white powder.

Mass spectrometry, (M+H)$^+$ 4705.3 (Calculated: 4705.6)
HPLC elution time: 16.0 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 24

(SEQ ID NO: 33)
H-Tyr-Aib-Glu-Gly-Thr-αMePhe-Thr-Ser-Asp-Lys (-Gly-Gly-Gly-Gly-Oda)-Ser-Lys-Aib-Leu-Asp-Lys-

-continued
Gln-Arg-Gln-Iva-Glu-Phe-Val-Arg-His-Leu-Leu-Asn-

Lys-Aib-Thr-Arg-Gln-Arg-Tyr-NH₂

H-Aib-Glu(OtBu)-Gly-Thr(tBu)-αMePhe-Thr(tBu)-Ser(tBu)-Asp(OtBu)-Lys(ivDde)-Ser(tBu)-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.084 meq/g, 119 mg) prepared by an approach similar to Reference Example 6 was weighed into a reaction tube, and swollen with NMP. After removal of NMP by filtration, Boc-Tyr(tBu)-OH (33.7 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 101.8 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Ser(tBu)-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 101.8 mg of the obtained resin was added 1 mL of TFA:m-cresol:thioanisole:ethanedithiol:H₂O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 8.5 mg of a white powder.

Mass spectrometry, (M+H)⁺ 4763.4 (Calculated: 4763.6)
HPLC elution time: 13.9 min
Elution Condition:
Column: YMC Triart C8 (100×4.6 mm I.D.)

Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 25

(SEQ ID NO: 34)
Me-Tyr-Aib-Glu-Gly-Thr-αMePhe-Thr-Ser-Asp-Lys (-Gly-Gly-Gly-Gly-Pal)-Ser-Lys-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH₂

H-Aib-Glu(OtBu)-Gly-Thr(tBu)-αMePhe-Thr(tBu)-Ser(tBu)-Asp(OtBu)-Lys(ivDde)-Ser(tBu)-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.084 meq/g, 119 mg) prepared by an approach similar to Reference Example 6 was weighed into a reaction tube, and swollen with NMP. After removal of NMP by filtration, Boc-NMeTyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 μL) of Pal-OSu (35.4 mg) and DIPEA (17.4 μL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 104.3 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Ser (tBu)-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 104.3 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 8.2 mg of a white powder.

Mass spectrometry, (M+H)$^+$ 4719.7 (Calculated: 4719.6)
HPLC elution time: 16.0 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 26

(SEQ ID NO: 35)
Me-Tyr-Aib-Glu-Gly-Thr-αMePhe-Thr-Ser-Asp-Lys (-Gly-Gly-Gly-Gly-Oda)-Ser-Lys-Aib-Leu-Asp-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ser(tBu)-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin (0.084 meq/g, 119 mg) prepared by an approach similar to Reference Example 6 was weighed into a reaction tube, and swollen with NMP. After removal of NMP by filtration, Boc-NMeTyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 125.9 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Ser(tBu)-Lys(Boc)-Aib-Leu-Asp(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Mtt)-Aib-Thr(tBu)-Arg(Pbf)-Gln(Trt)-Arg(Pbf)-Tyr(tBu)-Rink amide AM resin.

To 125.9 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 10.6 mg of a white powder.

Mass spectrometry, (M+H)$^+$ 4777.5 (Calculated: 4777.6)
HPLC elution time: 13.9 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 27

(SEQ ID NO: 36)
H-Tyr-Aib-Glu-Gly-Thr-αMePhe-Thr-Ser-Asp-Lys (-Gly-Gly-Gly-Gly-Pal)-Aib-Ile-Aib-Leu-Asp-Lys-

Gln-Ala-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Ala-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.122 meq/g, 102.3 mg) prepared in Reference Example 8 was weighed into a reaction tube, and swollen with NMP. After removal of NMP by filtration, Boc-Tyr(tBu)-OH (33.7 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 µL) of Pal-OSu (35.4 mg) and DIPEA (17.4 µL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 104.5 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Aib-Ile-Aib-Leu-Asp(OtBu)-Lys(Boc)-Gln(Trt)-Ala-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 104.5 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 13.3 mg of a white powder.

Mass spectrometry, (M+H)$^+$ 4604.3 (Calculated: 4603.6)

HPLC elution time: 17.1 min

Elution Condition:

Column: YMC Triart C8 (100×4.6 mm I.D.)

Eluent: using Solution A: 0.1% TFA-water, Solution B: 0.1% TFA-containing acetonitrile, A/B: 80/20-30/70 linear concentration gradient elution (25 min).

Flow rate: 1.0 mL/min

Example 28

(SEQ ID NO: 37)
H-Tyr-Aib-Glu-Gly-Thr-αMePhe-Thr-Ser-Asp-Lys (-Gly-Gly-Gly-Gly-Oda)-Aib-Ile-Aib-Leu-Asp-Lys-

Gln-Ala-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Ala-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.122 meq/g, 102.3 mg) prepared in Reference Example 8 was weighed into a reaction tube, and swollen with NMP. After removal of NMP by filtration, Boc-Tyr(tBu)-OH (33.7 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 109.1 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Aib-Ile-Aib-Leu-Asp(OtBu)-Lys(Boc)-Gln(Trt)-Ala-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 109.1 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 60/40-50/50 linear concentration gradient elution (60 min)]. The fractions containing the object product were collected and freeze-dried to give 12.4 mg of a white powder.

Mass spectrometry, (M+H)$^+$ 4662.3 (Calculated: 4661.6)
HPLC elution time: 15.1 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 29

(SEQ ID NO: 38)
Me-Tyr-Aib-Glu-Gly-Thr-αMePhe-Thr-Ser-Asp-Lys (-Gly-Gly-Gly-Gly-Pal)-Aib-Ile-Aib-Leu-Asp-Lys-

Gln-Ala-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Ala-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.122 meq/g, 102.3 mg) prepared in Reference Example 8 was weighed into a reaction tube, and swollen with NMP. After removal of NMP by filtration, Boc-NMe-Tyr(tBu)-OH (35.1 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 µL) of Pal-OSu (35.4 mg) and DIPEA (17.4 µL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 105.8 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Aib-Ile-Aib-Leu-Asp(OtBu)-Lys(Boc)-Gln(Trt)-Ala-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 105.8 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 56/44-46/54 linear concentration gradient elution (60 min)]. The fractions containing the object product were collected and freeze-dried to give 14.3 mg of a white powder.

Mass spectrometry, (M+H)$^+$ 4618.2 (Calculated: 4617.6)
HPLC elution time: 17.1 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 30

(SEQ ID NO: 39)
Me-Tyr-Aib-Glu-Gly-Thr-αMePhe-Thr-Ser-Asp-Lys (-Gly-Gly-Gly-Gly-Oda)-Aib-Ile-Aib-Leu-Asp-Lys-

Gln-Ala-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Asp(OtBu)-Lys(Boc)-Gln(Trt)-Ala-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.122 meq/g, 102.3 mg) prepared in Reference Example 8 was weighed into a reaction tube, and swollen with NMP. After removal of NMP by filtration, Boc-NMe-Tyr(tBu)-OH (35.1 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 118 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Aib-Ile-Aib-Leu-Asp(OtBu)-Lys(Boc)-Gln(Trt)-Ala-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 118 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 60/40-50/50 linear concentration gradient elution (60 min)]. The fractions containing the object product were collected and freeze-dried to give 12.1 mg of a white powder.

Mass spectrometry, (M+H)$^+$ 4676.2 (Calculated: 4675.6)

HPLC elution time: 15.1 min

Elution Condition:

Column: YMC Triart C8 (100×4.6 mm I.D.)

Eluent: using Solution A: 0.1% TFA-water, Solution B: 0.1% TFA-containing acetonitrile, A/B: 80/20-30/70 linear concentration gradient elution (25 min).

Flow rate: 1.0 mL/min

Example 31

(SEQ ID NO: 40)
H-Tyr-Aib-Glu-Gly-Thr-αMePhe-Thr-Ser-Asp-Lys (-Gly-Gly-Gly-Gly-Pal)-Aib-Ile-Aib-Leu-Glu-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.115 meq/g, 108.3 mg) prepared by an approach similar to Reference Example 8 was weighed into a reaction tube, and swollen with NMP. After removal of NMP by filtration, Boc-Tyr(tBu)-OH (33.7 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 µL) of Pal-OSu (35.4 mg) and DIPEA (17.4 µL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 131.4 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Aib-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 131.4 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 12.4 mg of a white powder.

Mass spectrometry, (M+H)$^+$ 4703.2 (Calculated: 4702.6)

HPLC elution time: 16.5 min

Elution Condition:

Column: YMC Triart C8 (100×4.6 mm I.D.)

Eluent: using Solution A: 0.1% TFA-water, Solution B: 0.1% TFA-containing acetonitrile, A/B: 80/20-30/70 linear concentration gradient elution (25 min).

Flow rate: 1.0 mL/min

Example 32

(SEQ ID NO: 41)
H-Tyr-Aib-Glu-Gly-Thr-αMePhe-Thr-Ser-Asp-Lys (-Gly-Gly-Gly-Gly-Oda)-Aib-Ile-Aib-Leu-Glu-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.115 meq/g, 108.3 mg) prepared by an approach similar to Reference Example 8 was weighed into a reaction tube, and swollen with NMP. After removal of NMP by filtration, Boc-Tyr(tBu)-OH (33.7 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 104.3 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Aib-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 104.3 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 12.0 mg of a white powder.

Mass spectrometry, (M+H)$^+$ 4761.3 (Calculated: 4760.6)
HPLC elution time: 14.5 min
Elution Condition:
  Column: YMC Triart C8 (100×4.6 mm I.D.)
  Eluent: using Solution A: 0.1% TFA-water, Solution B: 0.1% TFA-containing acetonitrile, A/B: 80/20-30/70 linear concentration gradient elution (25 min).
  Flow rate: 1.0 mL/min

Example 33

(SEQ ID NO: 42)
Me-Tyr-Aib-Glu-Gly-Thr-αMePhe-Thr-Ser-Asp-Lys (-Gly-Gly-Gly-Gly-Pal)-Aib-Ile-Aib-Leu-Glu-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.115 meq/g, 108.3 mg) prepared by an approach similar to Reference Example 8 was weighed into a reaction tube, and swollen with NMP. After removal of NMP by filtration, Boc-NMeTyr(tBu)-OH (35.1 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 µL) of Pal-OSu (35.4 mg) and DIPEA (17.4 µL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 108.5 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Aib-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 108.5 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 12.0 mg of a white powder.

Mass spectrometry, (M+H)$^+$ 4717.4 (Calculated: 4716.6)
HPLC elution time: 16.6 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 34

(SEQ ID NO: 43)
Me-Tyr-Aib-Glu-Gly-Thr-αMePhe-Thr-Ser-Asp-Lys (-Gly-Gly-Gly-Gly-Oda)-Aib-Ile-Aib-Leu-Glu-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Aib-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.115 meq/g, 108.3 mg) prepared by an approach similar to Reference Example 8 was weighed into a reaction tube, and swollen with NMP. After removal of NMP by filtration, Boc-NMeTyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 117.9 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Aib-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 117.9 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 8.6 mg of a white powder.

Mass spectrometry, (M+H)$^+$ 4775.3 (Calculated: 4774.7)
HPLC elution time: 14.5 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 35

(SEQ ID NO: 44)
H-Tyr-Aib-Glu-Gly-Thr-αMePhe-Thr-Ser-Asp-Lys (-Gly-Gly-Gly-Gly-Pal)-Ala-Ile-Aib-Leu-Glu-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ala-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.116 meq/g, 108.1 mg) prepared by an approach similar to Reference Example 8 was weighed into a reaction tube, and swollen with NMP. After removal of NMP by filtration, Boc-Tyr(tBu)-OH (33.7 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M Oxyma-Pure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 µL) of Pal-OSu (35.4 mg) and DIPEA (17.4 µL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 120.1 mg of Boc-Tyr (tBu)-Aib-Glu(OtBu)-Gly-Thr(tBu)-αMePhe-Thr(tBu)-Ser (tBu)-Asp(OtBu)-Lys(-Gly-Gly-Gly-Gly-Pal)-Ala-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr (tBu)-Sieber amide resin.

To 120.1 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 10.9 mg of a white powder.

Mass spectrometry, (M+H)$^+$ 4689.1 (Calculated: 4688.6)

HPLC elution time: 16.5 min

Elution Condition:

Column: YMC Triart C8 (100×4.6 mm I.D.)

Eluent: using Solution A: 0.1% TFA-water, Solution B: 0.1% TFA-containing acetonitrile, A/B: 80/20-30/70 linear concentration gradient elution (25 min).

Flow rate: 1.0 mL/min

Example 36

(SEQ ID NO: 45)
H-Tyr-Aib-Glu-Gly-Thr-αMePhe-Thr-Ser-Asp-Lys (-Gly-Gly-Gly-Gly-Oda)-Ala-Ile-Aib-Leu-Glu-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser (tBu)-Asp(OtBu)-Lys(ivDde)-Ala-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.116 meq/g, 108.1 mg) prepared by an approach similar to Reference Example 8 was weighed into a reaction tube, and swollen with NMP. After removal of NMP by filtration, Boc-Tyr(tBu)-OH (33.7 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 107.9 mg of Boc-Tyr(tBu)-Aib-Glu(OtBu)-Gly-Thr(tBu)-αMePhe-Thr (tBu)-Ser(tBu)-Asp(OtBu)-Lys(-Gly-Gly-Gly-Gly-Oda (OtBu))-Ala-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His (Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 107.9 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 9.2 mg of a white powder.

Mass spectrometry, (M+H)+ 4747.3 (Calculated: 4746.6)
HPLC elution time: 14.5 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 37

(SEQ ID NO: 46)
Me-Tyr-Aib-Glu-Gly-Thr-αMePhe-Thr-Ser-Asp-Lys (-Gly-Gly-Gly-Gly-Pal)-Ala-Ile-Aib-Leu-Glu-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ala-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.116 meq/g, 108.1 mg) prepared by an approach similar to Reference Example 8 was weighed into a reaction tube, and swollen with NMP. After removal of NMP by filtration, Boc-NMeTyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 μL) of Pal-OSu (35.4 mg) and DIPEA (17.4 μL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 117.8 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Ala-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 117.8 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 11.4 mg of a white powder.

Mass spectrometry, (M+H)+ 4703.3 (Calculated: 4702.6)
HPLC elution time: 16.5 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 38

(SEQ ID NO: 47)
Me-Tyr-Aib-Glu-Gly-Thr-αMePhe-Thr-Ser-Asp-Lys (-Gly-Gly-Gly-Gly-Oda)-Ala-Ile-Aib-Leu-Glu-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ala-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.116 meq/g, 108.1 mg) prepared by an approach similar to Reference Example 8 was weighed into a reaction tube, and swollen with NMP. After removal of NMP by filtration, Boc-NMeTyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 116 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Ala-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 116 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 11.0 mg of a white powder.

Mass spectrometry, (M+H)$^+$ 4761.2 (Calculated: 4760.6)
HPLC elution time: 14.5 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 39

(SEQ ID NO: 48)
H-Tyr-Aib-Glu-Gly-Thr-αMePhe-Thr-Ser-Asp-Lys (-Gly-Gly-Gly-Gly-Pal)-Ser-Ile-Aib-Leu-Glu-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ser(tBu)-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.116 meq/g, 107.5 mg) prepared by an approach similar to Reference Example 8 was weighed into a reaction tube, and swollen with NMP. After removal of NMP by filtration, Boc-Tyr(tBu)-OH (33.7 mg), 0.5 M OxymaPure in NMP (200 µL) and diisopropylcarbodiimide (15.9 µL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 µL) and diisopropylcarbodiimide (15.9 µL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 µL) of Pal-OSu (35.4 mg) and DIPEA (17.4 µL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 124 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Ser(tBu)-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 124 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 µm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 8.9 mg of a white powder.

Mass spectrometry, (M+H)$^+$ 4705.1 (Calculated: 4704.6)
HPLC elution time: 16.6 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min

Example 40

(SEQ ID NO: 49)
H-Tyr-Aib-Glu-Gly-Thr-αMePhe-Thr-Ser-Asp-Lys (-Gly-Gly-Gly-Gly-Oda)-Ser-Ile-Aib-Leu-Glu-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ser(tBu)-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.116 meq/g, 107.5 mg) prepared by an approach similar to Reference Example 8 was weighed into a reaction tube, and swollen with NMP. After removal of NMP by filtration, Boc-Tyr(tBu)-OH (33.7 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 116.8 mg of Boc-Tyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Ser(tBu)-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 116.8 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 13.1 mg of a white powder.

Mass spectrometry, (M+H)$^+$ 4763.0 (Calculated: 4762.6)
HPLC elution time: 14.5 min
Elution Condition:
  Column: YMC Triart C8 (100×4.6 mm I.D.)
  Eluent: using Solution A: 0.1% TFA-water, Solution B: 0.1% TFA-containing acetonitrile, A/B: 80/20-30/70 linear concentration gradient elution (25 min).
  Flow rate: 1.0 mL/min

Example 41

(SEQ ID NO: 50)
Me-Tyr-Aib-Glu-Gly-Thr-αMePhe-Thr-Ser-Asp-Lys (-Gly-Gly-Gly-Gly-Pal)-Ser-Ile-Aib-Leu-Glu-Lys-

Gln-Arg-Gln-Iva-Glu-Phe-Val-Arg-His-Leu-Leu-Asn-

Lys-Aib-Thr-Arg-Gln-Arg-Tyr-NH$_2$

H-Aib-Glu(OtBu)-Gly-Thr(tBu)-αMePhe-Thr(tBu)-Ser(tBu)-Asp(OtBu)-Lys(ivDde)-Ser(tBu)-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.116 meq/g, 107.5 mg) prepared by an approach similar to Reference Example 8 was weighed into a reaction tube, and swollen with NMP. After removal of NMP by filtration, Boc-NMeTyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. Fmoc-Gly-Gly-Gly-OH (41.1 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. A NMP solution (200 μL) of Pal-OSu (35.4 mg) and DIPEA (17.4 μL) was added to the obtained resin, and the mixture was then shaken overnight. The reaction solution was filtered off, and the resin was then washed with NMP 6 times. After confirmation of negativity in the Kaiser test, the resin was washed with MeOH, and dried under reduced pressure to give 104.3 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Pal)-Ser(tBu)-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 104.3 mg of the obtained resin was added 1 mL of TFA:m-cresol:thioanisole:ethanedithiol:H₂O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 57/43-47/53 linear concentration gradient elution (60 min)]. The fractions containing the object product were collected and freeze-dried to give 11.3 mg of a white powder.

Mass spectrometry, $(M+H)^+$ 4719.3 (Calculated: 4718.6)
HPLC elution time: 16.6 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Example 42

(SEQ ID NO: 51)
Me-Tyr-Aib-Glu-Gly-Thr-αMePhe-Thr-Ser-Asp-Lys (-Gly-Gly-Gly-Gly-Oda)-Ser-Ile-Aib-Leu-Glu-Lys-

Gln-Arg-Gln-Iva-Glu-Phe-Val-Arg-His-Leu-Leu-Asn-

Lys-Aib-Thr-Arg-Gln-Arg-Tyr-NH₂

H-Aib-Glu(OtBu)-Gly-Thr(tBu)-αMePhe-Thr(tBu)-Ser(tBu)-Asp(OtBu)-Lys(ivDde)-Ser(tBu)-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin (0.116 meq/g, 107.5 mg) prepared by an approach similar to Reference Example 8 was weighed into a reaction tube, and swollen with NMP. After removal of NMP by filtration, Boc-NMeTyr(tBu)-OH (35.1 mg), 0.5 M OxymaPure in NMP (200 μL) and diisopropylcarbodiimide (15.9 μL) were successively added to the resin, and then the mixture was shaken overnight. The reaction solution was filtered off, and the resin was then washed with NMP 6 times. After confirmation of negativity in the Kaiser test, a NMP solution of 2% hydrazine was added to the obtained resin, and the mixture was shaken for 3 hours. The solution was filtered off, and a NMP solution of 2% hydrazine was then added thereto again, and the mixture was shaken overnight. The reaction solution was filtered off, and the resin was then washed with NMP 6 times. Fmoc-Gly-OH (29.7 mg), 0.5 M OxymaPure in NMP (200 μL) and diisopropylcarbodiimide (15.9 μL) were successively added to the obtained resin, and then the mixture was shaken overnight. The reaction solution was filtered off, and the resin was then washed with NMP 6 times. After confirmation of negativity in the Kaiser test, a NMP solution of 20% piperidine was added thereto, and the mixture was shaken for 1 minute. The solution was filtered off, and a NMP solution of 20% piperidine was then added thereto again, and the mixture was shaken for 20 minutes. The solution was filtered off, and the resin was then washed with NMP 10 times. This Fmoc amino acid condensation-Fmoc deprotection cycle was repeated to successively condense Gly-Gly-Gly and Oda(OtBu). The resin was washed with MeOH, and then dried under reduced pressure to give 109.1 mg of Boc-NMeTyr(tBu)-Aib-Glu(OtBu)-Gly-Thr(tBu)-αMePhe-Thr(tBu)-Ser(tBu)-Asp(OtBu)-Lys(-Gly-Gly-Gly-Gly-Oda(OtBu))-Ser(tBu)-Ile-Aib-Leu-Glu(OtBu)-Lys(Boc)-Gln(Trt)-Arg(Pbf)-Gln(Trt)-Iva-Glu(OtBu)-Phe-Val-Arg(Pbf)-His(Trt)-Leu-Leu-Asn(Trt)-Lys(Boc)-Aib-Thr(tBu)-Arg(Pbf)-Gln(Trt)-Arg(Pbf)-Tyr(tBu)-Sieber amide resin.

To 109.1 mg of the obtained resin was added 1 mL of TFA:m-cresol:thioanisole:ethanedithiol:H₂O:triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using YMC-Actus Triart Prep C8 S-10 μm 20 nm column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 10.5 mg of a white powder.

Mass spectrometry, $(M+H)^+$ 4777.2 (Calculated: 4776.6)
HPLC elution time: 14.5 min
Elution Condition:
Column: YMC Triart C8 (100×4.6 mm I.D.)
Eluent: using Solution A: 0.1% TFA-water, Solution B: 0.1% TFA-containing acetonitrile, A/B: 80/20-30/70 linear concentration gradient elution (25 min).
Flow rate: 1.0 mL/min Test Example 1

Evaluation of Agonist Activity Against Human NPY2R, Human GIPR, and Human GLP-1R Using Change in Intracellular cAMP Concentration as Index
(1) Construction of Human NPY2R Gene-Expressing Cell The human NPY2R gene having a sequence identical to the sequence of GenBank Accession No. AC104407 was cloned into pAKKO1114 vector to prepare hNPY2R/pAKKO1114. Next, pGL4.29 (Promega) was introduced to CHO-K1 cells, which were then screened with hygromycin to construct Cre-luc reporter cells. These cells were cotransfected with hNPY2R/pAKKO1114 and pcDNA3.1 (Life Technologies Corp.), and the cells were screened with geneticin. Next, a cell line induced to express luciferase, i.e., pAKKO1114/hNPY2R#481 No. 88 cells, were selected from the obtained transformants by the addition of human PYY (3-36).
(2) Construction of Human GIPR Gene-Expressing Cell The human GIPR gene having a sequence identical to the sequence of GenBank Accession No. U39231 was cloned into pMSRα-neo vector to prepare hGIPR/pMSRα-neo. This vector was introduced to the Cre-luc reporter cells obtained in (1) to obtain transformants. Next, a cell line induced to express luciferase, i.e., hGIPR/CHO-K1 cells, were selected from the obtained transformants by the addition of GIP.

(3) Construction of Human GLP-1R Gene-Expressing Cell

The human GLP-1R gene having a sequence identical to the sequence of GenBank Accession No. NM_002062 was cloned into pIRESneo3 vector (Clontech Laboratories, Inc.) to prepare hGLP-1R/pIRESneo3. This vector was introduced to the Cre-luc reporter cells obtained in (1) to obtain transformants. Next, a cell line induced to express luciferase, i.e., hGLP-1R/Crel cells, were selected from the obtained transformants by the addition of human GLP-1(7-37) peptide.

(4) Reporter Assay of Human NPY2R Gene

The pAKKO1114/hNPY2R#481 No. 88 cells were inoculated at a cell density of 25 μL/well (5,000 cells/well) to a 384-well white plate (Corning, 3570), and cultured overnight in Ham F12 medium containing 10% fetal bovine serum, 100 U/mL penicillin and 100 μg/mL streptomycin in a $CO_2$ incubator of 37° C. On the next day, the medium was removed, and an assay medium (Ham F12 medium containing 0.1% BSA, 100 U/mL penicillin and 100 μg/mL streptomycin) containing forskolin (final concentration: 1.2 μM) was added at a concentration of 25 μL/well to the cells. Next, an assay medium containing a test compound was added at a concentration of 5 μL/well to the cells, and the resultant cells were incubated for 4 hours in a $CO_2$ incubator of 37° C. to give the final concentration of 1 μM. SteadyGlo (Promega) was added thereto at a concentration of 30 μL/well, and the mixture was left standing for 20 minutes with light shielded. The luciferase activity was measured using a plate reader Envision (PerkinElmer). The luciferase activity from the addition of DMSO was defined as 100%, and the luciferase activity from the addition of 1 μM human PYY(3-36) instead of the test compound was defined as 0%. The NPY2R agonist activity was calculated with a decrease in intracellular cAMP concentration as an index. The results are shown in Table 2.

(5) Reporter Assay of Human GIPR and GLP-1R Genes

The hGIPR/CRE-LUC/CHO-K1 cells or the hGLP-1R/Crel cells were inoculated at a cell density of 25 μL/well (5,000 cells/well) to a 384-well white plate (Corning, 3570), and cultured overnight in Ham F12 medium containing 10% fetal bovine serum, 100 U/mL penicillin and 100 μg/mL streptomycin in a $CO_2$ incubator of 37° C. On the next day, a medium containing a test compound was added at a concentration of 5 μL/well to the cells, and the resultant cells were incubated for 4 hours in a $CO_2$ incubator of 37° C. to give the final concentration of 1 μM. SteadyGlo (Promega) was added thereto at a concentration of 30 μL/well, and the mixture was shaken with light shielded. After 30 minutes, the luciferase activity was measured using a plate reader Envision (PerkinElmer). For the GIPR agonist activity, the luciferase activity in the presence of 10 μM GIP was defined as 100%, and the luciferase activity from the addition of DMSO instead of the test compound was defined as 0%. The GIPR agonist activity was calculated with a rise in intracellular cAMP concentration as an index. The results are shown in Table 2.

For the GLP-1R agonist activity, assay similar to above was conducted using the hGLP-1R/Crel cells. The luciferase activity in the presence of 10 μM GLP-1 was defined as 100%, and the luciferase activity from the addition of DMSO instead of the test compound was defined as 0%. The GLP-1R agonist activity was calculated with a rise in intracellular cAMP concentration as an index. The results are shown in Table 2.

TABLE 2

| | Agonist activity ($EC_{50}$) | | Unit: M |
|---|---|---|---|
| Example | hGLP-1R | hGIPR | hY2R |
| 1 | 1.4E-11 | 3.5E-11 | 3.1E-11 |
| 2 | 1.1E-10 | 7.1E-11 | 2.1E-09 |
| 3 | 3.8E-10 | 3.5E-10 | 2.2E-10 |
| 4 | 6.1E-10 | 4.1E-10 | 1.3E-09 |
| 5 | 1.3E-10 | 9.3E-11 | 1.2E-10 |
| 6 | 1.5E-09 | 2.9E-10 | 1.0E-09 |
| 7 | 8.2E-11 | 6.8E-11 | 1.0E-10 |
| 8 | 3.2E-10 | 2.2E-10 | 2.1E-09 |
| 9 | 8.3E-11 | 6.8E-11 | 1.0E-10 |
| 10 | 1.4E-09 | 2.5E-10 | 2.0E-09 |
| 11 | 7.9E-11 | 6.6E-11 | 9.9E-11 |
| 12 | 1.2E-09 | 2.6E-10 | 3.0E-09 |
| 13 | 1.0E-10 | 7.4E-11 | 1.0E-10 |
| 14 | 4.4E-09 | 1.7E-10 | 3.2E-09 |
| 15 | 5.0E-11 | 5.6E-11 | 4.8E-11 |
| 16 | 4.7E-10 | 1.1E-10 | 2.6E-09 |
| 17 | 4.9E-11 | 5.0E-11 | 8.1E-11 |
| 18 | 1.9E-09 | 9.1E-11 | 2.4E-09 |
| 19 | 6.0E-11 | 4.4E-11 | 6.4E-11 |
| 20 | 9.4E-11 | 1.0E-09 | 1.5E-09 |
| 21 | 6.9E-11 | 5.1E-11 | 6.8E-11 |
| 22 | 2.5E-09 | 7.7E-10 | 1.4E-09 |
| 23 | 1.3E-10 | 9.1E-11 | 5.9E-11 |
| 24 | 1.3E-09 | 6.1E-10 | 1.3E-09 |
| 25 | 7.3E-11 | 4.8E-11 | 2.0E-11 |
| 26 | 4.5E-09 | 3.8E-10 | 1.2E-09 |
| 27 | 4.2E-11 | 4.1E-11 | 3.8E-11 |
| 28 | 7.8E-11 | 7.4E-11 | 2.4E-09 |
| 29 | 4.3E-11 | 3.8E-11 | 3.0E-11 |
| 30 | 1.5E-10 | 7.4E-11 | 3.3E-09 |
| 31 | 6.1E-11 | 4.9E-11 | 5.7E-11 |
| 32 | 2.5E-10 | 5.2E-10 | 2.7E-09 |
| 33 | 1.3E-10 | 8.2E-11 | 6.7E-11 |
| 34 | 1.1E-09 | 5.3E-10 | 1.5E-09 |
| 35 | 4.5E-11 | 4.2E-11 | 2.3E-11 |
| 36 | 5.3E-10 | 3.6E-10 | 1.1E-09 |
| 37 | 3.6E-11 | 4.0E-11 | 2.6E-11 |
| 38 | 2.3E-09 | 4.0E-10 | 1.7E-09 |
| 39 | 5.3E-11 | 4.1E-11 | 4.1E-11 |
| 40 | 2.4E-10 | 1.7E-10 | 1.6E-09 |
| 41 | 4.8E-11 | 5.2E-11 | 4.9E-11 |
| 42 | 1.3E-09 | 2.5E-10 | 2.6E-09 |

Test Example 2

Evaluation of Feeding Suppressive Action after Single-Dose Administration

The feeding suppressive activity of a test compound was examined by the method described below.

The test compound was dissolved at a concentration of 30 or 100 nmol/2 mL in a solvent (10% DMSO-containing physiological saline). The test compound solution was subcutaneously administered at a dose of 2 mL/kg to the back of each male C57BL/6J mouse at 8-9 weeks of age (20-26° C., allowed to take food and water ad libitum; raised in the 12-hour bright-12-hour dark cycle). The administration was performed once a day for 3 days. After the administration, the mouse was individually raised in a rearing cage, and given previously weighed food; food consumption for 3 days after the start of administration was measured. The food consumption was calculated by subtracting the amount of remaining food from the weight of the food given on the day of the start of administration. When the food consumption of a control group receiving administration of the solvent alone was regarded as a suppression rate of 0%, the feeding suppressive activity of each test compound was evaluated on the basis of 3-days cumulative food consumption after the start of administration. The food intake suppression rate (%) of the test compound was defined as (Food consumption of the control group−Food consumption of the test compound-administered group)/Food consumption of the control group×100.

As shown in Table 3, the compound of the present invention has a food intake suppressive action.

TABLE 3

| Example | Rate of feeding suppression (%) | Test compound dose (nmol/kg) |
| --- | --- | --- |
| 1 | −37.1 | 30 |
| 2 | −77.3 | 100 |
| 7 | −37.6 | 30 |
| 11 | −48.1 | 30 |
| 13 | −41.0 | 30 |
| 15 | −41.2 | 30 |
| 19 | −37.0 | 30 |
| 21 | −27.9 | 30 |
| 25 | −41.7 | 30 |
| 27 | −41.6 | 30 |
| 29 | −43.7 | 30 |
| 31 | −56.8 | 30 |
| 32 | −51.0 | 30 |
| 33 | −58.4 | 30 |
| 34 | −39.9 | 30 |
| 35 | −52.6 | 30 |
| 37 | −54.9 | 30 |
| 39 | −49.6 | 30 |
| 41 | −52.1 | 30 |

Test Example 3

Repeated Dosing Studies in Diet-Induced Obese (DIO) Mice
Repeated Dosing Study

Male DIO C57BL/6J mice (40 weeks old) were divided into the groups based on the data of body weight, food intake, and plasma parameters. Vehicle or the compounds (P41) of Example 41 was subcutaneously administered once a day for 4 weeks. Body weight and food intake were monitored during the study. Compounds were dissolved in 10% DMSO/saline. After the study, blood was collected and plasma parameters were measured. At day 29, body composition was measured by EchoMRI (Hitachi Aloka Medical, Ltd., Japan) and the animals were sacrificed. For hematoxylin and eosin (HE) staining, livers were dissected from DIO mice after 4 weeks drug administration described in the above body-weight studies section. Livers were fixed in 4% paraformaldehyde, embedded in paraffin, sectioned, and stained with HE. After processing, the sections were mounted and then examined via light microscopy (NanoZoomer, Hamamatsu Photonics).

Quantitative Real-Time PCR

Total RNA was isolated from the liver using QIAzol reagent (QIAGEN Japan, Tokyo, Japan) and cDNA was synthesized using High-Capacity cDNA Reverse Transcription Kit (Applied Biosystems, CA, USA). Quantitative RT-PCR was performed using the ABI Prism 7900 Sequence Detection System with EXPRESS qPCR Super Mix (Thermo Fisher Scientific Inc. MA. USA). Mixtures of primers and probes (Applied Biosystems) were used for the detection of mRNA (Table 4). The expression levels were normalized to those of beta-actin and Peptidyl isomerase A.

TABLE 4

| gene | symbol |
| --- | --- |
| Peptidylprolyl isomerase A | PPIA |
| β-Actin | ACTB |
| type I collagen α1 | Col1a |
| Carnitine palmitoyltransferase 1A | CPT1 |
| Tissue inhibitor of metallopeptidase inhibitor 1 | Timp1 |
| C-C Motif Chemokine Ligand 2 | Ccl2 |
| Interleukin-1β | IL-1b |
| Transforming growth factor β | TGFb |
| Tumor necrosis factor α | TNFa |
| Matrix metallopoteinase 2 | MMP2 |

Measurement

Plasma glucose, triglyceride (TG), total cholesterol (TC), aspartate aminotransferase (AST), and alanine aminotransferase (ALT) were analyzed by Autoanalyzer 7180 (Hitachi High-Technologies Corporation, Japan). Blood glycated hemoglobin (GHb) was measured with the automated GHb analyzers (HLC-723G8, Tosoh, Tokyo, Japan). Liver triglyceride content was measured as follows: a piece of tissue was homogenized in saline and lipid was extracted by the addition of hexane:isopropanol (3:2) solution. The lipid phase was collected, dried and then dissolved in isopropanol. The concentration of triglyceride was measured by Triglyceride E-test (Wako Pure Chemical Industries, Ltd, Japan) and triglyceride content per g liver was calculated. Plasma insulin was measured with ELISA Assay kit (Shibayagi Co. Ltd., Japan).

Anti-Obesity Effect of P41 in DIO Mice

Four-week repeated dosing study in DIO mice was conducted to evaluate anti-obesity effect of P41. Daily injection of P41 at the dose of 3, 10 and 30 nmol/kg decreased body weight by 14.6%, 30.0% and 37.1% compared with vehicle group, respectively (FIG. 1a). Similar reduction of cumulative food intake was observed in P41 treated group in a dose-dependent manner (FIG. 1b). By body composition analysis using EchoMRI, the drastic decrease in fat mass was observed in a dose-dependent manner in contrast to subtle decrease in lean mass in P41 treated group (FIG. 1c, d). In line with the observation, P41 significantly decreased inguinal, mesenteric and epididymal fat pad weight in a dose-dependent manner (FIG. 1e). In biochemical parameters, TC and plasma insulin levels were significantly and dose-dependently improved in all P41-treated groups. Regarding the effect on hepatic steatosis, liver weight (FIG. 1f), liver TG content (FIG. 1g), plasma AST and ALT (Table 5) were drastically decreased by P41 in a dose-dependent manner. Reduction of hepatic lipid droplet was observed by HE staining of liver slices (FIG. 1h). Hepatic gene expression analysis revealed that the genes related to fibrosis such as Tissue inhibitor of metallopeptidase inhibitor 1 (Timp1), type I collagen α 1 (Col1α) and inflammation such as C—C motif chemokine ligand 2 (CCl2) tended to decrease and inhibitor of fibrosis such as matrix metallopeptidase 2 (MMP2) tended to increase (FIG. 1i). Collectively, 4-week treatment with P41 showed potent anti-obesity effect with improvement of hepatic steatosis in DIO mice.

TABLE 5

|  | TG (mg/dL) | TC (mg/dL) | AST (U/L) | ALT (U/L) | Insulin (ng/mL) |
|---|---|---|---|---|---|
| vehicle | 53.7 ± 19.9 | 311.3 ± 24.3 | 352.8 ± 66.1 | 319.8 ± 80.7 | 15.6 ± 10.9 |
| P41 3 nmol/kg | 50.5 ± 16.2 | 253.6 ± 11.9 ### | 170.0 ± 37.2 *** | 94.2 ± 32.3 ** | 4.9 ± 2.9 * |
| P41 10 nmol/kg | 62.2 ± 16.1 | 189.5 ± 22.1 ### | 88.8 ± 11.7 *** | 35.6 ± 9.7 *** | 3.7 ± 2.7 ** |
| P41 30 nmol/kg | 50.2 ± 6.6 | 173.2 ± 16.4 ### | 90.2 ± 10.3 *** | 37.5 ± 7.7 *** | 5.2 ± 2.1 ** |

\* $p < 0.025$,
\*\* $p < 0.005$,
\*\*\* $p < 0.0005$ vs. vehicle by Shirley-Williams test.
$p < 0.0005$ vs. vehicle by Williams' test.
Data represent mean ± SD (N = 6).

Test Example 4

Repeated Dosing Studies in Ob/Ob Mice

Male ob/ob mice (9 weeks old) were divided into the groups based on the data of body weight, food intake, and plasma parameters. Vehicle or P41 was subcutaneously administered once a day for 4 weeks. Body weight and food intake were monitored during the study. Compounds were dissolved in 10% DMSO/saline. After the study, blood was collected and plasma parameters were measured. At day 29, the animals were sacrificed.

Measurement

Plasma glucose, triglyceride (TG), total cholesterol (TC), aspartate aminotransferase (AST), and alanine aminotransferase (ALT) were analyzed by Autoanalyzer 7180 (Hitachi High-Technologies Corporation, Japan). Blood glycated hemoglobin (GHb) was measured with the automated GHb analyzers (HLC-723G8, Tosoh, Tokyo, Japan). Liver triglyceride content was measured as follows: a piece of tissue was homogenized in saline and lipid was extracted by the addition of hexane:isopropanol (3:2) solution. The lipid phase was collected, dried and then dissolved in isopropanol. The concentration of triglyceride was measured by Triglyceride E-test (Wako Pure Chemical Industries, Ltd, Japan) and triglyceride content per g liver was calculated. Plasma insulin was measured with ELISA Assay kit (Shibayagi Co. Ltd., Japan).

Anti-Obesity and Anti-Diabetes Effect of P41 in Ob/Ob Mice

Figure 2:
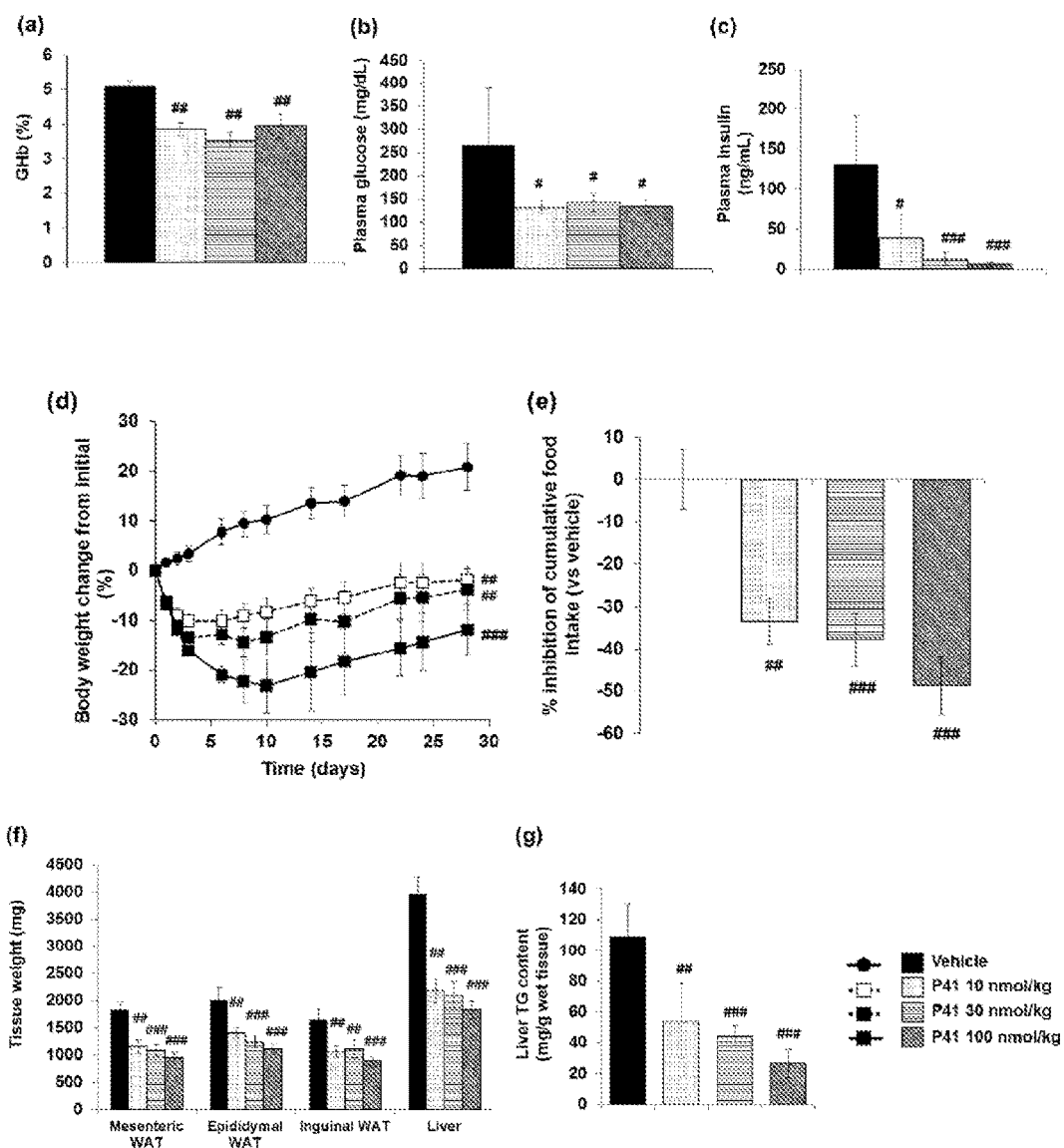
FIG. 2 shows the antiobesity and antidiabetic actions of P41 in ob/ob mice. Each compound was subcutaneously administered to each mouse once a day for 4 weeks.

Next, we measured the effect of P41 on anti-obesity and anti-diabetes in ob/ob mice. After 4-week treatment with P41 at the dose of 10, 30 and 100 nmol/kg, the compound showed significant decrease in GHb (FIG. 2a) and plasma glucose levels (FIG. 2b). Dose-dependent decrease in plasma insulin levels were also observed in P41 treated group (FIG. 2c). Regarding the anti-obesity effect, P41 showed dose-dependent body weight and cumulative food intake reduction more potent than vehicle (FIG. 2d, e). P41 decreased liver and mesenteric, epididymal, and inguinal adipose tissue weight, and liver TG content in a dose-dependent manner in consistent with body weight reduction (FIG. 2f, g). In biochemical parameters, plasma TC, TG, AST and ALT were significantly and dose-dependently improved in P41 treated groups (Table 6).

TABLE 6

Plasma biochemical parameter after 4-week treatment in ob/ob mice

|  | TG (mg/dL) | TC (mg/dL) | AST (U/L) | ALT (U/L) |
|---|---|---|---|---|
| Vehicle | 123.2 ± 59.1 | 253 9 ± 33.6 | 312.4 ± 85 3 | 397.8 ± 94.2 |
| P41 10 nmol/kg | 52.4 ± 13.0 ## | 137.0 ± 12.7 ## | 82.3 ± 25.0 ## | 50.6 ± 23.8 ## |
| P41 30 nmol/kg | 51.6 ± 14.2 ## | 128 8 ± 12.4 ## | 83.5 ± 21.5 ## | 38.3 ± 9.3 ## |
| P41 100 nmol/kg | 46.9 ± 12.9 ## | 136.8 ± 6.1 ## | 77.7 ± 13.1 ## | 41.6 ± 10.1 ## |

\# $p < 0.025$,
\#\# $p < 0.005$,
\#\#\# $p < 0.0005$ vs. vehicle (Shirley-Williams test).
Data represent mean ± SD (N = 5 or 7).
N = 5 for the vehicle-administered group.
N = 7 for the P41-administered group.

Test Example 5

Repeated Administration of P41 in KKA$^y$ Mice

Male KKA$^y$ mice (10 weeks old) were divided into the groups based on the data of body weight, food intake, glycated hemoglobin (GHb), and plasma parameters. P41 was subcutaneously administered once a day for 4 weeks. Compounds were dissolved in 10% DMSO/saline. Body weight and food intake were monitored during the study. After the study, blood was collected and GHb and plasma parameters were measured. The animals were sacrificed, and the liver and the adipose tissues were dissected and weighed. Lipid was extracted from a piece of liver tissue and liver triglyceride (TG) content was measured.

Measurement

Plasma glucose and TG were measured by Autoanalyzer 7180 (Hitachi High-Technologies Corporation, Japan). Blood GHb was measured with the automated GHb analyzers (HLC-723G8, Tosoh, Tokyo, Japan). Plasma insulin was measured with ELISA Assay kit (Shibayagi Co. Ltd., Japan). Liver TG content was measured as follows: a piece of tissue was homogenized in saline and lipid was extracted by the addition of hexane:isopropanol (3:2) solution. The lipid phase was collected, dried and then dissolved in isopropanol. The concentration of TG was measured by Triglyceride E-test (Wako Pure Chemical Industries) and TG content per g liver was calculated.

4W Repeated Dose Study of P41 in Male KKA$^y$ Mice.

Figure 3:
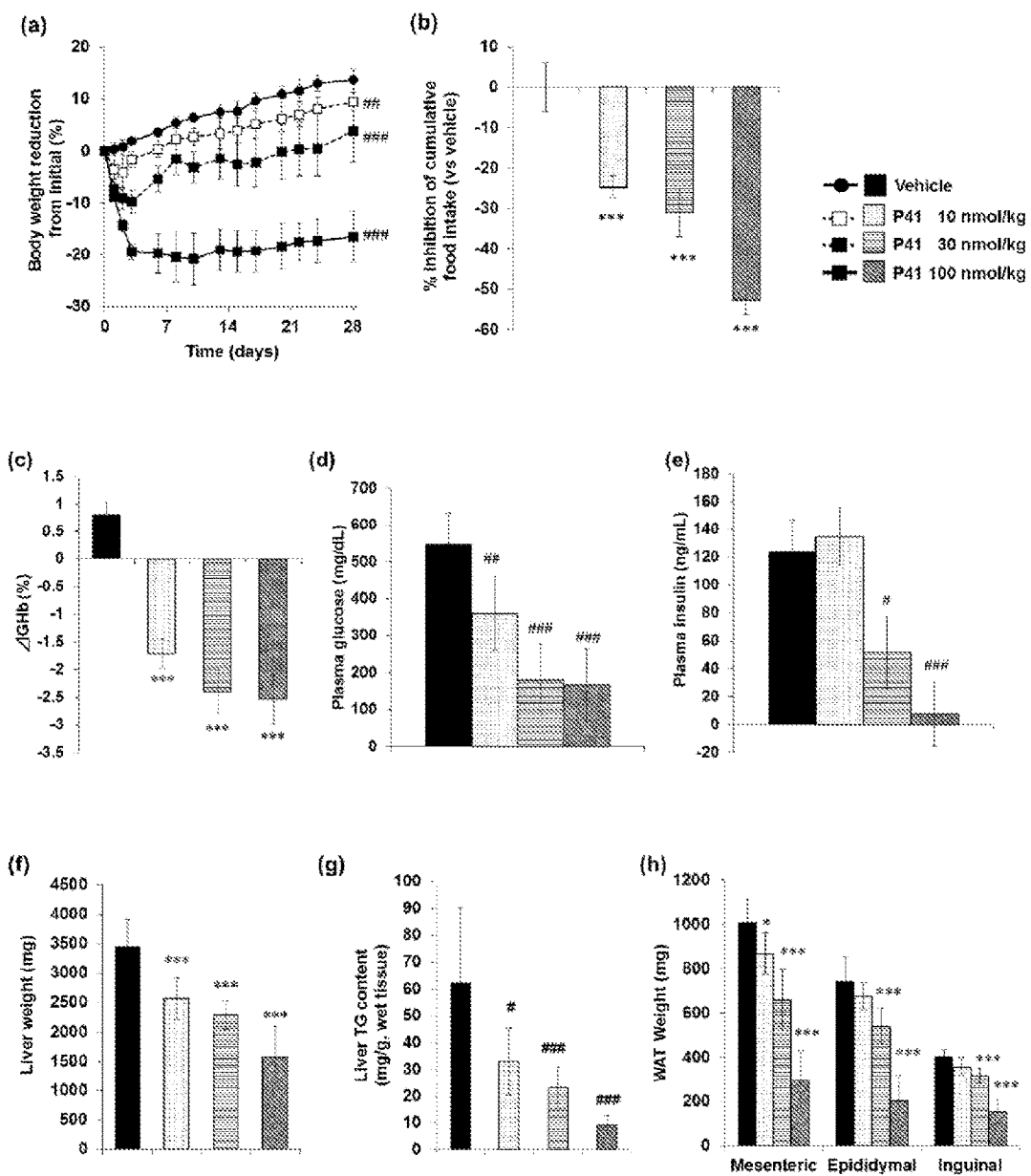
FIG. 3 shows the antiobesity and antidiabetic actions of P41 in male KKA$^y$ mice. Each compound was subcutaneously administered to each mouse once a day for 4 weeks.
Figure 4:
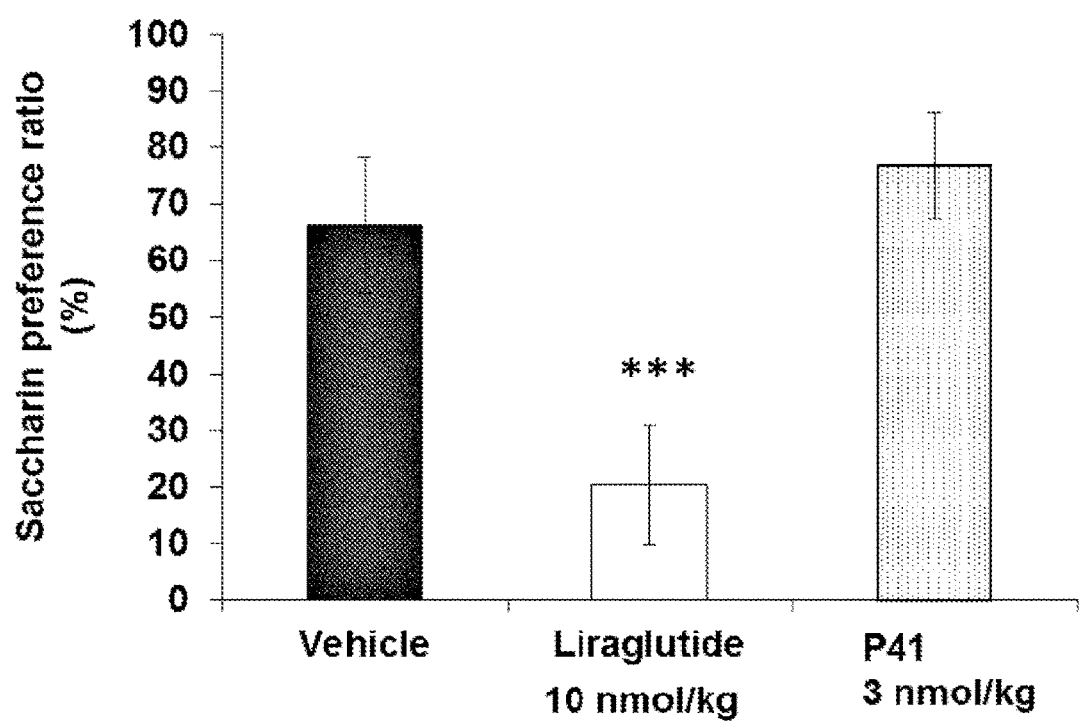
FIG. 4 shows the action of P41 on conditioned taste aversion. Each mouse received 0.1% saccharin paired with the compound twice a week. Two days after second conditioning, 0.1% saccharin and tap water were presented to the mice for 3 hours, and the amounts of intake of both fluids were measured to calculate saccharin preference ratio. *** $p<0.001$ vs. vehicle (Dunnett's test). Data represent mean±SD (N=7)
Figure 5:
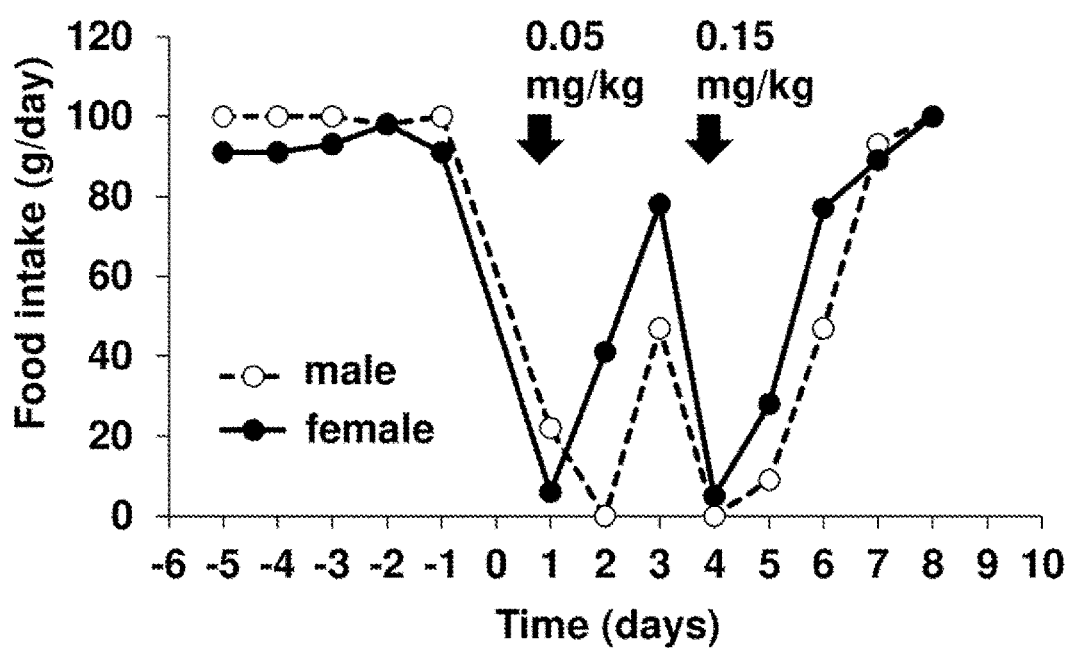
FIG. 5 shows the feeding suppressive effect of P41 in cynomolgus monkeys. Normal chow diet was served approximately 8 hours after dosing. Vomiting was not observed for 24 hours after dosing. N=2 (male: 1, female: 1)

Four-week repeated dosing study in KKA$^y$ mice was conducted to evaluate anti-obesity and anti-diabetic effect of P41. Daily subcutaneous injection of P41 at the dose of 10, 30 and 100 nmol/kg decreased body weight by 4.2, 9.8 and 30.1% compared with vehicle group, respectively (FIG. 3a). Similar dose-dependent reduction of cumulative food intake was observed in P41 treated group (FIG. 3b). Regarding the anti-diabetic effects, P41 showed dose-dependent and significant decrease in GHb, PG and plasma insulin levels (FIG. 3c-e). Comparable reduction of liver tissue weight was observed in P41 treated groups in consistent with body weight loss (FIG. 3f).

TABLE 7

Plasma biochemical parameters in KKA$^y$ mice

| | vehicle | P41 10 nmol/kg | P41 30 nmol/kg | P41 100 nmol/kg |
|---|---|---|---|---|
| TG (mg/dL) | 564.9 ± 159.8 | 357.1 ± 76.9 # | 210.1 ± 53.3 ### | 138.1 ± 54.4 ### |
| TC (mg/dL) | 169.7 ± 27.5 | 139.3 ± 19.0 | 155.9 ± 20.1 | 131.4 ± 14.0 ** |
| AST (U/L) | 50.6 ± 6.3 | 53.4 ± 11.9 | 48.9 ± 8.6 | 52.6 ± 7.3 |
| ALT (U/L) | 27.1 ± 7.9 | 31.3 ± 9.7 | 24.9 ± 2.1 | 21.7 ± 7.6 |

** $p < 0.005$ vs vehicle by William's test.
$p < 0.025$,
$p < 0.0005$ vs vehicle by Shirley-William's test.
Data represent mean ± SD (N = 7).

Test Example 6

Conditioned Taste Aversion (CTA) Test

Male C57BL/6J (9 weeks old) mice were habituated to time-restricted bottled water supply (2-3 hours/day) and subcutaneous injection of saline for 1 week. Mice were divided into the groups based on the data of body weight and water intake. CTA test was performed according to the following protocol. On day 1 for the first conditioning, mice were given 0.1% sodium saccharin solution to drink for 3 hours. Ten-minutes after supplying the saccharin solution, vehicles, liraglutides and P41 were administered subcutaneously. Liragutides have GLP-1 receptor coagonist activity. On day 2, mice were given tap water for 3 hours and subcutaneous injection of saline after water supply. On day 3, the second conditioning was conducted as the same procedure used on day 1. On day 4, mice were given tap water for 3 hours without subcutaneous injection. On day 5, both tap water and saccharin solution were supplied to mice for 3 hours without subcutaneous injection and the intake of each fluid was measured. Saccharin preference ratio (%) was calculated according to the following equation: {(amount of saccharin intake)/(amount of saccharin intake+amount of water intake)}×100.

Conditioned Taste Aversion in Mice

We conducted CTA test for the evaluation of emetic effects. While liraglutide at the dose of 10 nmol/kg significantly decreased saccharin preference ratio, indicating the induction of CTA, P41 did not induce CTA at 3 nmol/kg; the dose which showed more potent anti-obesity effect than that of liraglutide in DIO mice (FIG. 7).

TABLE 8

The effect of P41 on conditioned taste aversion.

| | Saccharin preference ratio (%) |
|---|---|
| Vehicle | 66.2 ± 12.0 |
| Liraglutide (10 nmol/kg) | 20.4 ± 10.5 *** |
| P41 (3 nmol/kg) | 76.8 ± 9.5 |

*** $p < 0.001$ vs. vehicle by Dunnett's test.
Data represent mean ± SD (N = 7).

Test Example 7

Study in Cynomolgus Monkeys

One male and one female cynomolgus monkeys (age: 4 years old, body weight: 3.9 kg in male, 2.7 kg in female) were used. The monkeys were housed in individual cages with a 12 hr:12 hr light-dark schedule at 22-27° C., and given 100 g of pellet diet (Oriental Yeast Co. Ltd) once daily. The diet was supplied after completion of the clinical observation at 8 hour post dose on the days of dosing. On other days during the experimental period, the diet was supplied each day after the completion of examinations and the remaining diet was withdrawn on the following morning. P41 was dissolved in 0.5 w/v % mannitol solution. The compound at 0.05 mg/kg was subcutaneously administered at day 1 and then at 0.15 mg/kg at day 4. Body weight was measured once during the pre-dosing period and on day 1, 4, 8, 11 and 15. Food intake was measured every day during the experimental period.

P41 enhanced a sense of satiety without malaise in cynomolgus monkeys. Effect of P41 on food intake was investigated in cynomolgus monkeys to confirm of the efficacy and emetic effect on the primates. P41 was subcutaneously administered with escalating doses (0.05 and 0.15 mg/kg; ca. 10 and 30 nmol/kg). P41 almost completely abolished food consumption in a male and a female after dosing at both doses. Inhibitory effect of food consumption sustained at least for 2 days (FIG. 8). P41 did not induce vomiting throughout the experimental period, indicating that potent anorectic effect and little CTA effect of P41 observed in mice translated to non-human primate.

Formulation Example 1

| | |
|---|---|
| (1) Compound of Example 1 | 10.0 mg |
| (2) Lactose | 70.0 mg |

| | |
|---|---|
| (3) Cornstarch | 50.0 mg |
| (4) Soluble starch | 7.0 mg |
| (5) Magnesium stearate | 3.0 mg |

Compound of Example 1 (10.0 mg) and magnesium stearate (3.0 mg) are granulated with an aqueous soluble starch solution (0.07 ml) (7.0 mg as soluble starch), dried and mixed with lactose (70.0 mg) and cornstarch (50.0 mg). The mixture is compressed to give a tablet.

Formulation Example 2

| | |
|---|---|
| (1) Compound of Example 1 | 5.0 mg |
| (2) Sodium chloride | 20.0 mg |
| (3) Distilled water to total amount | 2 ml |

Compound of Example 1 (5.0 mg) and sodium chloride (20.0 mg) are dissolved in distilled water, and water is added to a total amount of 2.0 ml. The solution is filtered, and filled in a 2 ml ampoule under aseptic conditions. The ampoule is sterilized and tightly sealed to give a solution for injection.

INDUSTRIAL APPLICABILITY

The compound of the present invention has an activating action on Y2 receptor, GLP-1 receptor and GIP receptor, and may be useful as a drug for the prophylaxis or treatment of various diseases associated with Y2 receptor, GLP-1 receptor and GIP receptor, for example, obesity and diabetes.

All the publications, patents, and the patent applications cited herein are incorporated herein by reference in their entireties.

FREE TEXT FOR SEQUENCE LISTING

SEQ ID NO: 1: Artificial sequence (synthetic peptide (formula (I), formula (II) or formula (III)))
SEQ ID NO: 2: Artificial sequence (Synthetic peptide (Reference Example 1))
SEQ ID NO: 3: Artificial sequence (Synthetic peptide (Reference Example 2))
SEQ ID NO: 4: Artificial sequence (Synthetic peptide (Reference Example 3))
SEQ ID NO: 5: Artificial sequence (Synthetic peptide (Reference Example 4))
SEQ ID NO: 6: Artificial sequence (Synthetic peptide (Reference Example 5))
SEQ ID NO: 7: Artificial sequence (Synthetic peptide (Reference Example 6))
SEQ ID NO: 8: Artificial sequence (Synthetic peptide (Reference Example 7))
SEQ ID NO: 9: Artificial sequence (Synthetic peptide (Reference Example 8))
SEQ ID NO: 10: Artificial sequence (Synthetic peptide (Example 1))
SEQ ID NO: 11: Artificial sequence (Synthetic peptide (Example 2))
SEQ ID NO: 12: Artificial sequence (Synthetic peptide (Example 3))
SEQ ID NO: 13: Artificial sequence (Synthetic peptide (Example 4))
SEQ ID NO: 14: Artificial sequence (Synthetic peptide (Example 5))
SEQ ID NO: 15: Artificial sequence (Synthetic peptide (Example 6))
SEQ ID NO: 16: Artificial sequence (Synthetic peptide (Example 7))
SEQ ID NO: 17: Artificial sequence (Synthetic peptide (Example 8))
SEQ ID NO: 18: Artificial sequence (Synthetic peptide (Example 9))
SEQ ID NO: 19: Artificial sequence (Synthetic peptide (Example 10))
SEQ ID NO: 20: Artificial sequence (Synthetic peptide (Example 11))
SEQ ID NO: 21: Artificial sequence (Synthetic peptide (Example 12))
SEQ ID NO: 22: Artificial sequence (Synthetic peptide (Example 13))
SEQ ID NO: 23: Artificial sequence (Synthetic peptide (Example 14))
SEQ ID NO: 24: Artificial sequence (Synthetic peptide (Example 15))
SEQ ID NO: 25: Artificial sequence (Synthetic peptide (Example 16))
SEQ ID NO: 26: Artificial sequence (Synthetic peptide (Example 17))
SEQ ID NO: 27: Artificial sequence (Synthetic peptide (Example 18))
SEQ ID NO: 28: Artificial sequence (Synthetic peptide (Example 19))
SEQ ID NO: 29: Artificial sequence (Synthetic peptide (Example 20))
SEQ ID NO: 30: Artificial sequence (Synthetic peptide (Example 21))
SEQ ID NO: 31: Artificial sequence (Synthetic peptide (Example 22))
SEQ ID NO: 32: Artificial sequence (Synthetic peptide (Example 23))
SEQ ID NO: 33: Artificial sequence (Synthetic peptide (Example 24))
SEQ ID NO: 34: Artificial sequence (Synthetic peptide (Example 25))
SEQ ID NO: 35: Artificial sequence (Synthetic peptide (Example 26))
SEQ ID NO: 36: Artificial sequence (Synthetic peptide (Example 27))
SEQ ID NO: 37: Artificial sequence (Synthetic peptide (Example 28))
SEQ ID NO: 38: Artificial sequence (Synthetic peptide (Example 29))
SEQ ID NO: 39: Artificial sequence (Synthetic peptide (Example 30))
SEQ ID NO: 40: Artificial sequence (Synthetic peptide (Example 31))
SEQ ID NO: 41: Artificial sequence (Synthetic peptide (Example 32))
SEQ ID NO: 42: Artificial sequence (Synthetic peptide (Example 33))
SEQ ID NO: 43: Artificial sequence (Synthetic peptide (Example 34))
SEQ ID NO: 44: Artificial sequence (Synthetic peptide (Example 35))
SEQ ID NO: 45: Artificial sequence (Synthetic peptide (Example 36))
SEQ ID NO: 46: Artificial sequence (Synthetic peptide (Example 37))
SEQ ID NO: 47: Artificial sequence (Synthetic peptide (Example 38))

SEQ ID NO: 48: Artificial sequence (Synthetic peptide (Example 39))
SEQ ID NO: 49: Artificial sequence (Synthetic peptide (Example 40))
SEQ ID NO: 50: Artificial sequence (Synthetic peptide (Example 41))
SEQ ID NO: 51: Artificial sequence (Synthetic peptide (Example 42))

What is claimed is:

1. A peptide represented by the formula (I):

P¹-Tyr-Aib-Glu-Gly-Thr-α-MePhe-Thr-Ser-Asp-Lys(-Gly-Gly-Gly-Gly-$R^{410}$)-A11-A12-Aib-Leu-A15-Lys-Gln-A18-Gln-Iva-Glu-Phe-Val-Arg-His-Leu-Leu-Asn-Lys-Aib-Thr-Arg-Gln-Arg-A35-NH₂ wherein

P¹ is a group represented by the formula:
—$R^{41}$,
—CO—$R^{41}$,
—CO—O$R^{41}$,
—CO—CO$R^{41}$,
—SO—$R^{41}$,
—SO₂—$R^{41}$,
—SO₂—O$R^{41}$,
—CO—N$R^{42}R^{43}$,
—SO₂—N$R^{42}R^{43}$,
or
—C(=N$R^{41}$)—N$R^{42}R^{43}$ wherein $R^{41}$, $R^{42}$ and $R^{43}$ are each independently a hydrogen atom, an optionally substituted hydrocarbon group, or an optionally substituted heterocyclic group;

$R^{410}$ is Pal or Oda;

A11 is Aib, Ala or Ser;

A12 is Ile or Lys;

A15 is Asp or Glu;
A18 is Ala or Arg; and
A35 is Tyr or Phe(2-F),
or a salt thereof.

2. The peptide according to claim 1 or a salt thereof, wherein $P^1$ is a hydrogen atom or a methyl group.

3. The peptide according to claim 1 or a salt thereof, wherein $R^{410}$ is Pal.

4. The peptide according to claim 1 or a salt thereof, wherein A12 is Ile.

5. The peptide according to claim 1 or a salt thereof, wherein A15 is Glu.

6. The peptide according to claim 1 or a salt thereof, wherein A18 is Arg.

7. The peptide according to claim 1 or a salt thereof, wherein A35 is Tyr.

8. H-Tyr-Aib-Glu-Gly-Thr-αMePhe-Thr-Ser-Asp-Lys(-Gly-Gly-Gly-Gly-Pal)-Aib-Ile-Aib-Leu-Glu-Lys-Gln-Arg-Gln-Iva-Glu-Phe-Val-Arg-His-Leu-Leu-Asn-Lys-Aib-Thr-Arg-Gln-Arg-Tyr-NH$_2$
or a salt thereof.

9. H-Tyr-Aib-Glu-Gly-Thr-αMePhe-Thr-Ser-Asp-Lys(-Gly-Gly-Gly-Gly-Pal)-Ala-Ile-Aib-Leu-Glu-Lys-Gln-Arg-Gln-Iva-Glu-Phe-Val-Arg-His-Leu-Leu-Asn-Lys-Aib-Thr-Arg-Gln-Arg-Tyr-NH$_2$
or a salt thereof.

10. Me-Tyr-Aib-Glu-Gly-Thr-αMePhe-Thr-Ser-Asp-Lys(-Gly-Gly-Gly-Gly-Pal)-Ser-Ile-Aib-Leu-Glu-Lys-Gln-Arg-Gln-Iva-Glu-Phe-Val-Arg-His-Leu-Leu-Asn-Lys-Aib-Thr-Arg-Gln-Arg-Tyr-NH$_2$
or a salt thereof.

11. A medicament comprising the peptide according to claim 1 or a salt thereof.

12. The medicament according to claim 11, which is an activator of a Y2 receptor, a GLP-1 receptor and a GIP receptor.

13. The medicament according to claim 11, which is an agent for the prophylaxis or treatment of obesity or diabetes.

14. A method for the prophylaxis or treatment of obesity or diabetes in a mammal, comprising administering an effective amount of the peptide according to claim 1 or a salt thereof to the mammal.

15. A method for activating a Y2 receptor, a GLP-1 receptor and a GIP receptor in a mammal, comprising administering an effective amount of the peptide according to claim 1 or a salt thereof to the mammal.

* * * * *